US012583905B2

(12) United States Patent
Konto et al.

(10) Patent No.: US 12,583,905 B2
(45) Date of Patent: *Mar. 24, 2026

(54) METHODS AND COMPOSITIONS FOR DOSING OF ALLOGENEIC CHIMERIC ANTIGEN RECEPTOR T CELLS

(71) Applicants: Allogene Therapeutics, Inc., South San Francisco, CA (US); Les Laboratoires Servier, Suresnes (FR)

(72) Inventors: Cyril Alkis Konto, San Francisco, CA (US); Amina Zinai, Paris (FR)

(73) Assignees: Allogene Therapeutics, Inc., South San Francisco, CA (US); Les Laboratoires Servier, Suresnes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/953,634

(22) Filed: Nov. 20, 2024

(65) Prior Publication Data

US 2025/0084149 A1 Mar. 13, 2025

Related U.S. Application Data

(63) Continuation of application No. 18/484,244, filed on Oct. 10, 2023, now Pat. No. 12,221,462, which is a continuation of application No. 16/175,663, filed on Oct. 30, 2018, now abandoned.

(60) Provisional application No. 62/750,215, filed on Oct. 24, 2018, provisional application No. 62/716,898, filed on Aug. 9, 2018, provisional application No. 62/579,426, filed on Oct. 31, 2017.

(51) Int. Cl.
| | |
|---|---|
| *C07K 14/705* | (2006.01) |
| *A61K 31/664* | (2006.01) |
| *A61K 31/7076* | (2006.01) |
| *A61K 38/17* | (2006.01) |
| *A61K 39/00* | (2006.01) |
| *A61K 39/395* | (2006.01) |
| *A61K 40/11* | (2025.01) |
| *A61K 40/31* | (2025.01) |
| *A61K 40/42* | (2025.01) |
| *A61K 40/50* | (2025.01) |
| *A61P 35/00* | (2006.01) |
| *C07K 14/725* | (2006.01) |
| *C07K 16/28* | (2006.01) |
| *C07K 16/30* | (2006.01) |
| *C12N 5/0783* | (2010.01) |

(52) U.S. Cl.
CPC ...... *C07K 14/70578* (2013.01); *A61K 31/664* (2013.01); *A61K 31/7076* (2013.01); *A61K 38/177* (2013.01); *A61K 38/1774* (2013.01); *A61K 39/001102* (2018.08); *A61K 39/3955* (2013.01); *A61K 40/11* (2025.01); *A61K 40/31* (2025.01); *A61K 40/4211* (2025.01); *A61P 35/00* (2018.01); *C07K 14/7051* (2013.01);

*C07K 14/70517* (2013.01); *C07K 16/2803* (2013.01); *C07K 16/2893* (2013.01); *C07K 16/3061* (2013.01); *C12N 5/0636* (2013.01); *A61K 2039/505* (2013.01); *A61K 2039/507* (2013.01); *A61K 2039/545* (2013.01); *A61K 40/50* (2025.01); *A61K 2239/23* (2023.05); *A61K 2239/31* (2023.05); *A61K 2239/38* (2023.05); *A61K 2239/48* (2023.05); *A61K 2300/00* (2013.01); *C07K 2317/565* (2013.01); *C07K 2317/622* (2013.01); *C07K 2317/73* (2013.01); *C07K 2319/03* (2013.01); *C07K 2319/30* (2013.01); *C07K 2319/33* (2013.01); *C12N 2506/11* (2013.01)

(58) Field of Classification Search
CPC ................ A61K 40/31; A61K 2239/10; A61K 2239/28; A61K 2239/38
See application file for complete search history.

(56) References Cited

U.S. PATENT DOCUMENTS

| | | | |
|---|---|---|---|
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,750,373 A | 5/1998 | Garrard et al. | |
| 9,855,298 B2 | 1/2018 | Bot et al. | |
| 12,221,462 B2 * | 2/2025 | Konto ............... | C07K 14/7051 |
| 2014/0271635 A1 | 9/2014 | Brogdon et al. | |
| 2016/0145337 A1 * | 5/2016 | Galetto ............. | C07K 14/7051 |
| 2016/0206656 A1 | 7/2016 | Gilbert | |

(Continued)

FOREIGN PATENT DOCUMENTS

| | | |
|---|---|---|
| CN | 106117366 A | 11/2016 |
| CN | 106520806 A | 3/2017 |

(Continued)

OTHER PUBLICATIONS

Turtle et al. (Science Translational Medicine Sep. 7, 2016, 8 (355ra116): 1-12) (Year: 2016).*
Qasim et al. (Sci. Transl. Med. Jan. 25, 2017 9 (eaaj2013): 1-8) (Year: 2017).*
Examination Report Received in Canadian Application No. 3079747, mailed on Jun. 5, 2023, 4 pages.
Final Office Action Received in U.S. Appl. No. 16/175,663, mailed on Jun. 28, 2021, 11 pages.
Final Office Action Received in U.S. Appl. No. 16/175,663, mailed on Nov. 4, 2022, 22 pages.

(Continued)

*Primary Examiner* — Peter J Reddig
(74) *Attorney, Agent, or Firm* — Mintz Levin Cohn Ferris Glovsky and Popeo, P.C.

(57) ABSTRACT

The present disclosure concerns dosages for the treatment of human patients susceptible to or diagnosed with a disease, such as cancer. Provided are methods for administering chimeric antigen receptor (CAR)-T cells. Also provided are compositions and articles of manufacture for use in the methods.

25 Claims, 22 Drawing Sheets

Specification includes a Sequence Listing.

(56)                    References Cited

U.S. PATENT DOCUMENTS

| | | | | |
|---|---|---|---|---|
| 2016/0346326 A1* | 12/2016 | Bot | .................... | A61K 31/675 |
| 2016/0362472 A1 | 12/2016 | Bitter et al. | | |
| 2017/0002060 A1 | 1/2017 | Bolen et al. | | |
| 2019/0125799 A1 | 5/2019 | Konto et al. | | |
| 2024/0041930 A1 | 2/2024 | Konto et al. | | |
| 2024/0277763 A1* | 8/2024 | Pertel | .................... | A61K 40/11 |

FOREIGN PATENT DOCUMENTS

| | | | |
|---|---|---|---|
| CN | 106520837 A | 3/2017 | |
| CN | 106544365 A | 3/2017 | |
| CN | 107287164 A | 10/2017 | |
| JP | 2016520074 A | 7/2016 | |
| TW | 201502139 A | 1/2015 | |
| WO | 2013153391 A1 | 10/2013 | |
| WO | 2014184143 A1 | 11/2014 | |
| WO | 2015123642 A1 | 8/2015 | |
| WO | 2016019300 A1 | 2/2016 | |
| WO | 2019089650 A1 | 5/2019 | |

OTHER PUBLICATIONS

International Preliminary Report on Patentability Received in PCT Application No. PCT/US2018/058288, mailed on May 14, 2020, 20 pages.
International Search Report and Written Opinion Received in PCT/US2018/058288, mailed on Apr. 16, 2019, 28 Pages.
Non-Final Office Action Received in U.S. Appl. No. 18/484,244, mailed on Nov. 30, 2023, 18 pages.
Non-Final Office Action Received in U.S. Appl. No. 16/175,663, mailed on Oct. 23, 2020, 13 pages.
Non-Final Office Action Received in U.S. Appl. No. 16/175,663, mailed on May 4, 2022, 20 pages.
Invitation to Pay Additional Fees Received in PCT Application No. PCT/US2018/058288, mailed on Feb. 26, 2019, 25 pages.
Notice of Acceptance Received in Australian Application No. 2018360566, mailed on Aug. 30, 2024, 3 pages.
Notice of Acceptance Received in Israel Application No. 274160, mailed on Nov. 4, 2024, 3 pages.
Office Action Received in Israel Application No. 274160, mailed on Feb. 26, 2024, 4 pages.
Notice of Allowance Received in U.S. Appl. No. 18/484,244, mailed on Aug. 21, 2024, 7 pages.
Notice of Allowance Received in U.S. Appl. No. 18/484,244, mailed on May 28, 2024, 7 pages.
Requirement for Restriction/Election Received in U.S. Appl. No. 16/175,663, mailed on Jun. 24, 2020, 12 pages.
Office Action Received in Argentina Application No. P180103160 and translation, mailed on Feb. 17, 2022, 6 Pages.
Office Action Received in Australian Application No. 2018360566, mailed on Dec. 4, 2023, 5 pages.
Office Action Received in European Application No. 18804466.3, mailed on Mar. 20, 2023, 10 pages.
Office Action Received in European Application No. 18804466.3, Mailed on Sep. 18, 2023, 5 pages.
Search Report and Written Opinion Received in Singapore Application No. 1202003849V, mailed on Nov. 11, 2021, 15 pages.
Written Opinion Received in Singapore Application No. 11202003849V, mailed on Aug. 21, 2023, 5 pages.
"Unit Dose", Collins, Retrieved from https://www.collinsdictionary.com/us/dictionary/english/unit-dose, Retrieved on Apr. 28, 2022, 1 Page.
Boerner et al. (Jul. 1, 1991) "Production of Antigen-Specific Human Monoclonal Antibodies from in Vitro-Primed Human Splenocytes", Journal of Immunology, 147(1):86-95.
Chothia et al. (Aug. 20, 1987) "Canonical Structures for the Hypervariable Regions of Immunoglobulins", Journal of Molecular Biology, 196(4):901-917.

Cole et al. (1985) "Monoclonal Antibodies and Cancer Therapy", UCLA symposia on molecular and cellular biology, 77-96.
Gouble et al. (Dec. 6, 2014) "In Vivo Proof of Concept of Activity and Safety of UCART19, an Allogeneic "Off-the-Shelf" Adoptive T-Cell Immunotherapy Against CD19+ B-Cell Leukemias", Blood, 124(21):4689(2 pages).
Harlow et al. (1999) "Using Antibodies: A laboratory Manual", New York:Cold Spring Harbor Laboratory, 2 pages.
Holliger et al. (2005) "Engineered Antibody Fragments and the Rise of Single Domains", Nature Biotechnology, 23(9):1126-1136.
Hoogenboom et al. (Sep. 20, 1992) "By-passing Immunisation: Human Antibodies from Synthetic Repertoires of Germline VH Gene Segments Rearranged in Vitro", Journal of molecular biology, 227(2):381-388.
Lee et al. (2014) "Current Concepts in the Diagnosis and Management of Cytokine Release Syndrome", Blood, 124(2):188-195.
Marks et al. (1991) "By-passing Immunization Human Antibodies from V-gene Libraries Displayed on Phage", Journal of molecular biology, 222(3):581-597.
Mihara et al. (Nov. 2004) "Development of Effective Immunotherapy for B-Cell Non-Hodgkin's Lymphoma with CD19-Specific Cytotoxic T Cells", Blood, 104(11):3277(2 pages).
Onea et al. (2016) "CD19 Chimeric Antigen Receptor (CD19 CAR)-redirected Adoptive T-cell Immunotherapy for the Treatment of Relapsed or Refractory B-cell Non-Hodgkin's Lymphomas", American Journal of Cancer Research, 6(2):403-424.
Poirot et al. (May 2015) "UCART19, An Allogeneic "Off-the-Shelf" Adoptive T-Cell Immunotherapy Against CD19+ B-Cell Leukemias", Molecular Therapy, 23(Supplement 1), pp. S286.
Qasim et al. (Jan. 2017) "Molecular Remission of Infant B-ALL After Infusion of Universal TALEN Gene-Edited Car T Cells", Science Translational Medicine, 9(374):eaaj2013:1-8.
Saif et al. (Mar. 2015) "In vivo T-cell Depletion using Alemtuzumab in Family and Unrelated Donor Transplantation for Pediatric Non-malignant Disease Achieves Engraftment with Low Incidence of Graft vs. Host Disease", Pediatric Transplantation, 19(2):211-218.
Sambrook et al. (1989) "Molecular Cloning: A Laboratory Manual", Cold Spring Harbor Laboratory Press, 2nd Edition, 30 pages.
Sheets et al. (May 26, 1998) "Efficient Construction of a Large Nonimmune Phage Antibody Library: The Production of High-Affinity Human Single-Chain Antibodies to Protein Antigens", Proceedings of the National Academy of Sciences, 95(11):6157-6162.
Shimasaki et al. (2012) "A Clinically Adaptable Method to Enhance the Cytotoxicity of Natural Killer Cells Against B- cell Malignancies", Cytotherapy, 14(7):830-840.
Turtle et al. (Sep. 7, 2016) "Immunotherapy of Non-Hodgkin Lymphoma with a Defined Ratio of CD8+ and CD4+ CD19-specific Chimeric Antigen Receptor-modified T cells", Science Translational Medicine, 8(355):355ra116 (13 pages).
Turtle et al. (2016) "Supplementary Materials for Immunotherapy of Non-Hodgkin Lymphoma with a Defined Ratio of CD8+ and CD4+ CD19-specific Chimeric Antigen Receptor-modified T cells", Science Translational Medicine, 8(355):355ra116 (16 pages).
Vaughan et al. (Mar. 1996) "Human Antibodies with Sub-nanomolar Affinities Isolated from a Large Non- immunized Phage Display Library", Nature Biotechnology, 14(3):309-314.
Ward et al. (Oct. 12, 1989) "Binding Activities of a Repertoire of Single Immunoglobulin Variable Domains Secreted from *Escherichia coli*", Nature, 341(6242):544-546.
Extended European Search Report received in European Patent Application No. 24192728.4, mailed on Feb. 24, 2025, 14 pages.
Notice of Allowance Issued in Philippines Patent Application No. 1-2020-550598, mailed on May 13, 2025, 3 pages.
Office Action received in Canadian Patent Application No. 3,079,747, mailed on Feb. 27, 2025, 6 pages.
Subsequent Substantive Examination Report received in Philippines Patent Application No. 1-2020-550598, mailed on Jan. 28, 2025, 6 pages.
Substantive Examination Report Received in Philippines Patent Application No. 1-2020-550598, mailed on Oct. 11, 2024, 6 pages.
Allogene Therapeutics (Dec. 1, 2023) "Safety and Efficacy of ALLO-501 Anti-CD19 Allogeneic CAR T Cells in Adults With

(56)                    References Cited

OTHER PUBLICATIONS

Relapsed/IIRefractory Large B Cell or Follicular Lymphoma (ALPHA)", ClinicalTrials.gov ID: NCT03939026, 9 pages.

Allogene Therapeutics (Jan. 24, 2025) "Safety and Efficacy of ALLO-501A Anti-CD19 Allogeneic CAR T Cells in Adults with Relapsed/IRefractory Large B Cell Lymphoma, Chronic Lymphocytic Leukemia and Small Lymphocytic Lymphoma (ALPHA2) (ALPHA2)", ClinicalTrials.gov ID: NCT04416984, 16 pages.

Hartmann et al. (2017) "Clinical Development of CAR T Cells-Challenges and Opportunities in Translating Innovative Treatment Concepts", EMBO Molecular Medicine, 9(9):1183-1197.

Locke et al. (Feb. 17, 2022) "Axicabtagene Ciloleucel as Second-Line Therapy for Large B-Cell Lymphoma", The New England Journal of Medicine, 386(7):640-654.

Tilly et al. (Jan. 27, 2022) "Polatuzumab Vedotin in Previously Untreated Diffuse Large B-Cell Lymphoma", The New England Journal of Medicine, 386(4):351-363.

Cruz et al. (2013) "Infusion of Donor-derived CD19-redirected Virus-specific T Cells for B-cell Malignancies Relapsed After Allogeneic Stem Cell Transplant: A Phase 1 Study", Blood, 122(17):2965-2973.

Kochenderfer et al. (2013) "Donor-derived CD19-targeted T Cells Cause Regression of Malignancy Persisting After Allogeneic Hematopoietic Stem Cell Transplantation", Blood, 122(25):4129-4139.

* cited by examiner

FIG. 6A

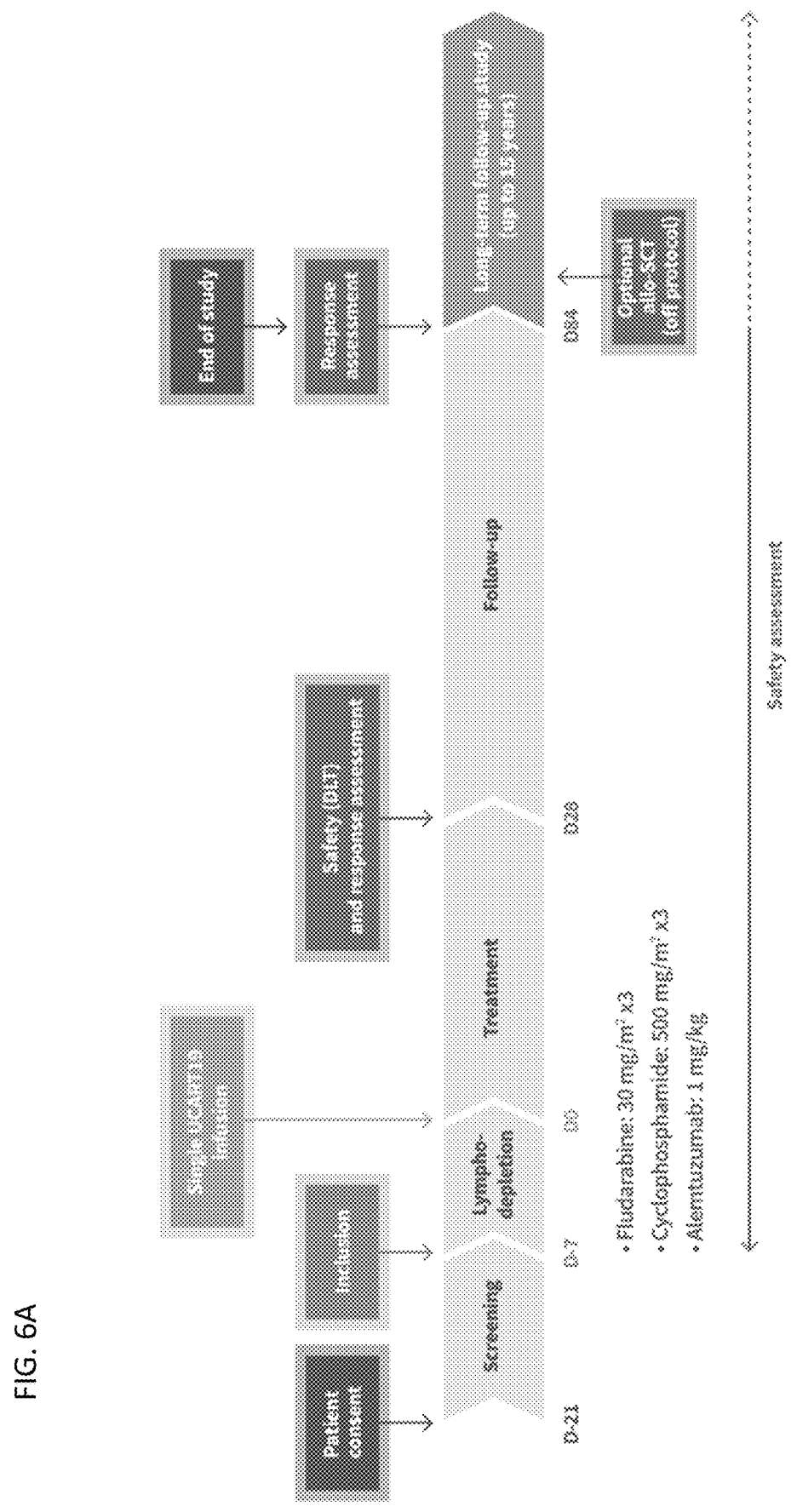

Patient consent

Screening

Inclusion

Sponsor's decision on patient

Lympho-depletion

Safety (DLT) and response assessment

End of study

Recipient depletion

Long-term follow-up (gene therapy safety)

Follow-up

Treatment

D-21    D-7    D0    D28    D84

- Fludarabine: 30 mg/m² x3
- Cyclophosphamide: 500 mg/m² x3
- Alemtuzumab: 1 mg/kg Safety assessment

METHODS AND COMPOSITIONS FOR DOSING OF ALLOGENEIC CHIMERIC ANTIGEN RECEPTOR T CELLS

CROSS-REFERENCE TO RELATED APPLICATIONS

This application is a continuation of U.S. patent application Ser. No. 18/484,244, filed Oct. 10, 2023, which is a continuation of U.S. patent application Ser. No. 16/175,663, filed Oct. 30, 2018, now abandoned, which claims priority to U.S. Provisional Application Ser. No. 62/750,215, filed Oct. 24, 2018, U.S. Provisional Application Ser. No. 62/716,898, filed Aug. 9, 2018, and U.S. Provisional Application Ser. No. 62/579,426, filed Oct. 31, 2017, the disclosures of each of which are incorporated by reference herein in their entirety for all purposes.

FIELD

The present disclosure concerns therapeutic regimens for treatment of disorders, including proliferative disorders and immune disorders. The subject therapeutic regimens involve administration of one or multiple doses of immune cells comprising allogeneic chimeric antigen receptor T cells. The subject therapeutic regimens can be used in the prevention and/or treatment of disorders, including cancer.

DESCRIPTION OF THE TEXT FILE SUBMITTED ELECTRONICALLY

The contents of the text file submitted electronically herewith are incorporated by reference in their entirety: a computer readable format copy of the Sequence Listing (filename: ALG-012US2_SL.xml, date recorded Sep. 26, 2023, file size 44 kilobytes).

BACKGROUND

Various methods are available for adoptive cell therapy using engineered cells expressing recombinant receptors, such as chimeric antigen receptor (CAR)-T cells. However, the doses of allogeneic CAR-T cells required to be effective to treat disease and achieve remission in human patients are not known. Provided herein are methods, compositions, and articles of manufacture for dosing and re-dosing patients with allogeneic CAR-T cells. The disclosed methods reduce the risk of toxicity and/or increase efficacy, for example, by increasing exposure of the subject to the administered cells (e.g., by improving expansion and/or persistence of the administered cells).

SUMMARY

This disclosure relates to therapeutic regimens for treatment of a disorder, such as cancer. More specifically, this disclosure relates to therapeutic regimens for treatment of a disorder, such as cancer, by administration of allogeneic CAR-T-cells. Features of the methods, including the timing of the doses and numbers of cells administered, provide various advantages, such as improved efficacy and/or lower toxicity, for example, due to increased exposure of the subject to the administered cells.

Provided are methods for administering to subjects CAR-T cells, for example, to treat diseases and/or disorders in the subjects. The methods generally involve administering single or multiple doses of such cells, and/or administering a subsequent dose to a subject having been previously treated with a prior (e.g., first) dose of such cells. Also provided are cells, compositions, and articles of manufacture for use in such methods.

In some embodiments, the methods involve treating an adult subject who has refractory and/or relapsed CD19+ B-cell acute lymphoblastic leukemia, comprising administering to the subject at least one dose of allogeneic chimeric antigen receptor (CAR)-T cells (CAR-T cells) comprising an anti-human CD19 4-1BB/CD3zeta CAR (e.g. UCART19 (CD19CAR/RQR8+_TCRαβ-_T-cells), wherein the at least one dose is selected from the group consisting of about $6 \times 10^5$ cell/dose, about $6 \times 10^6$ cells/dose, about $6\text{-}8 \times 10^7$ cells/dose, and about $1.8\text{-}2.4 \times 10^8$ cells/dose.

In some embodiments, the methods involve treating a pediatric subject who has refractory and/or relapsed CD19+ B-cell acute lymphoblastic leukemia, comprising administering to the subject at least one dose of allogeneic chimeric antigen receptor (CAR)-T cells (CAR-T cells) comprising an anti-human CD19 4-1BB/CD3zeta CAR (e.g. UCART19 (CD19CAR/RQR8+_TCRαβ-_T-cells) or UCART19 (CD19CAR/R2+_TCRαβ-_T-cells) or UCART19 (CD19CAR/TCRαβ-_T-cells), wherein the at least one dose is about $2\text{-}8 \times 10^7$ cells/dose.

In some embodiments, the methods involve treating a subject who has refractory and/or relapsed Non-Hodgkin's Lymphoma (e.g., large B-cell lymphoma or follicular lymphoma), the method comprising administering to the subject at least one dose of allogeneic chimeric antigen receptor (CAR)-T cells (CAR-T cells) comprising an anti-human CD19 4-1BB/CD3zeta CAR (CD19CAR/RQR8+_TCRαβ-_T-cells), wherein the at least one dose is about $20 \times 10^6$ cells/dose to about $360 \times 10^6$ cells/dose, for example about $20 \times 10^6$ cells/dose, about $40 \times 10^6$ cells/dose, about $80 \times 10^6$ cells/dose, about $120 \times 10^6$ cells/dose, $240 \times 10^6$ cells/dose, or about $360 \times 10^6$ cells/dose.

In some embodiments, the methods involve (a) administering to a subject with a disease a first dose of allogeneic CAR-T cells; and (b) administering to the subject a subsequent dose of allogeneic CAR-T cells. In other embodiments, the methods are carried out by administering to the subject the subsequent dose or doses as in (b), to a subject that has been previously administered the first dose as in (a). In some embodiments, the CAR-T cells are tumor antigen-specific CAR-T cells. In some embodiments, the CAR-T cells are CD19-specific CAR-T cells (e.g., UCART19 (CD19CAR/RQR8+_TCRαβ-_T-cells)). In some embodiments, the disease is a tumor. In some embodiments, it is a cancer, malignancy, neoplasm, or other proliferative disease or disorder, such as leukemia, lymphoma, e.g., chronic lymphocytic leukemia (CLL), acute lymphoblastic leukemia (ALL (e.g., relapsed/refractory ALL)), non-Hodgkin's lymphoma, acute myeloid leukemia, diffuse large B-cell lymphoma (DLBCL), multiple myeloma, follicular lymphoma, mantle cell lymphoma, indolent B cell lymphoma, B cell malignancies, cancers of the colon, lung (e.g., small and non-small cell lung cancer), liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, head and neck squamous cell carcinoma (HNSCC), and/or mesothelioma. In some embodiments, the disease is a leukemia or lymphoma. In some embodiments, the disease is acute lymphoblastic leukemia. In some embodiments, the disease is relapsed or refractory acute lymphoblastic leukemia. In some embodiments, the disease is non-Hodgkin lymphoma (NHL). In some embodiments, the disease is relapsed or refractory large B-cell lymphoma. In some embodiments, the disease is relapsed or refractory follicular lymphoma.

In some embodiments the disease is acute lymphoblastic leukemia (ALL). In some embodiments the disease is pediatric acute lymphoblastic leukemia (ALL). In some embodiments the disease is an advanced lymphoid malignancy such as B-cell acute lymphoblastic leukemia (B-ALL). In some embodiments, the disease is refractory B-ALL, e.g. adult refractory B-ALL. In some embodiments, the disease is relapsed B-ALL, e.g. adult relapsed B-ALL. In some embodiments, the disease is extramedullary disease associated, for example, with one or more of the cancers described herein. In some embodiments, the subject exhibits detectable molecular disease and/or minimum residual disease at the time of the administration of the subsequent dose. In some embodiments, the subject exhibits one or more symptoms of the disease at the time of the administration of the subsequent dose. In some embodiments, the disease is a cancer and the subject exhibits relapse at the time of initiation of the administration of the subsequent dose. In some embodiments, the disease is a leukemia or lymphoma and the subject exhibits greater than 5% blast cells in the bone marrow at the time of the administration of the subsequent dose.

In some embodiments, the disease is a cancer and the subject exhibits morphologic disease. In some embodiments, the disease is a leukemia or lymphoma and the subject exhibits extramedullary disease (i.e., presence of blasts outside bone marrow) at the time of the administration of the subsequent dose. In some embodiments, the disease is a leukemia or lymphoma and the subject exhibits greater than 5% blast cells in the bone marrow at the time of the administration of the subsequent dose. In other embodiments, the disease is a cancer and the subject does not exhibit morphologic disease at the time of initiation of the administration of the subsequent dose. In some embodiments, the disease is a leukemia or lymphoma and the subject does not exhibit greater than 5% blast cells in the bone marrow at the time of the administration of the subsequent dose.

In some embodiments, the methods involve (a) administering to a subject having a disease a first dose of allogeneic CAR-T cells. In some embodiments, the first dose contains about $1 \times 10^4$ cells, about $5 \times 10^4$ cells, about $1 \times 10^5$ cells, about $5 \times 10^5$ cells, about $1 \times 10^6$ cells, about $5 \times 10^6$ cells, about $6 \times 10^6$ cells, about $1 \times 10^7$ cells, about $6 \times 10^7$ cells, about $1 \times 10^8$, about $1.8 \times 10^8$ cells, or about $4.8 \times 10^8$ cells. In some embodiments, the first dose contains about $20 \times 10^6$ cells to about $360 \times 10^6$ cells, for example about $20 \times 10^6$ cells, about $40 \times 10^6$ cells, about $80 \times 10^6$ cells, about $120 \times 10^6$ cells, $240 \times 10^6$ cells, or about $360 \times 10^6$ cells. In some embodiments, the methods further involve (b) administering to the subject a subsequent dose of CAR-T cells at a time point that is at least or more than about 5 weeks after and less than about 24 weeks after initiation of the administration in (a).

In some embodiments, a subject with relapsed/refractory ALL is administered a first and subsequent dose of allogeneic CAR-T cells each containing about $6 \times 10^6$ cells, and the subsequent dose of CAR-T cells in (b) is administered about 99 days after initiation of the administration in (a).

In some embodiments, the methods further involve the administration of additional subsequent or subsequent doses, such that a first and multiple subsequent doses are administered, e.g., in accordance with the dosing amounts and timing schedules as specified for the first and subsequent doses. In some embodiments, the first of one or more subsequent doses is administered at a time that is at least or greater than 5 weeks after the initiation of the administration of the subsequent dose. In some embodiments, the administration of the first, second, and subsequent doses includes administering at least three of the doses within about 5 weeks. In some embodiments, the subsequent dose is administered at about 16 weeks following the initiation of administration of the first dose, and an additional subsequent or subsequent dose is administered at week 17 following the initiation of administration of the first dose. In some embodiments, additional subsequent doses are administered at week 17 and/or week 34 following the initiation of administration of the first dose.

In some aspects, the time of administering the subsequent dose(s) is further one at which the subject does not exhibit an immune response, e.g., does not exhibit a detectable adaptive host immune response specific for the CAR-T after said first (or prior) dose.

In some embodiments, the time between the administration of the first dose (initial dose), e.g., the initiation of the administration of the first or prior dose, and the initiation of the administration of the subsequent dose (e.g., the initiation of the administration of the subsequent dose) is greater than about 4 weeks, e.g., greater than about 5, 6, 7, 8, or 9 weeks, e.g., greater than about 20 weeks, e.g., between about 9 and about 35 weeks, between about 14 and about 28 weeks, between 15 and 27 weeks, or between 16 weeks and about 18 weeks; and/or at or about 15, 16, 17, 18, 19, 20, 21, 22, 23, 24, 25, 26, or 27 weeks. In some embodiments, administration of the subsequent dose (e.g., initiation thereof) is more than about 5 weeks after and less than about 24 weeks after administration of the first or prior dose (e.g., initiation thereof). In some embodiments, the administration of the subsequent dose is initiated 17 weeks following the initiation of the first dose. In some embodiments, the time between administration of the first and the subsequent dose (e.g., initiation thereof) or prior and next subsequent dose is greater than about 5 weeks and less than about 24 weeks, such as between 10 and 24 weeks, such as about 17 weeks. In some embodiments, the time between administration of the first and the subsequent dose (e.g., initiation thereof) is about 17 weeks. In some embodiments, administration of the subsequent dose (e.g., initiation thereof) is more than about 7 days after and less than about 365 days after administration of the first or prior dose (e.g., initiation thereof). In some embodiments, administration of the subsequent dose (e.g., initiation thereof) is more than about 30 days after and less than about 110 days after administration of the first or prior dose (e.g., initiation thereof).

In some embodiments, the subject exhibits an absence of persistence of CAR-T cells at the time of the administration of the subsequent dose. In some embodiments, the subject exhibits a suboptimal response at the time of the administration of the subsequent dose. In some embodiments, a suboptimal response may comprise any one or more of the following: (i) complete response (CR), complete response with incomplete recovery of blood count (CRi), with detectable minimal residual disease (leukemic patients) and absence of cytogenetic response; (ii) marrow complete response; (iii) partial response; or (iv) stable response.

In some embodiments, administration of the first dose leads to amelioration of one or more symptoms of the disease in the subject following administration of the first dose. In some embodiments, at the time of the administration of the subsequent dose, the subject has relapsed and/or one or more symptoms of the disease have increased following an initial amelioration (e.g., remission) experienced after the first dose.

In some embodiments, the subsequent dose of cells contains CAR-T cells in an amount sufficient for amelioration of the disease in the subject. In some embodiments, the administration of the subsequent dose leads to a further amelioration of the disease in the subject. In some embodiments, administration of the subsequent dose leads to amelioration of the disease in the subject as compared with immediately prior to initiation of the administration of the subsequent dose. In some embodiments, administration of the subsequent dose leads to MRD negativity. In some embodiments, the method ameliorates the disease to a greater degree and/or for a greater period of time as compared to a method with an alternative dosing regimen wherein the subject is administered the cells in the first dose and the cells in the subsequent dose in a single dose. The amelioration may comprise a reduction in total number of cells, e.g., tumor cells, of the disease in the subject, in an organ of the subject, in a tissue of the subject, or in a bodily fluid of the subject. The amelioration may comprise a reduction in molecular detection by flow cytometry or quantitative PCR, mass or volume of a tumor, and/or a reduction in number and/or extent of metastases. In some embodiments, the amelioration comprises improvement in survival of the subject, e.g., increased time of survival or incident-free, progression-free, or relapse-free survival.

In some embodiments, the disease persists following the administration of the first dose and/or the administration of the first dose is not sufficient to eradicate the disease in the subject. In some embodiments, the administration of said subsequent dose leads to amelioration of the disease in the subject as compared with immediately prior to initiation of the administration of the subsequent dose.

In some embodiments, the administration of the first dose does not induce severe cytokine release syndrome (CRS) in the subject. The severity of cytokine release syndrome (CRS), may be assessed according to the modified grading described by Lee D W, et al., Blood 2014; 124(2):188-195, which is incorporated by reference herein in its entirety. In some embodiments, administration of the first dose does not induce CRS in the subject. In some embodiments, based on clinical data, administration of the first dose does not induce severe CRS in a majority of subjects. In some embodiments, the administration of the first dose does not induce CRS encompassing a combination of (1) persistent fever (fever of at least 38 degrees Celsius for at least three days) and (2) a serum level of C reactive protein (CRP) of at least at or about 20 mg/dL, and/or does not induce CRS encompassing hypotension requiring the use of two or more vasopressors or respiratory failure requiring mechanical ventilation.

In some embodiments, administration of the first dose does not induce grade 3 or higher neurotoxicity in the subject. In some embodiments, based on clinical data, administration of the first dose does not induce grade 3 or higher neurotoxicity in a majority of subjects. In some embodiments, symptoms associated with a clinical risk of neurotoxicity and/or grade 3 or higher neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals.

In some embodiments, the subject has been treated with a therapeutic agent targeting the tumor prior to the administration of the first dose. In some aspects, the subject is refractory or non-responsive to said therapeutic agent at the time of the administration of the first dose and/or the subsequent dose. In some embodiments, subsequent to administration of the first dose and before said administration of the subsequent dose, or prior to administration of the first dose, the methods further include assessing a serum level of a factor indicative of CRS, a symptom of the disease, and/or an indicator of a host anti-recombinant receptor (e.g., anti-CAR) immune response in the subject, such as a humoral or cell-mediated immune response. In some such embodiments, the symptom of the disease detected is or comprises a total number of cells of the disease in the subject, in an organ of the subject, in a tissue of the subject, or in a bodily fluid of the subject, molecular detection by flow cytometry or quantitative PCR, mass or volume of a solid tumor, or number or extent of metastases.

In some embodiments, the methods include assessing a symptom of the disease prior to administration of the subsequent dose, and based on the result of the assessment, determining the subsequent dose of cells to be administered to the subject. In some embodiments, if the assessment determines that the subject has morphologic disease, the subject is administered a subsequent dose containing less than, greater than, or about the same number of allogeneic CAR-T cells as the number of allogeneic CAR-T cells in the first dose. In some embodiments, if the assessment determines that the subject has minimal residual disease, the subject is administered a subsequent dose containing an increased number of allogeneic CAR-T cells as compared to the first dose. In some embodiments, the subsequent dose comprises about the same number of allogeneic CAR-T cells as the number in the first dose. In some embodiments, the number of allogeneic CAR-T cells per kilogram administered in the subsequent dose is less than or is the same or about the same as the number of allogeneic CAR-T cells per kilogram administered in the first dose. In other embodiments, the number of allogeneic CAR-T cells administered in the subsequent dose is greater than the number of allogeneic CAR-T cells administered in the first dose. In some embodiments, the subsequent dose comprises an increased number of such cells as compared to the first dose, such as at least 2-fold, 5-fold, or 10-fold greater than the number in the first dose. In some embodiments, the number of CAR-T cells per kilogram administered in the subsequent dose is at least at or about 2 times or at or about 3 times greater than the number of receptor-expressing (e.g., CAR-expressing) cells per kilogram administered in the first dose.

In some embodiments, the population of allogeneic CAR-T cells in the first dose expands in the subject following administration of the first dose and/or following the administration of the subsequent dose. In some embodiments, the expansion is evidenced by an increase in serum C-reactive protein (CRP) level following the administration of the first dose and/or subsequent dose as compared to just prior to the administration. In some embodiments, the expansion is evidenced by PK as assessed by, e.g., without limitation, flow cytometry. In some embodiments, the expansion is evidenced by an increase in a level of CAR-encoding nucleic acid in the serum, as measured by qPCR, following the administration of the first dose and/or subsequent dose as compared to just prior to the administration. In some embodiments, the increase is at least 1, 2, or 3-fold.

In some embodiments, the cells of the first dose and the cells of the second or subsequent dose are derived from the same donor. In some embodiments, the cells of the first dose and the cells of the second or subsequent dose are derived from different donors.

In some embodiments, the first and/or subsequent dose is not a split dose. For example, in some embodiments, the cells of the first dose are administered in a single pharmaceutical composition comprising the cells of the first dose and/or the cells of the subsequent dose are administered in a single pharmaceutical composition comprising the cells of the subsequent dose. In other embodiments, the first and/or subsequent dose is a split dose, for example, where the cells of the first dose are administered in a plurality of compositions, collectively comprising the cells of the first dose, over a period of no more than three days; and/or the subsequent dose is a split dose, where the cells of the subsequent dose are administered in a plurality of compositions, collectively comprising the cells of the subsequent dose, over a period of no more than three days.

In some embodiments, the methods include administering a subsequent dose of allogeneic CAR-T cells to a subject previously administered a first dose of allogeneic CAR-T cells. In some embodiments, the subsequent dose of cells is administered at a time point that is at least or more than about 5 weeks after and less than about 24 weeks after initiation of the first dose. In some embodiments, the number of allogeneic CAR-T cells administered in the subsequent dose is the same as the first dose. In some embodiments, the CAR-T cells are CD19-specific CAR-T cells (e.g., UCART19).

In some embodiments, the number of cells administered in the first dose is between about $0.5\times10^6$ cells and $5\times10^8$ cells, between about $0.75\times10^6$ cells and $8\times10^7$ cells or between about $5\times10^6$ cells and $7\times10^6$ cells, each inclusive. In some embodiments, the number of cells administered in the first dose of CD19-specific CAR-T cells is between about $0.5\times10^6$ cells and $1\times10^9$ cells, between about $1\times10^5$ cells and $3\times10^8$ cells or between about $6\times10^5$ cells and $2.4\times10^8$ cells, each inclusive. In some embodiments, the number of cells administered in the first dose of UCART19 cells is about $6\times10^5$ cells, about $6\times10^6$ cells, about $6\times10^7$ cells, about $8\times10^7$ cells, about $1.8\times10^8$ cells, or about $2.4\times10^8$ cells. In some embodiments, the number of cells administered in the first dose of UCART19 cells is about $6\times10^6$ cells.

In some embodiments, the number of cells administered in the subsequent dose of CD19-specific CAR-T cells is between about $0.5\times10^6$ cells and $1\times10^9$ cells, between about $1\times10^5$ cells and $3\times10^8$ cells or between about $6\times10^5$ cells and $2.4\times10^8$ cells, each inclusive. In some embodiments, the number of cells administered in the subsequent dose of UCART19 cells is about $6\times10^5$ cells, about $6\times10^6$ cells, about $6\times10^7$ cells, about $8\times10^7$ cells, about $1.8\times10^8$ cells, or about $2.4\times10^8$ cells. In some embodiments, the number of cells administered in the subsequent dose of UCART19 cells is about $6\times10^6$ cells. In some embodiments, the number of cells administered in the first and subsequent dose of UCART19 cells is about $6\times10^6$ cells.

In some embodiments, the methods further include administering a lymphodepletion regimen prior to the first dose and/or prior to the administration of the subsequent dose. In some embodiments, the lymphodepletion regimen comprises cyclophosphamide, fludarabine, and/or a combination thereof. In some embodiments, the lymphodepletion regimen comprises one or more of cyclophosphamide, fludarabine, a CD52 antibody (e.g., an antibody comprising the sequence of SEQ ID NO:8 and/or SEQ ID NO:10), and/or a combination thereof. In some embodiments, the administration of the lymphodepletion regimen includes administration of cyclophosphamide and fludarabine prior to the administration of the first dose, and a CD-52 antibody (e.g., an antibody comprising the sequence of SEQ ID NO:8 and/or SEQ ID NO:10) after administration of the first dose. In some embodiments, the administration of the lymphodepletion regimen includes administration of a lymphodepletion regimen prior to the administration of the first dose and optionally not prior to the administration of the subsequent dose. In some embodiments, the lymphodepletion regimen is administered between 2 and 10 days prior to the administration of the first dose. In some embodiments, the lymphodepletion regimen is administered between 2 and 10 days prior to the administration of the second dose. In some embodiments, the lymphodepletion regimen is administered between 2 and 10 days prior to the administration first dose and between 2 and 14 days prior to the administration of the second dose. In some embodiments, the lymphodepletion regimen is administered over the course of 1, 2, 3, 4, or 5 days.

In some embodiments, a lymphodepletion regimen comprises administering about 90-120 mg/m$^2$ fludarabine and about 1500 mg/m$^2$ cyclophosphamide. In some embodiments, a lymphodepletion regimen comprises administering about 150 mg/m$^2$ fludarabine and about 120 mg/m$^2$ cyclophosphamide.

In some embodiments, a lymphodepletion regimen comprises administering fludarabine at a dosage of about 30 to 150 mg/m$^2$; cyclophosphamide at a dosage of about 300 to 4000 mg/m$^2$; or a CD52 antibody (e.g., a CD52 antibody comprising the sequence of SEQ ID NO:8 and/or SEQ ID NO:10) at a dosage of about 0.3 to 1 mg/kg. In some embodiments, fludarabine is administered at a dosage of about 30 to 150 mg/m$^2$; cyclophosphamide is administered at a dosage of about 300 to 4000 mg/m$^2$; and a CD52 antibody (e.g., a CD52 antibody comprising the sequence of SEQ ID NO:8 and/or SEQ ID NO:10) is administered at a dosage of about 10 to about 13 mg. In some embodiments, fludarabine is administered at a dosage of about 30 mg/m$^2$/day; cyclophosphamide is administered at a dosage of about 300 mg/m$^2$/day; or a CD52 antibody (e.g., a CD52 antibody comprising the sequence of SEQ ID NO:8 and/or SEQ ID NO:10) is administered at a dosage of about 10 to about 13 mg/day. In some embodiments, fludarabine is administered at a dosage of about 30 mg/m$^2$/day; cyclophosphamide is administered at a dosage of about 300 mg/m$^2$/day; and a CD52 antibody (e.g., a CD52 antibody comprising the sequence of SEQ ID NO:8 and/or SEQ ID NO:10) is administered at a dosage of about 10 to about 13 mg/day.

In some embodiments, a lymphodepletion regimen comprises administering fludarabine and cyclophosphamide. In some embodiments, a lymphodepletion regimen comprises administering fludarabine, cyclophosphamide, and an anti-CD52 drug (e.g., a CD52 antibody having the sequence of SEQ ID NO:8 and/or SEQ ID NO:10). In some embodiments, a lymphodepletion regimen further comprises administering Mensa (sodium-2-mercaptoethanesolfonate). In some embodiments, a lymphodepletion regimen further comprises administering at least one corticosteroid. In some embodiments, the corticosteroid is administered immediately prior to administration of an anti-CD52 antibody (e.g., an antibody comprising the sequence of SEQ ID NO:8 and/or SEQ ID NO:10). In some embodiments, the corticosteroid is methylprednisolone administered at a dose of 1-5 mg/kg (e.g., 2 mg/kg). In some embodiments, the corticosteroid is administered at least two days prior to administration of CAR-T cells. In some embodiments, no corticosteroid is administered for at least two days prior to the administration of CAR-T cells.

In some embodiments, a patient receives a premedication for infusion-related reaction prior to the lymphodepletion regimen. The premedication may comprise, for example, an antihistamine or acetaminophen.

In some embodiments, the components of the lymphodepletion regimen of fludarabine/cyclophosphamide (FC) or fludarabine/cyclophosphamide/anti-CD52 antibody (FCA) are administered simultaneously; in other embodiments, the components are administered serially. In some embodiments, the subject receives a FC regimen prior to the first dose of the CAR-T cell therapy; and a FCA regimen prior to a redosing of the CAR-T cell therapy. In some embodiments, the subject receives a FCA regimen prior to the first dose of the CAR-T cell therapy; and a second FCA regimen prior to a redosing of the CAR-T cell therapy. In some embodiments, the subject receives a FC regimen prior to the first dose of the CAR-T cell therapy, and a CD52 antibody (e.g., an antibody comprising the sequence of SEQ ID NO:8 and/or SEQ ID NO:10) after the first dose of the CAR-T cell therapy. In some embodiments, the subject receives a FC regimen prior to the first dose of the CAR-T cell therapy, and a CD52 antibody (e.g., an antibody comprising the sequence of SEQ ID NO:8 and/or SEQ ID NO:10) after the first dose of the CAR-T cell therapy; and the subject further receives a FC regimen prior to the second/subsequent dose of the CAR-T cell therapy, and a CD52 antibody (e.g., an antibody comprising the sequence of SEQ ID NO:8 and/or SEQ ID NO:10) after the second/subsequent dose of the CAR-T cell therapy.

In some embodiments, the methods further include administering an agent to debulk the disease prior to administration of the first dose and/or prior to the administration of the second/subsequent dose. In some embodiments, the methods include administering a chemotherapeutic agent prior to the first dose and/or prior to the administration of the second/subsequent dose. In some embodiments, the subject has been previously treated with a chemotherapeutic agent prior to the first dose. In some embodiments, the chemotherapeutic agent is or comprises a conditioning chemotherapy, which reduces burden of the disease in the subject prior to the first dose and/or subsequent dose. In some embodiments, the administration of the chemotherapeutic agent includes administration of a chemotherapeutic agent prior to the administration of the first dose and optionally not prior to the administration of the second/subsequent dose. In some embodiments, the chemotherapeutic agent is administered between 2 and 10 days prior to the administration of the first dose. In some embodiments, the chemotherapeutic agent is administered between 2 and 10 days prior to the administration of the second/subsequent dose. In some embodiments, the chemotherapeutic agent is administered between 2 and 10 days prior to the administration first dose and between 2 and 14 days prior to the administration of the second/subsequent dose.

Also provided are cells and compositions for use and uses of allogeneic CAR-T cells and compositions for treating a disease in a subject, such as a tumor or cancer. Also provided are cells and compositions for use and uses of allogeneic CAR-T cells and compositions for the manufacture of a medicament for treatment of a disease in a subject previously treated with allogeneic CAR-T cells. In some embodiments, the compositions or cells for use or medical uses are for use 4 to 24 weeks after the previous treatment. In some embodiments, the compositions or cells for use are formulated for administration of a subsequent dose in an amount sufficient for reduction in burden of a disease in the subject having been previously treated with the CAR-T cells. In some embodiments, the CAR-T cells are CD19-specific CAR-T cells (e.g., UCART19).

In some embodiments of such medical uses, the compositions or cells are for use that includes administering to a subject having the disease a first dose of allogeneic CAR-T cells. In some embodiments, the first dose contains about $1 \times 10^6$ total cells, about $6 \times 10^6$ total cells, or about $1 \times 10^7$ total cells. In some embodiments, the compositions or cells are for use that includes administering to the subject a subsequent dose of allogeneic CAR-T cells at a time point that is at least or more than about 4 weeks after and less than about 24 weeks after initiation of the administration of the first dose.

In some embodiments, allogeneic CAR-T cells are provided for use in methods of treating a disease in a subject previously treated with allogeneic CAR-T cells. In some embodiments, the cells are for use between about 4 and 24 weeks after the previous treatment. In some embodiments, the cells for use are formulated for administration of a subsequent dose in an amount sufficient for reduction in burden of a disease in the subject having been previously treated with the allogeneic CAR-T cells. In some embodiments, the CAR-T cells are CD19-specific CAR-T cells (e.g., UCART19).

In some embodiments of any such compositions or cells for use or medical uses, the subject does not exhibit morphologic disease and/or the subject does not exhibit greater than 5% blast cells in the bone marrow.

In some embodiments, the compositions or cells are for use in a method including administering to a subject having the disease a first dose of allogeneic CAR-T cells. In some embodiments, the first dose about $6 \times 10^5$ cells, about $6 \times 10^6$ cells, about $6 \times 10^7$ cells, about $8 \times 10^7$ cells, about $1.8 \times 10^8$ cells, or about $2.4 \times 10^8$ cells. In some embodiments, the cells are for use in a method that includes administering to the subject a subsequent dose of allogeneic CAR-T cells at a time point that is at least or more than about 5 weeks after and less than about 24 weeks after initiation of said administration of the first dose.

Also provided herein are uses of allogeneic CAR-T cells for manufacture of a medicament for the treatment of a disease in a subject includes cells that are formulated and/or packaged for administration to the subject in a first and a subsequent dose. In some embodiments, the treatment includes administering the cells to the subject in a first and a subsequent dose, where the first dose includes about $6 \times 10^5$ cells, about $6 \times 10^6$ cells, about $6 \times 10^7$ cells, about $8 \times 10^7$ cells, about $1.8 \times 10^8$ cells, or about $2.4 \times 10^8$ cells. In some embodiments, the CAR-T cells are CD19-specific CAR-T cells (e.g., UCART19).

In some embodiments, the cells for use are formulated and/or packaged for administration to the subject in a first and a subsequent dose and/or the treatment includes administering the cells to the subject in a first and a subsequent dose. In some embodiments, the first dose contains about $6 \times 10^5$ cells, about $6 \times 10^6$ cells, about $6 \times 10^7$ cells, about $8 \times 10^7$ cells, about $1.8 \times 10^8$ cells, or about $2.4 \times 10^8$ cells.

In some embodiments, the use includes where the first and subsequent administrations include administering the cells in one or more unit dose, each unit dose comprising about $6 \times 10^5$ cells, about $6 \times 10^6$ cells, about $6 \times 10^7$ cells, about $8 \times 10^7$ cells, about $1.8 \times 10^8$ cells, or about $2.4 \times 10^8$ cells.

In some embodiments, the cells or use includes where the first administration comprises administering a single unit dose. In some embodiments, the cells or use includes where the subsequent administration comprises administration of two or more unit doses. In some embodiments, the cells or use includes where the subsequent administration comprises administration a single unit dose.

In some embodiments, a use of the cells is provided for treating a disease, wherein the disease is a tumor or a cancer. In some embodiments the disease is a lymphoid malignancy such as for example without limitation, acute and chronic leukemias, lymphomas, multiple myelomas, a myeloid malignancy (e.g., leukemias, myelodysplastic syndromes, myelodysplastic/myeloproliferative neoplasms), or a mixed lineage malignancy. In some embodiments, a composition or cells are provided for use in treating acute lymphoblastic leukemia (ALL). In some embodiments, the ALL is relapsed/refractory ALL. In some embodiments, a composition or cells are provided for use in treating Non-Hodgkin's lymphoma, such relapsed or refractory Non-Hodgkin's lymphoma. In some embodiments, a composition or cells are for use in treating relapsed or refractory large B-cell or follicular lymphoma.

In some embodiments, the cells, composition, or use includes where the subsequent dose is formulated for administration of about the same number of allogeneic CAR-T cells as the allogeneic CD19-specific CAR-T cells in the previous dose. In some embodiments, the composition containing the cells of the subsequent dose is formulated for administration of an increased number of allogeneic CAR-T cells as compared to the first dose or previous dose. In some embodiments, the cells, composition, or use includes where the subsequent dose is formulated for administration of less than the number of allogeneic CAR-T cells as the allogeneic CD19-specific CAR-T cells in the previous dose.

Also provided are pharmaceutical kits for treating a patient suffering from a disease such as cancer, the kit comprising CAR-T cells and a CD52 antibody. In some embodiments, the CAR-T cells are CD19 specific CAR-T cells, such as UCART19 cells. In some embodiments, the CAR-T cells express the CAR of SEQ ID NO:1. In some embodiments, the CD52 antibody comprises the sequence of SEQ ID NO:8 and/or SEQ ID NO:10. In some embodiments, the kit comprises a first container comprising the CAR-T cells, and a second container comprising the CD52 antibody. In some embodiments, at least one of the first and the second container is a flexible cell infusion bag. In some embodiments, the kit further comprises a label or package insert comprising instructions for administering the CAR-T cells and the CD52 antibody to the subject.

Also provided are articles of manufacture for carrying out the methods. In some embodiments, the article of manufacture includes a plurality of containers, e.g., sealable containers, each individually comprising a unit dose of allogeneic CAR-T cells, for administration to the subject, packaging material, and/or a label or package insert. In some embodiments, the CAR-T cells are CD19-specific CAR-T cells (e.g., UCART19).

In some embodiments, the unit dose comprises the amount of cells to be given in the lowest dose in the methods, such as the size of the first dose. In some embodiments, the unit dose includes about $6\times10^5$ cells, about $6\times10^6$ cells, about $6\times10^7$ cells, about $8\times10^7$ cells, about $1.8\times10^8$ cells, or about $2.4\times10^8$ cells.

In some embodiments, the label or package insert includes instructions for administering a plurality of the unit doses to the subject, for example, by administering a certain number of such unit doses, e.g., one unit dose, in administration of a first dose, and then administering a subsequent dose including one or a plurality of the unit doses. In some embodiments, the instructions specify carrying out a first administration, said first administration comprising delivering one of said unit doses to the subject, and carrying out a subsequent administration, said subsequent administration comprising administering one or a plurality of said unit doses to the subject. In some embodiments, they specify that the subsequent administration is to be carried out at a time between about 5 and about 24 weeks following said first administration. In some embodiments, the containers are or comprise flexible cell infusion bags. In some embodiments, the methods are for allogeneic administration. In some embodiments, the label and/or packaging material further includes an identifier specific to the subject, indicating that the cells were derived from the subject and/or should be administered to the subject specifically. In some embodiments, the CAR-T cells are CD19-specific CAR-T cells (e.g., UCART19).

Also provided is a method of producing a population of allogeneic chimeric antigen receptor (CAR)-T cells (CAR-T cells) directed to a target of interest comprising: (a) isolating peripheral blood mononuclear cells (PBMCs) from a healthy donor; (b) activating the T-cells in the PBMCs; (c) transducing the activated T-cells with a lentiviral vector, wherein the lentiviral vector is a self-inactivating recombinant vector expressing a CAR of interest; (d) disrupting TCRαβ and CD-52 gene expression in a subset of the T-cells; (e) expanding the population of T-cells; and (f) enriching the population of T-cells for TCRαβ-negative cells; whereby generating a population of "off the shelf" allogeneic chimeric antigen receptor (CAR)-T cells (CAR-T cells). In some embodiments, the CAR-T cells comprise allogeneic CD19CAR/RQR8+_TCRαβ-_T-cells.

Also provided are allogeneic chimeric antigen receptor (CAR)-T cells (CAR-T cells) comprising an anti-human CD19 4-1BB/CD3zeta CAR, for use in a method of treating a subject who has refractory and/or relapsed Non-Hodgkin's Lymphoma, the method comprising administering to the subject at least one dose of the CAR-T cells, wherein the at least one dose is about $20\times10^6$ cells/dose to about $360\times10^6$ cells/dose.

Also provided are chimeric antigen receptor (CAR)-T cells (CAR-T cells) for use in a method of treatment comprising: (a) administering to a subject a first dose of the CAR-T cells, and (b) administering to the subject a subsequent dose of CAR-T cells at a time point that is at least or more than about 28 days after and less than about 200 days after initiation of said administration in (a).

Also provided are allogeneic chimeric antigen receptor (CAR)-T cells, for use in a method of treatment comprising administering a subsequent dose of the allogeneic CAR-T cells to a subject previously administered a first dose of allogeneic CAR-T cells, wherein: the subsequent dose of cells is administered at a time point that is at least or more than about 5 weeks after and less than about 24 weeks after initiation of the first dose. Optionally wherein, at the time of administration, the subject does not exhibit a detectable adaptive host immune response specific for the CAR-T cells.

Also provided are allogeneic chimeric antigen receptor (CAR)-T cells, for use in a method of treatment comprising administering to a subject a subsequent dose of the allogeneic chimeric antigen receptor (CAR)-T cells, wherein: prior to said administration, the subject has received a previous dose of the CAR-T cells in an amount sufficient to demonstrate clinical benefit in the subject; and at the time of administration, the subject does not exhibit a detectable adaptive host immune response specific for the CAR-T cells;

and/or the time between said previous and subsequent doses is greater than about 5 weeks and less than about 24 weeks.

Also provided are allogeneic chimeric antigen receptor (CAR)-T cells (CAR-T cells) comprising an anti-human CD19 4-1BB/CD3zeta CAR, for use in a method of treating an adult subject who has refractory and/or relapsed CD19+ B-cell acute lymphoblastic leukemia, wherein the method comprises administering to the subject at least one dose of the CAR-T cells, wherein the at least one dose is selected from the group consisting of about $6\times10^5$ cell/dose, $6\times10^6$ cells/dose, about $6\text{-}8\times10^7$ cells/dose, and about $1.8\text{-}2.4\times10^8$ cells/dose.

Also provided are allogeneic chimeric antigen receptor (CAR)-T cells (CAR-T cells) comprising an anti-human CD19 4-1BB/CD3zeta CAR, for use in a method of treating a pediatric subject who has refractory and/or relapsed CD19+ B-cell acute lymphoblastic leukemia, comprising administering to the subject at least one dose of the CAR-T cells comprising an anti-human CD19 4-1BB/CD3zeta CAR, wherein the at least one dose is about $2\text{-}8\times10^7$ cells/dose.

Also provided are allogeneic chimeric antigen receptor (CAR)-T cells for use in treating a disease in a subject previously treated with the CAR-T cells, wherein: the cells are for use between about 5 and 24 weeks after the previous treatment; and the cells are formulated for administration of a subsequent dose in an amount sufficient for amelioration of a disease in the subject having been previously treated with the CAR-T cells.

In some embodiments, the methods of treatment disclosed herein are applied to subjects who have been treated with an antibody for the depletion of CD52+ cells (e.g. an antibody comprising SEQ ID NO:8 and SEQ ID NO:10), or who will be treated with said antibody as part of said methods of treatment. These methods of treatment may comprise the use of a CAR-T cell (e.g. UCART19) deficient in CD52.

Also provided are methods of producing a population of allogeneic chimeric antigen receptor (CAR)-T cells (CAR-T cells) directed to a target of interest comprising:

(a) providing isolated peripheral blood mononuclear cells (PBMCs) from a healthy donor;

(b) activating the T-cells in the PBMCs;

(c) transducing the activated T-cells with a lentiviral vector, wherein the lentiviral vector is a self-inactivating recombinant vector expressing a CAR of interest;

(d) disrupting TCRαβ and CD-52 gene expression in a subset of the T-cells;

(e) expanding the population of T-cells; and (f) enriching the population of T-cells for TCRαβ-negative cells;

whereby generating a population of allogeneic chimeric antigen receptor (CAR)-T cells (CAR-T cells).

BRIEF DESCRIPTION OF THE DRAWINGS

FIG. 6A and FIG. 6B depict a study design for the use of an allogeneic anti-CD19 CAR-T cell product (UCART19) in adult patients with CD19+ relapsed/refractory B-cell acute lymphoblastic leukemia.

DETAILED DESCRIPTION

General Techniques

Figure 1:
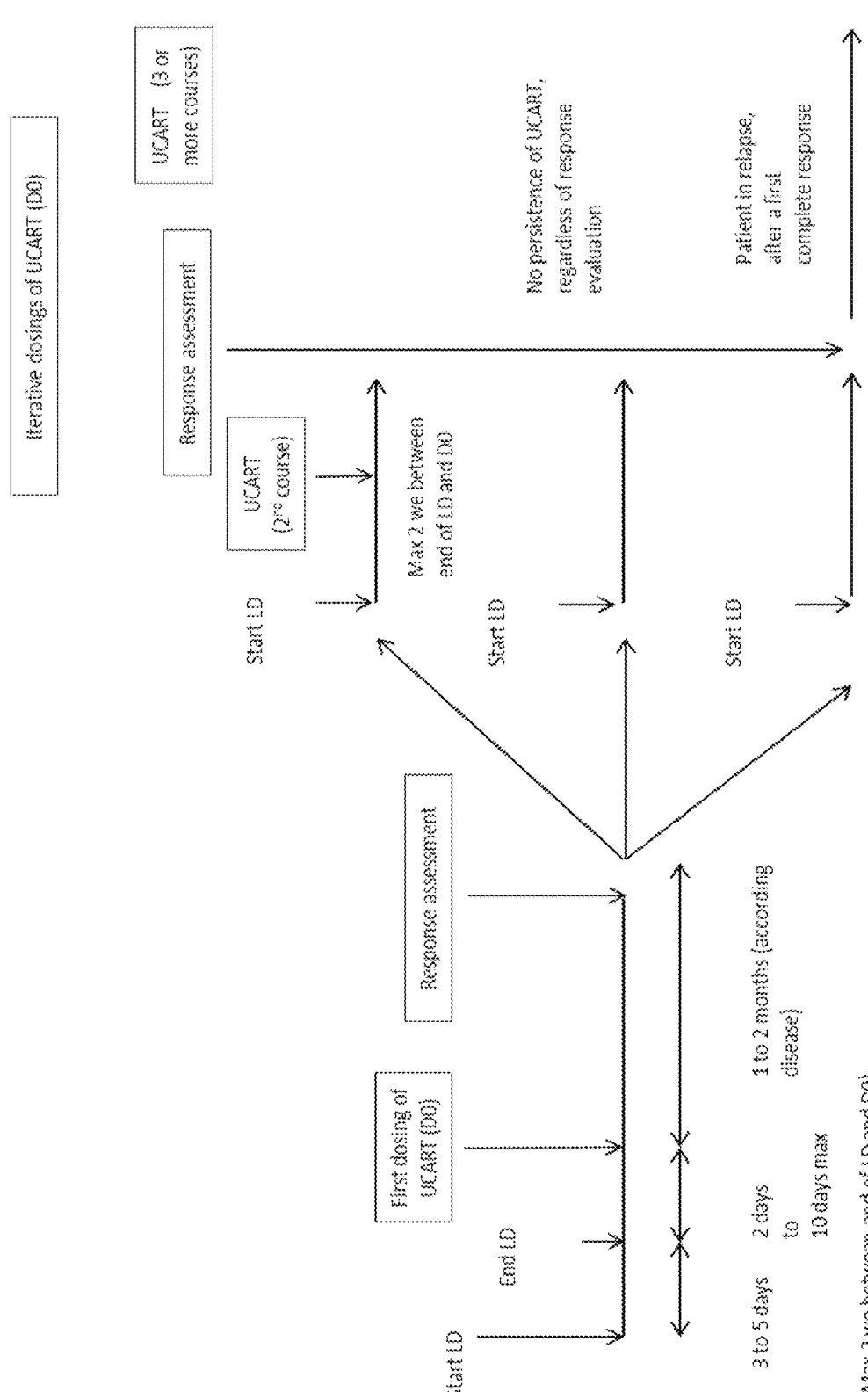
FIG. 1 depicts an exemplary schematic showing possible steps for a multiple dosing regimen for allogeneic CAR-T cell treatment.

The practice of the methods and compositions described in the instant disclosure generally employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

As used herein "allogeneic" means that cells or population of cells used for treating patients are not originating from said patient but from a donor, but not from a Human Leucocyte Antigen (HLA) compatible donor.

As used herein "autologous" means that cells, a cell line, or population of cells used for treating patients are originating from said patient or from a Human Leucocyte Antigen (HLA) compatible donor.

As used herein, "immune cell" refers to a cell of hematopoietic origin functionally involved in the initiation and/or execution of innate and/or adaptive immune response.

As used herein, "chimeric antigen receptor" or alternatively a "CAR" refers to a molecule which, when in an immune effector cell, provides the cell with specificity for a target and intracellular signal generation upon engagement with the target.

As used herein, the term "dosing regimen" refers to the total course of treatment administered to a patient, e.g., treatment with CAR-T cells.

As used herein, "treatment" is an approach for obtaining beneficial or desired clinical results. For purposes of this disclosure, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, remission of a disease (e.g., cancer), decreasing symptoms resulting from a disease (e.g., cancer), increasing the quality of life of those suffering from a disease (e.g., cancer), decreasing the dose of other medications required to treat a disease (e.g., cancer), delaying the progression of a disease (e.g., cancer), curing a disease (e.g., cancer), and/or prolonging survival of patients having a disease (e.g., cancer). "Reducing incidence" means any of reducing severity (which can include reducing need for and/or amount of (e.g., exposure to) other drugs and/or therapies generally used for this disease.

"Ameliorating" or "amelioration of" means a lessening or improvement of one or more symptoms as compared to not administering a treatment. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. An effective dosage can be administered in one or more administrations. For purposes of this disclosure, an effective dosage of drug, CAR-T cell, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, e.g. a human. Mammals also include, but are not limited to, farm animals, sport animals, pets, primates, horses, dogs, cats, mice and rats.

"Refractory" as used herein refers to a disease (e.g., cancer) that does not respond to a treatment. In embodiments, a refractory cancer can be resistant to a treatment before or at the beginning of the treatment. In other embodiments, the refractory cancer can become resistant during a treatment. A refractory cancer is also referred to herein as a resistant cancer.

"Relapsed" as used herein refers to the return of a disease (e.g., cancer) or the signs and symptoms of a disease such as cancer after a period of improvement, e.g., after prior treatment of a therapy, e.g., cancer therapy.

As used herein "minimal residual disease" or "MRD" refers to low-level disease detected in a variety of clinical situations. In some embodiments, MRD refers to molecularly defined relapse after remission.

As used herein, "vector" means a construct, which is capable of delivering, and, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site including, for example without limitation, scFv, single domain antibodies (e.g., shark and camelid antibodies), maxibodies, minibodies, intrabodies, diabodies, triabodies, tetrabodies, v-NAR and bis-scFv (see, e.g., Hollinger and Hudson, 2005, Nature Biotechnology 23(9):1126-1136). An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody, as used herein, refers to one or more fragments of an intact antibody that retain the ability to specifically bind to a given antigen (e.g., at tumor antigen). Antigen binding functions of an antibody can be performed by fragments of an intact antibody. Examples of binding fragments encompassed within the term "antigen binding portion" of an antibody include Fab; Fab'; F(ab')₂; an Fd fragment consisting of the VH and CH1 domains; an Fv fragment consisting of the VL and VH domains of a single arm of an antibody; a single domain antibody (dAb) fragment (Ward et al., 1989, Nature 341:544-546), and an isolated complementarity determining region (CDR).

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The term "monoclonal antibody" (Mab) refers to an antibody that is derived from a single copy or clone, including e.g., any eukaryotic, prokaryotic, or phage clone, and not the method by which it is produced. In some embodiments, a monoclonal antibody of the disclosure exists in a homogeneous or substantially homogeneous population.

"Humanized" antibody refers to forms of non-human (e.g. murine) antibodies that are chimeric immunoglobulins, immunoglobulin chains, or fragments thereof (such as Fv, Fab, Fab', F(ab')₂ or other antigen-binding subsequences of antibodies) that contain minimal sequence derived from non-human immunoglobulin. Generally, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

As used herein, "human antibody" means an antibody having an amino acid sequence corresponding to that of an antibody that can be produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, wherein the phage library expresses human antibodies (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from a subject or may have been immunized in vitro). See, e.g., Cole et al. Monoclonal Antibodies and Cancer Therapy, Alan R. Liss, p. 77, 1985; Boerner et al., 1991, J. Immunol., 147 (1): 86-95; and U.S. Pat. No. 5,750,373.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, that contribute to the formation of the antigen binding site of antibodies. If variants of a subject variable region are desired, particularly with substitution in amino acid residues outside of a CDR region (i.e., in the framework region), appropriate amino acid substitution, often, conservative amino acid substitution, can be identified by comparing the subject variable region to the variable regions of other antibodies which contain CDR1 and CDR2 sequences in the same canonincal class as the subject variable region (Chothia and Lesk, J Mol Biol 196(4):901-917, 1987). When choosing FR to flank subject CDRs, e.g., when humanizing or optimizing an antibody, FRs from antibodies which contain CDR1 and CDR2 sequences in the same canonical class are preferred.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 21st Ed. Mack Publishing, 2005).

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the disclosure are described in terms of a Markush group or other grouping of alternatives, the disclosure encompasses not only the entire group listed as a whole, but each member of the group individually and all possible subgroups of the main group, but also the main group absent one or more of the group members. The disclosure also envisages the explicit exclusion of one or more of any of the claimed group members.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Unless otherwise defined, all technical and scientific terms used herein have the same meaning as commonly understood by one of ordinary skill in the art to which this disclosure belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the methods and compositions described herein. The materials, methods, and examples are illustrative only and not intended to be limiting.

Treatment with CAR-T Cells

Provided herein are methods, compositions, and articles of manufacture for use in cell therapy, for the treatment of diseases including various cancers and tumors. The methods involve administering allogeneic chimeric antigen receptor (CAR)-T cells which specifically bind to antigens associated with the disease and result in a response, such as an immune response against such molecules upon binding to such antigens.

The methods may be used for treatment of, e.g., hematological neoplasms (WHO classification, 2008) and solid tumors. Hematological neoplasms include, e.g., lymphoid malignancies (acute and chronic leukemias, lymphomas, multiple myelomas), myeloid malignancies (leukemias, myelodysplastic syndromes, myelodysplastic or myeloproliferative neoplasms), and mixed lineage malignancies. Solid tumors include, e.g., solid tumors expressing antigen(s) targeted by the CAR-T cells used in treatment.

The methods are suitable for treatment of adults and pediatric population, including all subsets of age, and can be used as any line of treatment, including first line or subsequent lines.

In some embodiments, the disease is a tumor. In some embodiments, it is a cancer, malignancy, neoplasm, or other proliferative disease or disorder, such as leukemia, lymphoma, e.g., chronic lymphocytic leukemia (CLL), ALL (e.g., relapsed/refractory ALL), non-Hodgkin's lymphoma, acute myeloid leukemia, diffuse large B-cell lymphoma (DLBCL), multiple myeloma, refractory follicular lymphoma, mantle cell lymphoma, indolent B cell lymphoma, B cell malignancies, cancers of the colon, lung (e.g., small and non-small cell lung cancer), liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, head and neck squamous cell carcinoma (HNSCC), and/or mesothelioma. In some embodiments, the disease is a leukemia or lymphoma. In some embodiments, the disease is acute lymphoblastic leukemia. In some embodiments, the disease is relapsed or refractory acute lymphoblastic leukemia. In some embodiments, the disease is non-Hodgkin lymphoma (NHL).

In some embodiments the disease is acute lymphoblastic leukemia (ALL). In some embodiments the disease is pediatric acute lymphoblastic leukemia (ALL).

In some embodiments the disease is an advanced lymphoid malignancy such as B-cell acute lymphoblastic leukemia (B-ALL). In some embodiments, the disease is refractory B-ALL, e.g. adult refractory B-ALL. In some embodiments, the disease is relapsed B-ALL, e.g. adult relapsed B-ALL.

In some embodiments, the disease is Non-Hodgkin's lymphoma, such as large B-cell and/or follicular lymphoma. The large B-cell lymphoma may be a large B-cell lymphoma as diagnosed using histological or cytological methods according to the 2018 WHO revision of lymphoma classification: diffuse large B-cell lymphoma (DLBCL)-not-otherwise specified (NOS) (germinal center B-cell [GCB], and non-GCB), DLBCL coexistent with follicular lymphoma of any grade, intravascular large B-cell lymphoma, DLBCL associated with chronic inflammation, anaplastic lymphoma kinase positive (ALK+) DLBCL, Epstein-Barr virus positive (EBV+) DLBCL-NOS, T cell/histiocyte-rich large B cell lymphoma, DLBCL with IRF4/MUM1 rearrangement, high-grade B cell lymphomas with translocation of MYC and BCL2 and/or BCL6 (double/triple hit), primary cutaneous DLBCL-leg type, transformation of follicular lymphoma to DLBCL, primary mediastinal B-cell lymphoma (PMBCL); or follicular lymphoma. Parameters to be considered for treatment include, e.g., kinetics parameters of the CAR-T administered, disease evaluation (adapted to disease targeted), and the subjects' health status.

Methods of treatment may comprise several stages including lymphodepletion (optionally, with premedication), treatment, and optional retreatment.

Lymphodepletion

In some embodiments, a lymphodepletion (LD) regimen is administered to the subject prior to a first and/or subsequent dose of CAR-T cells. In some embodiments, the lymphodepletion regimen is administered to the subject concurrently with a first and/or subsequent dose of CAR-T cells. In some embodiments, the lymphodepletion regimen is administered before, during, and/or after a first and/or subsequent dose of CAR-T cells.

Suitable LD regimens are described herein and/or known in the art. In some embodiments, LD starts prior to, concurrently with, or after a CAR-T infusion. Doses and timing of LD administration may be adapted with regard to the first or subsequent dosings of CAR-T. In some embodiments, the duration of LD is about 3 to 5 days. In some embodiments, a time window between the end of LD and start of CAR-T administration is between about of 2 days to about 2 weeks. In some embodiments, LD is initiated about 15 to 7 days prior to administration of a dose of CAR-T cells. In some embodiments, LD is initiated about 19 to 5 days prior to administration of a dose of CAR-T cells. In some embodiments, LD is initiated about 3, 4, 5, 6, 7, 8, 9, 10, 11, 12, 13, 14, 15, 16, 17, 18, 19, or 20 days prior to administration of a dose of CAR-T cells. In some embodiments, duration of a LD regimen is about 1, 2, 3, 4, 5, 6, 7, 8, 9, 10, 11, 12, 13, or 14 days. In some embodiments, a dose of CAR-T cells is administered about 1, 2, 3, 4, 5, 6, 7, 8, 9, 10, 11, 12, 13, or 14 days after the end of LD.

In some embodiments, a LD regimen comprises administration of one or more chemotherapeutic drugs.

In some embodiments, a LD regimen comprises administration of anti-CD52 antibody, such as an antibody that recognizes the human cluster of differentiation (CD) 52 antigen, a cell surface glycoprotein expressed on most lymphoid cells. As used herein a CD52 monoclonal antibody is one that is directed against the 21-28 kD cell surface glycoprotein CD52. CD52 is an abundant molecule (approximately $5 \times 10^5$ antibody binding sites per cell) present on at least 95% of all human peripheral blood lymphocytes and monocytes/macrophages. Exemplary CD52 antibodies for use in the methods and compositions described herein include, for example, alemtuzumab. In some embodiments, a CD52 antibody comprises the HCDR1, HCDR2, HCDR3, LCDR1, LCDR2, and LCDR3 sequences as shown in Table 1 below.

TABLE 1

Exemplary CD52 antibody CDR sequences

| CDR | Sequence (SEQ ID NO) |
|---|---|
| HCDR1 | DFYMN (SEQ ID NO: 2) |
| HCDR2 | FIRDKAKGYTTEYNPSVKG (SEQ ID NO: 3) |
| HCDR3 | EGHTAAPFDY (SEQ ID NO: 4) |
| LCDR1 | KASQNIDKYLN (SEQ ID NO: 5) |
| LCDR2 | NTNNLQT (SEQ ID NO: 6) |
| LCDR3 | LQHISRPRT (SEQ ID NO: 7) |

In some embodiments, a CD52 antibody comprises a VH and/or a VL comprising the sequences shown in Table 2 below.

TABLE 2

Exemplary CD52 Antibody VH and VL sequences

| Description | Amino Acid Sequence | SEQ ID NO | DNA Sequence | SEQ ID NO |
|---|---|---|---|---|
| VH | QVQLQESGPGLVRPS QTLSLTCTVSGFTFT DFYMNWVRQPPGRGL EWIGFIRDKAKGYTT EYNPSVKGRVTMLVD TSKNQFSLRLSSVTA ADTAVYYCAREGHTA APFDYWGQGSLVTVS SASTKGPSVFPLAPS SKSTSGGTAALGCLV | 8 | caagtgcagcttcaa gaatccggccctggt ctggtccgcccctcc caaaccctctccctg acatgcaccgtgtcg ggattcacctttacc gatttctacatgaac tgggtccggcagccg cccggaagaggtctg gagtggatcggcttc | 9 |

TABLE 2-continued

Exemplary CD52 Antibody VH and VL sequences

| Description | Amino Acid Sequence | SEQ ID NO | DNA Sequence | SEQ ID NO |
|---|---|---|---|---|
| | KDYFPEPVTVSWNSG ALTSGVHTFPAVLQS SGLYSLSSVVTVPSS SLGTQTYICNVNHKP SNTKVDKKVEPKSCD KTHTCPPCPAPELLG GPSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVYTLPPSRD ELTKNQVSLTCLVKG FYPSDIAVEWESNG QPENNYKTTPPVLDS DGSFFLYSKLTVDKS RWQQGNVFSCSVMHE ALHNHYTQKSLSLSP GK | | attcgggacaaagcc aaggggtacaccacc gagtacaacccgtcc gtgaagggacgcgtg actatgctcgtggac acgtccaagaaccag ttcagcttgaggctg agcagcgtgactgcc gcggataccgcagtg tactactgtgcccgg gaagggcacactgcc gctccattcgactat tggggccagggatca ctggtcactgtgtcg tccgcctccaccaag ggcccatcggtcttc cccctggcaccctcc tccaagagcacctct ggggggcacagcggcc ctgggctgcctggtc aaggactacttcccc gaaccggtgacggtg tcgtggaactcaggc gccctgaccagcggc gtgcacaccttcccg gctgtcctacagtcc tcaggactctactcc ctcagcagcgtagtg accgtgccctccagc agcttgggcacccag acctacatctgcaac gtgaatcacaagccc agcaacaccaagggg acaagaaagttgagc ccaaatcttgtgaca aaactcacacatgcc caccgtgcccagcac ctgaactcctggggg gaccgtcagtcttcc tcttccccccaaaac ccaaggacaccctca tgatctcccggaccc ctgaggtcacatgcg tggtggtggacgtga gccacgaagaccctg aggtcaagttcaact ggtacgtggacggcg tggaggtgcataatg ccaagacaaagccgc gggaggagcagtaca acagcacgtaccgtg tggtcagcgtcctca ccgtcctgcaccagg actggctgaatggca aggagtacaagtgca aggtctccaacaaag ccctcccagcccca tcgagaaaaccatct ccaaagccaaagggc agccccgagaaccac aggtgtacaccctgc ccccatcccgggacg agctgaccaagaacc aggtcagcctgacct gcctggtcaaaggct tctatcccagcgaca tcgccgtggagtggg agagcaatgggcagc cggagaacaactaca agaccacgcctcccg tgctggactccgacg gctccttcttcctct atagcaagctcaccg tggacaagagcaggt |

TABLE 2-continued

Exemplary CD52 Antibody VH and VL sequences

| Descrip-tion | Amino Acid Sequence | SEQ ID NO | DNA Sequence | SEQ ID NO |
|---|---|---|---|---|
| | | | ggcagcaggggaacg tcttctcatgctccg tgatgcatgaggctc tgcacaaccactaca cgcagaagagcctct ccctgtctccgggaa aa | |
| VL | DIQMTQSPSSLSASV GDRVTITCKASQNID KYLNWYQQKPGKAPK LLIYNTNNLQTGVPS RFSGSGSGTDFTFTI SSLQPEDIATYYCLQ HISRPRTFGQGTKVE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC | 10 | atgggatggagctgt atcatcctcttcttg gtagcaacagctaca ggcgtgcactccgac atccaaatgacccaa tccccatcctcactt tccgcctccgtgggc gaccgcgtgactatt acctgtaaagcgtca cagaatatcgacaag tacctgaactggtac cagcagaagcctgga aaggcccccaagctc ctgatctacaacacc aacaacttgcagact ggagtgccgagcaga ttttccggctccggc tcggggactgatttc accttcaccatctcg agcctgcagccggag gatattgctacctat tactgcctgcaacac attagccggcccagg acgttcggacagggt accaaggtcgaaatc aagcgtacggtggct gcaccatctgtcttc atcttcccgccatct gatgagcagttgaaa tctggaactgcctct gttgtgtgcctgctg aataacttctatccc agagaggccaaagta cagtggaaggtggat aacgccctccaatcg ggtaactcccaggag agtgtcacagagcag gacagcaaggacagc acctacagcctcagc agcaccctgacgctg agcaaagcagactac gagaaacacaaagtc tacgcctgcgaagtc acccatcagggcctg agctcgcccgtcaca aagagcttcaacagg ggagagtgt | 11 |

In some embodiments, a CD52 antibody comprises a VH having the sequence of SEQ ID NO:8, or a sequence having at least 90%, at least 91%, at least 92%, at least 93%, at least 94%, at least 95%, at least 96%, at least 97%, at least 98%, or at least 99% sequence identity to SEQ ID NO:8. In some embodiments, a CD52 antibody comprises a VL having the sequence of SEQ ID NO:10, or a sequence having at least 90%, at least 91%, at least 92%, at least 93%, at least 94%, at least 95%, at least 96%, at least 97%, at least 98%, or at least 99% sequence identity to SEQ ID NO:10. In some embodiments, a CD52 antibody comprises a VH having the sequence of SEQ ID NO:8 and a VL having the sequence of SEQ ID NO:10. In some embodiments, a CD52 antibody comprises a VH encoded by the DNA sequence of SEQ ID NO:9 and a VL encoded by the DNA sequence of SEQ ID NO:11.

In some embodiments, the anti-CD52 antibody is a recombinant humanized IgG1 kappa monoclonal antibody (mAb). In some embodiments, the anti-CD52 antibody is alemtuzumab. Alemtuzumab is a recombinant DNA-derived humanized monoclonal antibody directed against the 21-28 kD cell surface glycoprotein, CD52. See, e.g., Saif et al., *Pediatr Transplant* 2015 March; 19(2):211-8. In some embodiments the anti-CD52 antibody comprises one or more CDR sequences isolated or derived from the CDRs of alemtuzumab. In some embodiments, the anti-CD52 antibody comprises the sequence of SEQ ID NO:8, or a sequence having at least 90%, at least 91%, at least 92%, at least 93%, at least 94%, at least 95%, at least 96%, at least 97%, at least 98%, or at least 99% sequence identity to SEQ ID NO:8. In some embodiments, the anti-CD52 antibody comprises the sequence of SEQ ID NO:10, or a sequence having at least 90%, at least 91%, at least 92%, at least 93%, at least 94%, at least 95%, at least 96%, at least 97%, at least 98%, or at least 99% sequence identity to SEQ ID NO:10. In some embodiments, the anti-CD52 antibody comprises an HCDR1 comprising the sequence of SEQ ID NO:2, a HCDR2 comprising the sequence of SEQ ID NO:3, a HCDR3 comprising the sequence of SEQ ID NO:4, a LCDR1 comprising the sequence of SEQ ID NO:5, a LCDR1 comprising the sequence of SEQ ID NO:6, and/or a LCDR3 comprising the sequence of SEQ ID NO:7. In some embodiments, the anti-CD52 antibody comprises an HCDR1 comprising the sequence of SEQ ID NO:2, a HCDR2 comprising the sequence of SEQ ID NO:3, a HCDR3 comprising the sequence of SEQ ID NO:4, a LCDR1 comprising the sequence of SEQ ID NO:5, a LCDR1 comprising the sequence of SEQ ID NO:6, and a LCDR3 comprising the sequence of SEQ ID NO:7; wherein the anti-CD52 antibody comprises the sequence of SEQ ID NO:8 and/or SEQ ID NO:10, or a sequence having at least 90%, at least 91%, at least 92%, at least 93%, at least 94%, at least 95%, at least 96%, at least 97%, at least 98%, or at least 99% sequence identity to SEQ ID NO:8 and/or SEQ ID NO:10.

In some embodiments, LD comprises administration of a combination of therapies. In some embodiments, the combination includes: fludarabine (range total dose about 90 to 150 mg/m$^2$) and cyclophosphamide (range total dose about 1000 to 4000 mg/m$^2$), with or without an anti-CD52 drug (e.g., an anti-CD52 antibody such as an antibody comprising the sequence of SEQ ID NO:8 and/or SEQ ID NO:10) (total dose from about 0.3 to about 1 mg/kg, or a flat dose of from about 30 mg to about 40 mg, from about 25 to about 60 mg, or from about 100 mg to about 120 mg). In some embodiments, the combination includes: fludarabine (about 30 mg/m$^2$) and cyclophosphamide (range total dose about 500 to 600 mg/m$^2$), with or without an anti-CD52 drug (e.g., CD52 antibody) (total dose from about 0.3 to about 1 mg/kg, or a flat dose of from about 30 mg to about 40 mg, from about 25 to about 60 mg, or from about 100 mg to about 120 mg). In some embodiments, the combination includes: fludarabine (about 30 mg/m$^2$) and cyclophosphamide (about 300 mg/m$^2$), with or without an anti-CD52 drug (e.g., CD52 antibody) (total dose from about 0.3 to about 1 mg/kg, or a flat dose of from about 30 mg to about 40 mg, from about 25 mg to about 60 mg, or from about 100 mg to about 120 mg). In some embodiments the combination includes: fludarabine (about 90 mg/m$^2$), cyclophosphamide (about 1500 mg/m$^2$) and with or without an anti-CD52 drug (e.g. anti- CD52 antibody, about 1 mg/kg). In some embodiments the combination includes: fludarabine (about 150 g/m$^2$) and cyclophosphamide (about 130 mg/kg), with or without an anti-CD52 drug (e.g. anti-CD52 antibody, total dose from about 0.3 to about 1 mg/kg, or a flat dose of from about 30 mg to about 40 mg, from about 25 to about 60 mg, or from about 100 mg to about 120 mg). In some embodiments the combination includes: fludarabine (about 150 g/m$^2$) and cyclophosphamide (about 120 mg/kg or about 130 mg/kg), with or without an anti-CD52 drug (e.g. an anti-CD52 antibody), total dose from about 0.3 to about 1 mg/kg, or a flat dose of from about 30 mg to about 40 mg, from about 25 to about 60 mg, or from about 100 mg to about 120 mg). In some embodiments, the combination includes: fludarabine (about 30 mg/m$^2$/day) and cyclophosphamide (about 300 mg/m$^2$/day), with or without an anti-CD52 drug (e.g. an anti-CD52 antibody, about 13 mg/day). In some embodiments, the combination includes: fludarabine (about 30 mg/m$^2$/day) and cyclophosphamide (about 300 mg/m$^2$/day), with or without an anti-CD52 drug (e.g. an anti-CD52 antibody, about 10 mg/day). In some embodiments, these above doses are administered during the course of one day. In some embodiments, these above doses are administered over multiple days.

In some embodiments, fludarabine and cyclophosphamide are administered on a first day, and the anti-CD52 antibody (e.g., an antibody comprising the sequence of SEQ ID NO:8 and/or SEQ ID NO:10) is administered on a second day. In some embodiments, fludarabine and cyclophosphamide are administered on a first day before administration of the CAR-T cells, and an anti-CD52 antibody (e.g., an antibody comprising the sequence of SEQ ID NO:8 and/or SEQ ID NO:10) is administered on a second day; wherein the second day is the same day that CAR-T cells are administered or the second day is after the CAR-T cells are administered. In some embodiments, fludarabine and cyclophosphamide are administered on a first day, CAR-T cells are administered on a second day, and an anti-CD52 antibody (e.g., an antibody comprising the sequence of SEQ ID NO:8 and/or SEQ ID NO:10) is administered at least about 1, about 2, about 3, about 4, about 5, about 6, about 7, about 8, about 9, about 10, about 11, or about 12 weeks after the second day. In some embodiments, fludarabine and cyclophosphamide are administered before administration of CAR-T cells, and an anti-CD52 antibody (e.g., an antibody comprising the sequence of SEQ ID NO:8 and/or SEQ ID NO:10) is administered at least about 1, about 2, about 3, about 4, about 5, about 6, about 7, about 8, about 9, about 10, about 11, or about 12 weeks after administration of the CAR-T cells.

In some embodiments, a lymphodepletion regimen comprises administration of fludarabine and cyclophosphamide (FC). In some embodiments, a lymphodepletion regimen comprises administration of fludarabine and anti-CD52 antibody (e.g., an antibody comprising the sequence of SEQ ID NO:8 and/or SEQ ID NO:10) (FA). In some embodiments, a lymphodepletion regimen comprises administration of cyclophosphamide and an anti-CD52 antibody (e.g., an antibody comprising the sequence of SEQ ID NO:8 and/or SEQ ID NO:10) (CA). In some embodiments, a lymphodepletion regimen comprises administration of fludarabine, cyclophosphamide, and an anti-CD52 antibody (e.g., an antibody comprising the sequence of SEQ ID NO:8 and/or SEQ ID NO:10) (FCA).

The choice of specific lymphodepletion regimen drugs and dose before a first or second/subsequent dose of CAR-T cells may be determined based on haematological analysis and hematologic recovery of the patient. In the case of redosing, a second lymphodepletion regimen can be more or less intense compared to a first lymphodepletion regimen (for example, based on recovery of lymphocytes, neutrophils, and viral reactivation after a first dose). For example, at the time of redosing, if lymphocyte and neutrophil levels are high, a strong or aggressive lymphodepletion regimen may be used. Alternatively, at the time of redosing, if lymphocyte levels are low, a weaker or less aggressive lymphodepletion regimen may be used. In some embodiments, if the number of blasts at the time of redosing is high, a strong or aggressive lymphodepletion regimen is used. In some embodiments, if the number of blasts at the time of redosing is low, a weaker or less aggressive lymphodepletion regimen is used.

In some embodiments, an increased intensity of LD regimen may be applied at the time of redosing (with or without anti-CD52 drug). In some embodiments, a reduced intensity of LD regimen may be applied, for example, in case of grade 3-4 lymphopenia at time of re-dosing (with or without anti-CD52 drug).

In some embodiments, the components of the lymphodepletion regimen of fludarabine/cyclophosphamide (FC) or fludarabine/cyclophosphamide/anti-CD52 antibody (FCA) are administered simultaneously; in other embodiments, the components are administered serially. In some embodiments, the subject receives a FC regimen prior to the first dose of the CAR-T cell therapy; and a FCA regimen prior to a redosing of the CAR-T cell therapy. In some embodiments, the subject receives a FCA regimen prior to the first dose of the CAR-T cell therapy; and a second FCA regimen prior to a redosing of the CAR-T cell therapy.

Exemplary LD regimens are provided in Tables 3A, 3B, 3C, 3D and 3E. In Tables 3A-3E, the timing indicated under Schedule is relative to the timing of administration of a dose of CAR-T cells (D0), in days. Negative numbers indicate days prior to administration of CAR-T cells (at D0).

TABLE 3A

| Lymphodepletion | Dose | Total dose | Schedule |
|---|---|---|---|
| Fludarabine | 30 mg/m$^2$/day | 90 mg/m$^2$ | D-7, D-6, D-5 |
| Cyclophosphamide | 500 mg/m$^2$/day | 1500 mg/m$^2$ | D-4, D-3, D-2 |
| Anti-CD52 antibody (optional) | 0.2 mg/kg/day | 1 mg/kg | D-7, D-6, D-5, D-4, D-3 |

TABLE 3B

| Lymphodepletion | Dose | Route | Schedule |
|---|---|---|---|
| Fludarabine | 30 mg/m$^2$/day | IV over 15-30 min | D-7, D-6, D-5 |
| Cyclophosphamide | 500 mg/m$^2$/day | IV over 1 hour | D-4, D-3, D-2 |
| Anti-CD52 antibody | 8 mg/day | IV | D-7, D-6, D-5, D-4, D-3 |

TABLE 3C

| Lymphodepletion | Dose | Route | Schedule |
|---|---|---|---|
| Fludarabine | 30 mg/m$^2$/day | IV over 15-30 min | D-7, D-6, D-5 |
| Cyclophosphamide | 500 mg/m$^2$/day | IV over 1 hour | D-4, D-3, D-2 |
| Anti-CD52 antibody | 6 mg/day | IV | D-7, D-6, D-5, D-4, D-3 |

TABLE 3D

| Lymphodepletion | Dose | Total dose | Schedule |
|---|---|---|---|
| Fludarabine | 30 mg/m²/day | 90 mg/m² | D-5, D-4, D-3 |
| Cyclophosphamide | 300 mg/m²/day | 900 mg/m² | D-5, D-4, D-3 |
| Anti-CD52 antibody (optional) | 13 mg/day | 39 mg | D-5, D-4, D-3 |

TABLE 3E

| Lymphodepletion | Dose | Total dose | Schedule |
|---|---|---|---|
| Fludarabine | 30 mg/m²/day | 90 mg/m² | D-5, D-4, D-3 |
| Cyclophosphamide | 300 mg/m²/day | 900 mg/m² | D-5, D-4, D-3 |
| Anti-CD52 antibody (optional) | 10 mg/day | 30 mg | D-5, D-4, D-3 |

In some embodiments, the LD regimen may further comprise treatment with Mensa (sodium 2-mercaptoethane-sulfonate).

Premedication

In some embodiments, the methods may comprise pre-medication for infusion-related reaction prior to the lymphodepletion regimen. In some embodiments, the methods may comprise a premedication administered before treatment with an anti-CD52 antibody. In some embodiments, the premedication may comprise treatment with high dose corticosteroids. For example, the premedication may comprise treatment with 2 mg/kg methylprednisolone. In some embodiments, the premedication is administered immediately before infusion with an anti-CD52 antibody. In some embodiments, the premedication is discontinued at least one or at least two days prior to any infusion of CAR-T cells (e.g., UCART19).

In some embodiments, the premedication may comprise treatment with one or more of an antihistamine, cimedidine, ranitidine, and acetaminophen. The antihistamine may be administered, for example, about 1 day, about 1 hour, or about 0.5 hour before administration of an anti-CD52 antibody (e.g., an antibody comprising the sequence of SEQ ID NO:8 and/or SEQ ID NO:10). The acetaminophen may be administered, for example, about 1 day, about 1 hour, or about 0.5 hour before administration of an anti-CD52 antibody (e.g., an antibody comprising the sequence of SEQ ID NO:8 and/or SEQ ID NO:10).

Treatment

In some embodiments, CAR-T cells are administered by intravenous infusion. In some embodiments, the intravenous infusion is over about 1 minute, about 3 minutes, about 5 minutes, about 10 minutes, about 30 minutes, about 1 hour, about 3 hours, about 6 hours, about 12 hours, or about 24 hours.

In some embodiments, a method of treating an adult subject who has refractory and/or relapsed CD19+ B-cell acute lymphoblastic leukemia comprises comprising administering to the subject at least one dose of allogeneic chimeric antigen receptor (CAR)-T cells (CAR-T cells) comprising an anti-human CD19 4-1BB/CD3zeta CAR, wherein the at least one dose is selected from the group consisting of about 6×10⁵ cell/dose, about 6×10⁶ cells/dose, about 6-8× 10⁷ cells/dose, and about 1.8-2.4×10⁸ cells/dose. In some embodiments, the CAR-T cells express the CAR of SEQ ID NO:1. In some embodiments, the CAR-T cells are UCART19(CD19)CAR/RQR8+_TCRαβ-_T-cells. In some embodiments, the CAR-T cells are CD-52 deficient. In some embodiments, the CAR-T cells are a mixture of CD52- deficient and CD52-positive cells. In some embodiments, the CAR-T cells express a safety switch, such as RQR8.

In some embodiments, a method of treating a pediatric subject who has refractory and/or relapsed CD19+ B-cell acute lymphoblastic leukemia comprises administering to the subject at least one dose of allogeneic chimeric antigen receptor (CAR)-T cells (CAR-T cells) comprising an anti-human CD19 4-1BB/CD3zeta CAR, wherein the at least one dose is about 2-8×10⁷ cells/dose. In some embodiments, the CAR-T cells express the CAR of SEQ ID NO:1. In some embodiments, the CAR-T cells are UCART19(CD19)CAR/RQR8+_TCRαβ-_T-cells. In some embodiments, the CAR-T cells are CD-52 deficient. In some embodiments, the CAR-T cells are a mixture of CD52-deficient and CD52-positive cells. In some embodiments, the CAR-T cells express a safety switch, such as RQR8.

In some embodiments, a method of treating a subject who has Non-Hodgkin's lymphoma (e.g., refractory and/or relapsed large B-cell lymphoma or follicular lymphoma) comprises administering to the subject at least one dose of allogeneic chimeric antigen receptor (CAR)-T cells (CAR-T cells) comprising (e.g., an anti-human CD19 4-1BB/CD3zeta CAR), wherein the at least one dose is about 20×10⁶ cells/dose to about 360×10⁶ cells/dose. In some embodiments, the at least one dose is selected from the group consisting of about 20×10⁶ cells/dose, about 40×10⁶ cells/dose, about 80×10⁶ cells/dose, about 120×10⁶ cells/dose, 240×10⁶ cells/dose, and about 360×10⁶ cells/dose. In some embodiments, the CAR-T cells express the CAR of SEQ ID NO:1. In some embodiments, the CAR-T cells are UCART19(CD19)CAR/RQR8+_TCRαβ-_T-cells. In some embodiments, the CAR-T cells are CD-52 deficient. In some embodiments, the CAR-T cells are a mixture of CD52-deficient and CD52-positive cells. In some embodiments, the CAR-T cells express a safety switch, such as the RQR8 safety switch described herein.

In some embodiments, CAR expression is detectable in the subject for up to at least 14 days or at least 28 days after administration of the CAR. In some embodiments, the subject exhibits a CR (complete response) or Cri (complete response with incomplete recovery of blood count) for at least 1 month, at least 1.3 month, at least 1.4 month, at least 1.6 month, at least 1.8 month, at least 2 months, at least 2.3 months, at least 1.4 month, at least 1.6 month, at least 1.8 month, at least 3 months, at least 3.3 months, at least 3.4 months, at least 3.6 months, at least 3.8 months, at least 6 months, at least 12 months, or at least 36 months after CAR-T (e.g., UCART19) administration.

Methods of Retreatment with CAR-T Cells

Also provided herein are methods for retreatment (redosing) with CAR-T cells. In particular, the methods involve administering one or more subsequent doses of cells to subjects having received a first dose, and/or administering the first and one or more subsequent doses. The doses generally are administered in particular amounts and according to particular timing parameters. In some embodiments, the methods generally involve administering a first dose of cells, thereby reducing disease burden, followed by a subsequent dose of cells, administered during a particular time window with respect to the first dose, or the administration of the subsequent dose to a subject having received such a first dose. In some embodiments, additional subsequent doses then are administered, for example, within the same or a similar window of time with respect to the subsequent dose. In some embodiments, the number of cells administered and timing of the multiple doses are designed to improve one or more outcomes, such as to reduce the likelihood or degree of toxicity to the subject, improve exposure of the subject to and/or persistence of the administered cells, and/or improve therapeutic efficacy. Also provided are articles of manufacture containing the cells and designed for administration following such dosing regimens.

In some embodiments, a subject to be treated with one or more subsequent doses of cells is in relapse. This means that the patient was in CR (complete response) or Cri (complete response with incomplete recovery of blood count) at a first time point after the initial dose, but relapsed at a second, later time point. The relapse may be, for example, a morphological relapse characterized by greater than or equal to 5% of blasts in bone marrow, the presence of extramedullary disease associated with the presence of blasts in bone marrow, or the presence of a minimum residual disease (MRD) defined as greater than or equal to 3-10 blasts in bone marrow.

In some embodiments, a subject to be treated with one or more subsequent doses of cells exhibited a suboptimal response after administration of the initial dose. For example, the subject may exhibit the presence of a minimum residual disease (MRD) at about 7, about 14, about 28, about 60, about 90, about 120, or about 365 days post administration of the initial dose.

In some embodiments, a subject to be treated with one or more subsequent doses of cells exhibits a non-persistence of CARs after administration of the initial dose. For example, a subject may present CARs detectable after the initial dose (D, CAR expansion), but does not have detectable CAR after D0. The lack of detectable CAR, in some embodiments, occurs even though the subject exhibits some signs of activity of the CAR-T cells (such as cytokine release syndrome).

In some embodiments, a subject to be treated with one or more subsequent doses of cells exhibits no substantial expansion of CAR-T cells. In some embodiments, the subject has no detectable CAR expansion and no response at about 7, about 14, about 28, about 60, about 90, about 120, or about 365 days post administration of the initial dose. In some embodiments, the subject has no detectable CAR expansion and some signs of treatment response (e.g., MRD positive subject) at about 7, about 14, about 28, about 60, about 90, about 120, or about 365 days post administration of the initial dose. In some embodiments, the subject has no detectable car expansion and complete response (e.g., MRD negative subject) at about 7, about 14, about 28, about 60, about 90, about 120, or about 365 days post administration of the initial dose.

In some embodiments, the provided methods involve a subsequent dose of cells administered at about the same number, and hence at a similar dose, as the first dose of cells. As shown herein, administration of a subsequent dose of cells can be advantageous compared to a single dose. In some embodiments, administration of subsequent dose(s) of cells, such as a dose of about $6 \times 10^5$ cells, about $6 \times 10^6$ cells, about $6 \times 10^7$ cells, about $8 \times 10^7$ cells, about $1.8 \times 10^8$ cells, or about $2.4 \times 10^8$ cells, are associated with an increased overall survival in subjects, particularly in subjects that exhibit morphological disease prior to treatment. In some embodiments, the methods include administering a first dose of cells that can expand in the presence of disease-associated antigens and reduce symptoms associated with disease but without the same degree of toxic outcomes that may be associated with a higher dose.

In some embodiments, the first dose is generally also large enough to be effective in reducing disease burden. In some cases, the first dose is large enough to reduce disease burden if the cell dose is sufficient to expand in vivo and debulk disease. In some embodiments, the cells of the first dose thereby debulk or reduce disease burden, e.g., tumor size, without effecting severe unwanted outcomes. In some cases, the first dose is an amount of cells that is effective to reduce tumor burden, such as by reducing disease from a morphological setting to minimum residual disease (MRD) and/or clinical or complete remission. In some aspects, the first dose is a low dose. In some aspects, for example, in the context of relatively low disease burden, the first dose may be higher.

In some embodiments, a risk-adapted dosing regimen may be used for determining the appropriate number or amount or relative number or amount of cells or CAR-T cells in the dose. For example, in some aspects, prior to infusion of CAR-T cells, the disease burden of the subject is determined and, based on the disease burden, a first dose of CAR-T cells (e.g. low or high dose) is selected that can minimize toxicity and maximize efficacy, for example, based on observations described above and elsewhere herein in which higher doses of recombinant receptor-expressing cells (e.g., CAR-expressing, such as CAR-expressing T cells) can be associated with toxic outcomes, such as severe neurotoxicity, in subjects having morphological disease burden, which are not necessarily observed, or are not observed to as great of an extent, in subjects with relatively lower disease burden. For example, subjects with a high marrow tumor burden prior to treatment, which, in some cases, can be associated with a greater CAR T-cell expansion following treatment, were observed to have a higher risk of developing severe neurotoxicity that may require ICU care.

In some embodiments, a subject is assessed for response after a first dose of allogeneic CAR-T cells. Such assessment may be conducted at about 1, about 2, about 3, about 4, about 5, about 6, about 7, about 8, about 9, about 10, about 11, or about 12 weeks after administration of the first or previous dose of allogeneic CAR-T cells. In some embodiments, a subject is assessed for response at between about one, about two, or about three months after administration of a first dose of allogeneic CAR-T cells.

In some embodiments, expression of antigens targeted by the CAR-T may be confirmed before administering a subsequent dose of CAR-T cells. For example, expression of antigens may be assessed by flow cytometry in blood, in other matrices, or in solid tumors. In some embodiments, a subject may be assessed for the absence of anti-HLA antibodies developed by the subject against prior CAR-T administered. In some embodiments, a subject may be assessed for the absence of anti-scFv antibodies developed by the subject after a prior CAR-T dosing. In some embodiments, a subject may be assessed for the absence any major safety issue after any course of CAR-T (first or subsequent courses). In some embodiments, a subject may be assessed for suitability for a subsequent lymphodepletion associated with CAR-T dosing. In some embodiments, absence of donor specific anti-HLA, anti-CAR scFv, and/or anti-TALEN antibodies after a CAR-T cell dosing indicates suitability of the subject for administration of a subsequent dose of CAR-T cells.

In some embodiments, absence of persistence of CAR-T cells beyond the day of the first evaluation of response after a CAR-T cell dosing indicates suitability of the subject for administration of a subsequent dose of CAR-T cells. In some embodiments, a subject may be assessed for absence of persistence of CAR-T cells beyond the day of the first evaluation of response after a CAR-T cell dosing. Assessment may be conducted according to the disease at, for example, about 1, about 2, about 3, about 4, about 5, about 6, about 7, about 8, about 9, about 10, about 11, or about 12 weeks after dosing, regardless of the response evaluated. Parameters for kinetics evaluation include, e.g., AUC0-timepoint of response evaluation, Cmax (peak expansion of transgene CAR-T, time of last observed quantifiable transgene, and level of CAR-T cell expansion in any other tissues or fluids. A suboptimal response after first CAR-T, irrespective of CAR-T persistence, dosing may include one or more of the following: (a) complete response (CR) or complete response with incomplete recovery of blood count (CRi), with detectable minimal residual disease (e.g., in leukemic patients); (b) absence of cytogenetic response; (c) marrow complete response; (d) partial response; and/or (e) stable response.

In some embodiments, a subject may be assessed for an adverse event beyond the day of the first evaluation of response after administration of a dose of CAR-T cells. Assessment may be conducted at, for example, about 1, about 2, about 3, about 4, about 5, about 6, about 7, about 8, about 9, about 10, about 11, or about 12 weeks after dosing. In some embodiments, assessment may be conducted within, e.g., the first four weeks (up to Day 28) after a CAR-T dosing. Exemplary adverse events are summarized in Table 4.

TABLE 4

| Toxicity | |
|---|---|
| Severe (grade 3-4) | cytokine release syndrome (according to modified Lee, 2014) |
| Moderate to Mild (grade 2-4) | acute graft versus host disease (according to Harris grading, 2016) |
| Severe (grade 3-4) | nervous system disorder |
| Life-threatening (grade 4) | tumor lysis syndrome (according to Cairo grading, 2008) |
| Severe (grade 3-4) | non-hematological toxicity |

In some embodiments, disease relapse may refer to relapse after having achieved an optimal CR after first CAR-T dosing. In some embodiments, disease relapse may refer to relapse after one or more CR is obtained with CAR-T, irrespective of when the relapse occurs.

A subsequent CAR-T dose may be issued from the same or another donor (donor of healthy cells used for CAR-T manufacturing). The same or different (higher or lower) dose of CAR-T cells may be applied in a subsequent dose.

The CAR-T cells may be administered as a single dose or as a split dose. For example, a dose can be split in two or more doses within a period, such as e.g., a seven day period. In some embodiments, a split dose comprises first and second administrations within a period. In some embodiments, an equal number of cells is administered at each of the first and second administrations. In some embodiments, fewer cells are administered during the first administration than are administered during the second administration. In some embodiments, a greater number of cells is administered during the first administration than is administered during the second administration. In some embodiments, a split dose comprises first, a second administration, and a third administration within a period. In some embodiments, an equal number of cells is administered at each of the first, second, and third administrations. In some embodiments, fewer cells are administered during the first administration than are administered during the second and third administrations. In some embodiments, a greater number of cells is administered during the first administration than is administered during the second and third administrations. In some embodiments, fewer cells are administered during the second administration than are administered during the first and third administration. In some embodiments, a greater number of cells is administered during the second administration than is administered during the first and third administration. In some embodiments, fewer cells are administered during the third administration than are administered during the first and second administration. In some embodiments, a greater number of cells is administered during the third administration than is administered during the first and second administration.

In some embodiments, a split dose is administered over a first day and a second day. In some embodiments, half of the dose is administered on the first day and half of the dose is administered on the second day. In some embodiments, one-third of the dose is administered on the first day, and two-thirds of the dose are administered on the second day. In some embodiments, two thirds of the dose are administered on the first day, and one third of the dose is administered on the second day. In some embodiments, each partial dose of the split dose is administered within 1, 2, 3, 4, 5, 6, 7, 8, 9, or 10 days of one another. In particular embodiments, each partial dose of the split dose is administered within 7 days of one another. In some embodiments, each partial dose is administered on a sequential day.

In some embodiments, a split dose is administered over a first day, a second day, and a third day. In some embodiments, one third of the dose is administered on the first day, one third of the dose is administered on the second day, and one third of the dose is administered on the third day. In some embodiments, each partial dose of the split dose is administered within 1, 2, 3, 4, 5, 6, 7, 8, 9, or 10 days of one another. In particular embodiments, each partial dose of the split dose is administered within 7 days of one another. In some embodiments, each partial dose is administered on a sequential day.

In some embodiments, a split dose is administered over at least three days, for example at least four days, at least five days, at least six days, or at least seven days.

Dosing Regimens

In some embodiments, allogeneic CAR-T cells are administered using a flat dose. In other embodiments, allogeneic CAR-T cells are administered using dose-banding. For example, dose-banding may be used to avoid the risk of a wide range of CAR-T cell exposure. In some embodiments, a weight band may be used. For example, without limitation, subjects <66 kg may be administered X dose, and subjects >66 kg may be administered about 1.33× dose. In some embodiments, subjects >50 kg may be administered one dose, and subjects ≤50 kg may be administered a different dose.

Exemplary dose levels for a first dose of UCART19 are provided in Table 5a, for use in adult patients with CD19+ relapsed/refractory B-cell acute lymphoblastic leukemia.

TABLE 5a

| UCART19 dose level | UCART19 dose expressed in number of cells | | Estimated UCART19 dose/kg |
|---|---|---|---|
| | Patient weight < 66 kg | Patient weight ≥ 66 kg | |
| DL-1 | | $6 \times 10^5$ cells | $1 \times 10^4$ cells/kg |
| DL1 | | $6 \times 10^6$ cells | $1 \times 10^5$ cells/kg |
| DL2 | $6 \times 10^7$ cells | $8 \times 10^7$ cells | $1 \times 10^6$ cells/kg |
| DL3 | $1.8 \times 10^8$ cells | $2.4 \times 10^8$ cells | $3 \times 10^6$ cells/kg |

Exemplary dose levels for a first dose of UCART19 are provided in Table 5b, for use in high-risk pediatric patients with CD19+ relapsed/refractory B-cell acute lymphoblastic leukemia.

TABLE 5b

| Weight (kg) | | Number of vials/ patient | UCART19 dose expressed in number of cells | Max TCRαβ$^+$ cells/kg in the weight band | Min dose CD19CAR/ RQR8$^+$_ TCRαβ$^-$_ T-cells/kg | Max dose CD19CAR/ RQR8$^+$_ TCRαβ$^-$_ T-cells/kg |
|---|---|---|---|---|---|---|
| ≥8.8 | <18 | 1 | $2 \times 10^7$ | $5.05 \times 10^4$ | $1.11 \times 10^6$ | $2.27 \times 10^6$ |
| ≥18 | <27 | 2 | $4 \times 10^7$ | $4.93 \times 10^4$ | $1.48 \times 10^6$ | $2.22 \times 10^6$ |
| ≥27 | <53 | 3 | $6 \times 10^7$ | $4.93 \times 10^4$ | $1.13 \times 10^6$ | $2.22 \times 10^6$ |
| ≥53 | <71 | 4 | $8 \times 10^7$ | $3.35 \times 10^4$ | $1.13 \times 10^6$ | $1.51 \times 10^6$ |

Exemplary dosage forms for a first dose of UCART19 are provided in Table 5c, for use in high-risk pediatric patients with CD19+ relapsed/refractory B-cell acute lymphoblastic leukemia.

TABLE 5c

| | | | DF3 | |
|---|---|---|---|---|
| | DF1 | DF2 | DF3.1 | DF3.2 |
| Pharmaceutical form | Suspension for infusion for Intravenous administration | | | |
| Drug substance dosage (CD19CAR/RQR8$^+$_TCRαβ$^-$_T-cells/mL) | $6 \times 10^5$ | $6 \times 10^6$ | $1.5 \times 10^7$ | $2 \times 10^7$ |

Exemplary dosages for a first dose of UCART19 are provided in Table 5d, for use in adult patients with Non-Hodgkin's lymphoma, such as relapsed/refractory large B-cell and/or follicular lymphoma.

TABLE 5d

| Dose Level | Dose ($\times 10^6$ CAR + viable cells) Patient weight > 50 kg | Dose ($\times 10^6$ CAR + viable cells) Patient weight ≤ 50 kg |
|---|---|---|
| 1 (starting) | 40 | 20 |
| 2 | 120 | 80 |
| 3 | 360 | 240 |
| −1 | 20 | No treatment |

In some embodiments, an allogeneic CAR-T cell dosing regimen comprises administering a first dose of CAR T-cells ranging between about $1 \times 10^5$ and $5 \times 10^8$ cells, or between about $1 \times 10^4$ cells/kg to about $3 \times 10^6$ cells/kg. In some embodiments, an allogeneic CAR-T cell dosing regimen comprises administering a first dose of CAR T-cells of about $6 \times 10^6$ cells (flat dose). In some embodiments, an allogeneic CAR-T cell dosing regimen comprises administering a first dose of about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $10 \times 10^4$, about $1 \times 10^5$, about $2 \times 10^5$, about $3 \times 10^5$, about $4 \times 10^5$, about $5 \times 10^5$, about $6 \times 10^5$, about $7 \times 10^5$, about $8 \times 10^5$, about $9 \times 10^5$, about $1 \times 10^6$, about $2 \times 10^6$, about $3 \times 10^6$, about $4 \times 10^6$, about $5 \times 10^6$, about $6 \times 10^6$, about $7 \times 10^6$, about $8 \times 10^6$, about $9 \times 10^6$, about $1 \times 10^7$, about $2 \times 10^7$, about $3 \times 10^7$, about $4 \times 10^7$, about $5 \times 10^7$, about $6 \times 10^7$, about $7 \times 10^7$, about $8 \times 10^7$, about $9 \times 10^7$, about $1 \times 10^8$, about $2 \times 10^8$, about $3 \times 10^8$, about $4 \times 10^8$, about $5 \times 10^8$, about $6 \times 10^8$, about $7 \times 10^8$, about $8 \times 10^8$, or about $9 \times 10^8$ CAR-T cells. In some embodiments, a dosing regimen comprises administering a first dose of about $1 \times 10^4$ cells, about $6 \times 10^6$ cells, about $7 \times 10^6$ cells (weight banded), or about $1.8 \times 10^8$ cells (weight banded). In some embodiments, a dosing regimen comprises administering a first dose of about $20 \times 10^6$ cells/dose, about $40 \times 10^6$ cells/dose, about $80 \times 10^6$ cells/dose, about $120 \times 10^6$ cells/dose, $240 \times 10^6$ cells/dose, or about $360 \times 10^6$ cells/dose (weight banded). In some embodiments, the dose is selected from the group consisting of about $20 \times 10^6$ cells/dose, about $80 \times 10^6$ cells/dose and about $240 \times 10^6$ cells/dose when the subject has a weight of less than or equal to 50 kg. In some embodiments, the dose is selected from the group consisting of about $20 \times 10^6$ cells/dose, about $40 \times 10^6$ cells/dose, about $120 \times 10^6$ cells/dose, and about $360 \times 10^6$ cells/dose when the subject has a weight of greater than 50 kg.

In some embodiments, a dosing regimen comprises administering a subsequent dose of about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $10 \times 10^4$, about $1 \times 10^5$, about $2 \times 10^5$, about $3 \times 10^5$, about $4 \times 10^5$, about $5 \times 10^5$, about $6\times10^5$, about $7\times10^5$, about $8\times10^5$, about $9\times10^5$, about $1\times10^6$, about $2\times10^6$, about $3\times10^6$, about $4\times10^6$, about $5\times10^6$, about $6\times10^6$, about $7\times10^6$, about $8\times10^6$, about $9\times10^6$, $1\times10^7$, about $2\times10^7$, about $3\times10^7$, about $4\times10^7$, about $5\times10^7$, about $6\times10^7$, about $7\times10^7$, about $8\times10^7$, about $9\times10^7$, about $1\times10^8$, about $2\times10^8$, about $3\times10^8$, about $4\times10^8$, about $5\times10^8$, about $6\times10^8$, about $7\times10^8$, about $8\times10^8$, or about $9\times10^8$ CAR-T cells. In some embodiments, a dosing regimen comprises administering a subsequent dose of about $1\times10^4$ cells, about $6\times10^6$ cells, about $7\times10^6$ cells, or about $1.8\times10^8$ cells. In some embodiments, an allogeneic CAR-T cell dosing regimen comprises administering a subsequent dose of CAR-T cells of about $6\times10^6$ cells (flat dose). In some embodiments, a dosing regimen comprises administering a subsequent dose of about $20\times10^6$ cells/dose, about $40\times10^6$ cells/dose, about $80\times10^6$ cells/dose, about $120\times10^6$ cells/dose, $240\times10^6$ cells/dose, or about $360\times10^6$ cells/dose (weight banded). In some embodiments, the dose is selected from the group consisting of about $20\times10^6$ cells/dose, about $80\times10^6$ cells/dose and about $240\times10^6$ cells/dose when the subject has a weight of less than or equal to 50 kg. In some embodiments, the dose is selected from the group consisting of about $20\times10^6$ cells/dose, about $40\times10^6$ cells/dose, about $120\times10^6$ cells/dose, and about $360\times10^6$ cells/dose when the subject has a weight of greater than 50 kg.

In some embodiments, an allogeneic CAR-T cell dosing regimen comprises administering a first dose of CAR T-cells of about $6\times10^6$ cells and a subsequent dose of CAR T-cells of about $6\times10^6$ cells. In some embodiments, a subsequent dose of CAR-T cells has about the same number of cells as the previous dose of CAR-T cells. In some embodiments, a subsequent dose of CAR-T cells has more cells as the previous dose of CAR-T cells. In some embodiments, a subsequent dose of CAR-T cells has fewer cells as the previous dose of CAR-T cells.

In some embodiments, a subsequent dose of allogeneic CAR-T cells may be administered during a particular time window with respect to an initial or previous dose of allogeneic CAR-T cells. In some embodiments, a subsequent dose of allogeneic CAR-T cells is administered about 4, 5, 6, 7, 8, 9, 10, 11, 12, 13, 14, 15, 16, 17, 18, 19, 20, 21, 22, 23, or 24 weeks after administration of an initial or previous dose of allogeneic CAR-T cells. In some embodiments, a subsequent dose of allogeneic CAR-T cells is administered between about 1, 2, 3, 4, 5, 6, 7, 8, 9, 10, 11, 12, 13, 14, 15, 16, 17, 18, 19, 20, 21, 22, 23, or even 24 months after administration of an initial or previous dose of allogeneic CAR-T cells. In some embodiments, a subsequent dose of allogeneic CAR-T cells is administered about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 days after administration of an initial or previous dose of allogeneic CAR-T cells.

In some embodiments, the time between the administration of the first dose (initial dose), e.g., the initiation of the administration of the first or prior dose, and the initiation of the administration of the subsequent dose (redose, e.g., the initiation of the administration of the subsequent dose) is greater than about 4 weeks, e.g., greater than about 5, 6, 7, 8, or 9 weeks, e.g., greater than about 20 weeks, e.g., between about 9 and about 35 weeks, between about 14 and about 28 weeks, between 15 and 27 weeks, or between 16 weeks and about 18 weeks; and/or at or about 15, 16, 17, 18, 19, 20, 21, 22, 23, 24, 25, 26, or 27 weeks. In some embodiments, administration of the subsequent dose (e.g., initiation thereof) is more than about 5 weeks after and less than about 24 weeks after administration of the first or prior dose (e.g., initiation thereof). In some embodiments, the administration of the subsequent dose is initiated 17 weeks following the initiation of the first dose. In some embodiments, the time between administration of the first and the subsequent dose (e.g., initiation thereof) or prior and next subsequent dose is greater than about 5 weeks and less than about 24 weeks, such as between 10 and 24 weeks, such as about 17 weeks. In some embodiments, the time between administration of the first and the subsequent dose (e.g., initiation thereof) is about 17 weeks.

In some embodiments, the subject receives a redose from 28 days to 9 months after the first CAR-T infusion. The same lymphodepletion regimen may be applied as for the first CAR-T dosing, or the regimen may be adapted to the patient's status and the degree of recovery of the host immune system.

In some embodiments, if a subject is in disease relapse after a subsequent dose of allogeneic CAR-T cells is administered, a further subsequent dose of allogeneic CAR-T cells may be administered. In some embodiments, if a subject is in disease relapse after a subsequent dose of allogeneic CAR-T cells is administered and a lack of persistence of CAR-T is observed, a further subsequent dose of allogeneic CAR-T cells may be administered. In some embodiments, two or more subsequent doses of allogeneic CAR-T cells may be administered after a first dose. Various regimens for subsequent dosing can used to extend durability of allogeneic CAR-T response. For example, subsequent doses of CAR-T can be administered, e.g., every other month (post first dose of CAR-T), or every 3 months. Any number of subsequent infusions may be administered. Timing of redosing may be adapted to patient's health status. An exemplary dosing regimen is depicted in FIG. 1.

In some embodiments, a dosing regimen comprises administering a first dose of about $6\times10^6$ CAR-T cells, followed by a subsequent dose of about $6\times10^6$ CAR-T cells administered at about 99 days after administration of the first dose. In other embodiments, a dosing regimen comprises administering a first dose of about $6\times10^6$ CAR-T cells, followed by a maintenance dose of about $6\times10^6$ CAR-T cells every 4 weeks until molecular remission is achieved. In other embodiments, a dosing regimen comprises administering a first dose of about $6\times10^6$ CAR-T cells, followed by a maintenance dose of about $6\times10^6$ CAR-T cells every 8 weeks until molecular remission is achieved.

In other embodiments, a dosing regimen comprises administering a bimonthly dose of about $6\times10^6$ CAR-T cells. In other embodiments, a dosing regimen comprises administering a dose of about $6\times10^6$ CAR-T cells.

However, other dosage regimens may be useful, depending on the pattern of pharmacokinetic decay that the practitioner wishes to achieve. The progress of this therapy is easily monitored by conventional techniques and assays. In preferred embodiments, the first dose and the first subsequent and additional subsequent doses are separated in time from each other by at least four weeks. The dosing regimen can vary over time.

Generally, for administration of allogeneic CAR-T cells an initial candidate dosage can be about 1.1 to about $2.3\times10^5$ cells/kg CAR-T cells. For the purpose of the present disclosure, a typical flat dosage of CAR-T cells might range from about any of about $1\times10^4$ to $1\times10^5$ to $1\times10^6$ to $1\times10^7$, to $1\times10^7$, to $1\times10^8$ cells or more, depending on the factors mentioned above. For example, dosage of about $0.3 \times 10^4$ cells, about $0.5 \times 10^4$ cells, about $1 \times 10^4$ cells, about $1.5 \times 10^4$ cells, about $2 \times 10^4$ cells, about $2.5 \times 10^4$ cells, about $3 \times 10^4$ cells, about $3.5 \times 10^4$ cells, about $4 \times 10^4$ cells, about $4.5 \times 10^4$ cells, about $5 \times 10^4$ cells, about $5.5 \times 10^4$ cells, about $6 \times 10^4$ cells, about $6.5 \times 10^4$ cells, about $7 \times 10^4$ cells, about $7.5 \times 10^4$ cells, about $8 \times 10^4$ cells, about $8.5 \times 10^4$ cells, about $9 \times 10^4$ cells, about $9.5 \times 10^4$ cells, about $1 \times 10^5$ cells, about $1.5 \times 10^5$ cells, $2 \times 10^5$ cells, about $2.5 \times 10^5$ cells, about $3 \times 10^5$ cells, about $3.5 \times 10^5$ cells, about $4 \times 10^5$ cells, about $4.5 \times 10^5$ cells, about $5 \times 10^5$ cells, about $5.5 \times 10^5$ cells, about $6 \times 10^5$ cells, about $6.5 \times 10^5$ cells, about $7 \times 10^5$ cells, about $7.5 \times 10^5$ cells, about $8 \times 10^5$ cells, about $8.5 \times 10^5$ cells, about $9 \times 10^5$ cells, about $9.5 \times 10^5$ cells, about $1 \times 10^6$ cells, about $1.5 \times 10^6$ cells, $2 \times 10^6$ cells, about $2.5 \times 10^6$ cells, about $3 \times 10^6$ cells, about $3.5 \times 10^6$ cells, about $4 \times 10^6$ cells, about $4.5 \times 10^6$ cells, about $5 \times 10^6$ cells, about $5.5 \times 10^6$ cells, about $6 \times 10^6$ cells, about $6.5 \times 10^6$ cells, about $7 \times 10^6$ cells, about $7.5 \times 10^6$ cells, about $8 \times 10^6$ cells, about $8.5 \times 10^6$ cells, about $9 \times 10^6$ cells, about $9.5 \times 10^6$ cells, about $1 \times 10^7$ cells, about $1.5 \times 10^7$ cells, $2 \times 10^7$ cells, about $2.5 \times 10^7$ cells, about $3 \times 10^7$ cells, about $3.5 \times 10^7$ cells, about $4 \times 10^7$ cells, about $4.5 \times 10^7$ cells, about $5 \times 10^7$ cells, about $5.5 \times 10^7$ cells, about $6 \times 10^7$ cells, about $6.5 \times 10^7$ cells, about $7 \times 10^7$ cells, about $7.5 \times 10^7$ cells, about $8 \times 10^7$ cells, about $8.5 \times 10^7$ cells, about $9 \times 10^7$ cells, about $9.5 \times 10^7$ cells, about $1 \times 10^8$ cells, about $1.5 \times 10^8$ cells, $2 \times 10^8$ cells, about $2.5 \times 10^8$ cells, about $3 \times 10^8$ cells, about $3.5 \times 10^8$ cells, about $4 \times 10^8$ cells, about $4.5 \times 10^8$ cells, about $5 \times 10^8$ cells, about $5.5 \times 10^8$ cells, about $6 \times 10^8$ cells, about $6.5 \times 10^8$ cells, about $7 \times 10^8$ cells, about $7.5 \times 10^8$ cells, about $8 \times 10^8$ cells, about $8.5 \times 10^8$ cells, about $9 \times 10^8$ cells, about $9.5 \times 10^8$ cells, or about $1 \times 10^9$ cells or more may be used. For subsequent administrations over several weeks or longer, depending on the disease, the treatment is sustained until a desired suppression of symptoms occurs or until sufficient therapeutic levels are achieved, for example, molecular remission.

An exemplary dosing regimen comprises administering a first dose of about $0.3 \times 10^4$ cells, about $0.5 \times 10^4$ cells, about $1 \times 10^4$ cells, about $1.5 \times 10^4$ cells, about $2 \times 10^4$ cells, about $2.5 \times 10^4$ cells, about $3 \times 10^4$ cells, about $3.5 \times 10^4$ cells, about $4 \times 10^4$ cells, about $4.5 \times 10^4$ cells, about $5 \times 10^4$ cells, about $5.5 \times 10^4$ cells, about $6 \times 10^4$ cells, about $6.5 \times 10^4$ cells, about $7 \times 10^4$ cells, about $7.5 \times 10^4$ cells, about $8 \times 10^4$ cells, about $8.5 \times 10^4$ cells, about $9 \times 10^4$ cells, about $9.5 \times 10^4$ cells, about $1 \times 10^5$ cells, about $1.5 \times 10^5$ cells, $2 \times 10^5$ cells, about $2.5 \times 10^5$ cells, about $3 \times 10^5$ cells, about $3.5 \times 10^5$ cells, about $4 \times 10^5$ cells, about $4.5 \times 10^5$ cells, about $5 \times 10^5$ cells, about $5.5 \times 10^5$ cells, about $6 \times 10^5$ cells, about $6.5 \times 10^5$ cells, about $7 \times 10^5$ cells, about $7.5 \times 10^5$ cells, about $8 \times 10^5$ cells, about $8.5 \times 10^5$ cells, about $9 \times 10^5$ cells, about $9.5 \times 10^5$ cells, about $1 \times 10^6$ cells, about $1.5 \times 10^6$ cells, $2 \times 10^6$ cells, about $2.5 \times 10^6$ cells, about $3 \times 10^6$ cells, about $3.5 \times 10^6$ cells, about $4 \times 10^6$ cells, about $4.5 \times 10^6$ cells, about $5 \times 10^6$ cells, about $5.5 \times 10^6$ cells, about $6 \times 10^6$ cells, about $6.5 \times 10^6$ cells, about $7 \times 10^6$ cells, about $7.5 \times 10^6$ cells, about $8 \times 10^6$ cells, about $8.5 \times 10^6$ cells, about $9 \times 10^6$ cells, about $9.5 \times 10^6$ cells, about $1 \times 10^7$ cells, about $1.5 \times 10^7$ cells, $2 \times 10^7$ cells, about $2.5 \times 10^7$ cells, about $3 \times 10^7$ cells, about $3.5 \times 10^7$ cells, about $4 \times 10^7$ cells, about $4.5 \times 10^7$ cells, about $5 \times 10^7$ cells, about $5.5 \times 10^7$ cells, about $6 \times 10^7$ cells, about $6.5 \times 10^7$ cells, about $7 \times 10^7$ cells, about $7.5 \times 10^7$ cells, about $8 \times 10^7$ cells, about $8.5 \times 10^7$ cells, about $9 \times 10^7$ cells, about $9.5 \times 10^7$ cells, about $1 \times 10^8$ cells, about $1.5 \times 10^8$ cells, about $2 \times 10^8$ cells, about $2.5 \times 10^8$ cells, about $3 \times 10^8$ cells, about $3.5 \times 10^8$ cells, about $4 \times 10^8$ cells, about $4.5 \times 10^8$ cells, about $5 \times 10^8$ cells, about $5.5 \times 10^8$ cells, about $6 \times 10^8$ cells, about $6.5 \times 10^8$ cells, about $7 \times 10^8$ cells, about $7.5 \times 10^8$ cells, about $8 \times 10^8$ cells, about $8.5 \times 10^8$ cells, about $9 \times 10^8$ cells, about $9.5 \times 10^8$ cells, or about $1 \times 10^9$ cells of allogeneic CAR-T cells. In some embodiments, a subsequent dose is administered monthly. In some embodiments, a subsequent dose is administered every other month. In some embodiments, a subsequent dose is administered about every three months. In some embodiments, a subsequent dose is administered about every four months. In some embodiments, a subsequent dose is administered about every five months. In some embodiments, a subsequent dose is administered about every six months. In some embodiments, a subsequent dose is administered about every seven months. In some embodiments, a subsequent dose is administered about every eight months. In preferred embodiments, the first dose and the first subsequent and additional subsequent doses are separated in time from each other by at least about four weeks. In some embodiments, a subsequent dose is administered every other month.

In some embodiments, a dosing regimen comprises administering to a subject a first dose of about $6 \times 10^6$ CAR-T cells at D0, and a subsequent dose of about $6 \times 10^6$ CAR-T cells at between about D30 to about D110. In some embodiments, a dosing regimen comprises administering to a subject a first dose of about $1 \times 10^6$ CAR-T cells at D0, and a subsequent dose of about $6 \times 10^6$ CAR-T cells at between about D30 to about D110. In some embodiments, a dosing regimen comprises administering to a subject a first dose of about $2 \times 10^6$ CAR-T cells at D0, and a subsequent dose of about $6 \times 10^6$ CAR-T cells at between about D30 to about D110. In some embodiments, a dosing regimen comprises administering to a subject a first dose of about $3 \times 10^6$ CAR-T cells at D0, and a subsequent dose of about $6 \times 10^6$ CAR-T cells at between about D30 to about D110. In some embodiments, a dosing regimen comprises administering to a subject a first dose of about $4 \times 10^6$ CAR-T cells at D0, and a subsequent dose of about $6 \times 10^6$ CAR-T cells at between about D30 to about D110. In some embodiments, a dosing regimen comprises administering to a subject a first dose of about $5 \times 10^6$ CAR-T cells at D0, and a subsequent dose of about $6 \times 10^6$ CAR-T cells at between about D30 to about D110. In some embodiments, a dosing regimen comprises administering to a subject a first dose of about $7 \times 10^6$ CAR-T cells at D0, and a subsequent dose of about $6 \times 10^6$ CAR-T cells at between about D30 to about D110. In some embodiments, a dosing regimen comprises administering to a subject a first dose of about $8 \times 10^6$ CAR-T cells at D0, and a subsequent dose of about $6 \times 10^6$ CAR-T cells at between about D30 to about D110. In some embodiments, a dosing regimen comprises administering to a subject a first dose of about $1 \times 10^6$ CAR-T cells at D0, and a subsequent dose of about $9 \times 10^6$ CAR-T cells at between about D30 to about D110. In some embodiments, a dosing regimen comprises administering to a subject a first dose of about $1 \times 10^7$ CAR-T cells at D0, and a subsequent dose of about $6 \times 10^6$ CAR-T cells at between about D30 to about D110.

In some embodiments, a dosing regimen comprises administering to a subject a lymphodepletion regimen at D-7 to D-2, followed by a first dose of about $6 \times 10^6$ CAR-T cells at D0, followed by an optional lymphodepletion regimen at D60 to D100, followed by a subsequent dose of $6 \times 10^6$ CAR-T cells at D63 to D104. In some embodiments, a dosing regimen comprises administering to a subject a lymphodepletion regimen at D-7 to D-2, followed by a first dose of about $6 \times 10^6$ CAR-T cells at D0, followed by an optional lymphodepletion regimen at D60 to D90, followed by a subsequent dose of $6 \times 10^6$ CAR-T cells at D63 to D104. In some embodiments, a dosing regimen comprises administering to a subject a lymphodepletion regimen (LD) at D-7, followed by a first dose of about 6×10⁶ CAR-T cells at D0, followed by reduced intensity (as compared to the previous LD) LD at D70, followed by a subsequent dose of 6×10⁶ CAR-T cells at D99. In some embodiments, a dosing regimen comprises administering to a subject a lymphodepletion regimen at D-15, followed by a first dose of about 6×10⁶ CAR-T cells at D0, followed by a lymphodepletion regimen at D60, followed by a subsequent dose of 6×10⁶ CAR-T cells at D75. In some embodiments, a dosing regimen comprises administering to a subject a lymphodepletion regimen at D-7 to D-2, followed by a first dose of about 6×10⁶ CAR-T cells at D0, followed by an optional lymphodepletion regimen at D60 to D90, followed by a subsequent dose of 6×10⁶ CAR-T cells at D63 to D104. In some embodiments, a dosing regimen comprises administering to a subject a lymphodepletion regimen at D-7 to D-2, followed by a first dose of about 6×10⁶ CAR-T cells at D0, followed by an optional lymphodepletion regimen at D60 to D90, followed by a subsequent dose of 6×10⁶ CAR-T cells at D63 to D104.

In some embodiments, a dosing regimen comprises administering to a subject a lymphodepletion regimen at D-5 to D-3, followed by a first dose of about 20×10⁶ cells, about 40×10⁶ cells, about 80×10⁶ cells, about 120×10⁶ cells, about 240×10⁶ cells, or about 360×10⁶ cells, followed by an optional subsequent dose of CAR-T cells. In some embodiments, the lymphodepletion regimen comprises fludarabine administered at a dosage of about 30 mg/m²; cyclophosphamide administered at about 300 mg/m²; and optionally a CD52 antibody (e.g., an antibody comprising the sequence of SEQ ID NO:8 and/or SEQ ID NO:10) administered at a dosage of about 10 to about 13 mg.

However, other dosage regimens may be useful, depending on the pattern of pharmacokinetic decay that the practitioner wishes to achieve. The progress of this therapy is easily monitored by conventional techniques and assays. In some embodiments, the first dose and the first subsequent and additional subsequent doses are separated in time from each other by at least four weeks. The dosing regimen can vary over time.

Allogeneic CAR-T Cells and Additional Agents

A description follows as to exemplary CAR-T cells used in accordance with the present disclosure.

The methods involve administering CAR-T cells which specifically bind to antigen associated with a disease and result in a response, such as an immune response against such molecules upon binding to such antigen. Any allogeneic CAR-T cells may be used with the methods described herein, unless specifically mentioned to be a method associated with a specific type of allogeneic CAR-T cells (e.g. UCART19 cells). In some embodiments, the methods and compositions of the instant disclosure are practiced using an allogeneic CAR-T cell specific for a tumor-specific antigen.

In some embodiments, the methods and compositions of the instant disclosure are practiced using an allogeneic CAR-T cell specific for CD19. In some embodiments, the CAR-T cell expresses a CAR comprising a CD19 binding domain. In some embodiments, the CD19 binding domain comprises a single chain variable fragment (scFv). In some embodiments, the scFv is derived from and anti-CD19 antibody (e.g., the 4G7 antibody). In some embodiments, the scFv comprises a VH and a VL isolated or derived from an anti-CD19 antibody (e.g., the 4G7 antibody). In some embodiments, the scFv comprises an HCDR1, HCDR2, HCDR3, LCDR1, LDCR2, and LCDR3 isolated or derived from an anti-CD19 antibody (e.g., the 4G7 antibody).

In some embodiments, the CAR-T cell expresses a CAR comprising a CD19 binding domain, a 4-1BB domain, and/or a CD3zeta domain.

In some embodiments, the CAR-T cell further expresses a "safety switch." Safety switches may comprise an epitope which enables selection of transduced cells and an epitope which enables cells expressing the polypeptide to be detected and/or deleted. In some embodiments, a safety switch comprises a mimitope. Exemplary safety switches are disclosed in, for example, WO 2013/153391, which is incorporated by reference herein in its entirety. In some embodiments, the safety switch binds to rituximab. In some embodiments the safety switch is expressed in trans with the CAR (e.g. as a separate polypeptide on the same cell). In some embodiments the safety switch is RQR8. In some embodiments the RQR8 containing safety switch is expressed in trans. Full length and component sequences for RQR8 are shown in Table 6, below.

TABLE 6

| Components of the RQR8 safety switch | | |
|---|---|---|
| Description of Sequence/ Origin | Sequence | SEQ ID NO |
| Full length RQR8 safety switch amino acid sequence | MLTSLLCWMALCLLG ADHADACPYSNPSLC SGGGGSELPTQGTFS NVSTNVSPAKPTTTA CPYSNPSLCSGGGGS PAPRPPTPAPTIASQ PLSLRPEACRPAAGG AVHTRGLDFACDIYI WAPLAGTCGVLLLSL VITLYCNHRNRRRVC KCPRPVVRAEGRGSL LTCGDVEENPGP | 12 |
| Human TCR beta leader sequence (with G to L substitution) | MLTSLLCWMALCLLG ADHADA | 13 |
| Rituximab epitope (synthetic) | CPYSNPSLC | 14 |
| glycine-serine linker (synthetic) | SGGGGS | 15 |
| Human CD34 sequence (QBEnd-10 epitope) | ELPTQGTFSNVSTNV S | 16 |
| Human CD8 hinge fragment | PAKPTTT | 17 |
| Human CD8 hinge | PAPRPPTPAPTIASQ PLSLRPEACRPAAGG AVHTRGLDFACD | 18 |
| Human CD8 trans-membrane | IYIWAPLAGTCGVLL LSLVIT | 19 |

TABLE 6-continued

| Components of the RQR8 safety switch | | |
| --- | --- | --- |
| Description of Sequence/ Origin | Sequence | SEQ ID NO |
| Human CD8 Intracellular Domain | LYCNHRNRRRVCKCP RPVV | 20 |
| 2A peptide from Thosea asigna virus (T2A) | RAEGRGSLLTCGDVE ENPG | 21 |

In some embodiments the safety switch is R2.

In some embodiments, the CAR-T cells do not comprise a safety switch.

In some embodiments, a sequence encoding a safety switch is provided on the same vector comprising a sequence encoding a CAR. In some embodiments, a sequence encoding a safety switch is provided on a different vector from the vector comprising a sequence encoding a CAR.

In some embodiments, a sequence encoding a safety switch is provided on the same polypeptide comprising the CAR (i.e., provided in cis). In some embodiments, the safety switch is provided on a different polypeptide from the CAR (i.e, provided in trans).

Accordingly, in some embodiments the safety switch is expressed in trans with the CAR (e.g. as a separate polypeptide on the same cell). In some embodiments the safety switch is RQR8. In some embodiments the RQR8 containing safety switch is expressed in trans.

In some embodiments, the safety switch is expressed in cis with the CAR, and comprises a mimotope, specific for an antibody, as described in WO 2013/153391.

In some embodiments, the CAR-T cell further comprises an inactivated CD52 gene. In some embodiments, a CAR-T cell is CD52-deficient. In some embodiments, CAR-T cells for administration to a patient comprise a mixture of CD52-deficient and CD52-positive cells.

In some embodiments, a composition of CAR-T cells for administration to a patient comprises a mixture of cells with different genotypes. In some embodiments, the composition comprises CAR-T cells wherein about 40%, about 45%, about 50%, about 55%, about 60%, about 65%, about 70%, about 75%, about 80%, about 85%, about 90%, about 95%, about 99%, or about 100% of the cells have an inactivated CD52 gene. In some embodiments, the composition comprises CAR-T cells wherein about 40%, about 45%, about 50%, about 55%, about 60%, about 65%, about 70%, about 75%, about 80%, about 85%, about 90%, about 95%, about 99%, or about 100% of the cells have an inactivated TRAC gene. In some embodiments, the composition comprises CAR-T cells wherein about 40%, about 45%, about 50%, about 55%, about 60%, about 65%, about 70%, about 75%, about 80%, about 85%, about 90%, about 95%, about 99%, or about 100% of the cells have an inactivated CD52 gene, and further wherein about 40%, about 45%, about 50%, about 55%, about 60%, about 65%, about 70%, about 75%, about 80%, about 85%, about 90%, about 95%, about 99%, or about 100% of the cells have an inactivated TRAC gene.

In some embodiments, the CAR-T cells are UCART19 CAR-T cells. UCART19 is an allogeneic engineered human T-cell medicinal product being developed for the treatment of CD19-expressing B-cell leukemias, including young adult, adult and pediatric acute lymphoblastic leukemia (B-ALL). Published information related to UCART19 includes: Qasim et al., "Molecular remission of infant B-ALL after infusion of universal TALEN gene-edited CAR T cells" *Sci Transl Med* 2017 Jan. 25; 9(374), Gouble et al., "In Vivo Proof of Concept of Activity and Safety of UCART19, an Allogeneic "Off-the-Shelf" Adoptive T-Cell Immunotherapy Against CD19+ B-Cell Leukemias" *Blood* 2014, 124(21) page 4689., and U.S. patent application Ser. No. 14/891,296, published May 2, 2016 as US 20160145337, each of which is herein incorporated by reference in its entirety. UCART19 expresses a CAR directed against human CD19 together with the safety switch RQR8 combining epitopes from both CD34 and CD20 antigens. UCART19 comprises an anti-human CD19 4-1BB/CD3zeta CAR, made up of one or more of the peptides shown in Table 7, and/or as described in U.S. Pat. App. Pub. No. 2016/0145337, which is incorporated by reference herein in its entirety.

TABLE 7

| UCART19 sequences | | |
| --- | --- | --- |
| Description of Sequence/ Origin | Sequence | SEQ ID NO |
| CAR full length amino acid sequence (version 2) | METDTLLLWVLLLWVPGSTG EVQLQQSGPELIKPGASVKM SCKASGYTFTSYVMHWVKQK PGQGLEWIGYINPYNDGTKY NEKFKGKATLTSDKSSSTAY MELSSLTSEDSAVYYCARGT YYYGSRVFDYWGQGTTLTVS SGGGGSGGGGSGGGGSDIVM TQAAPSIPVTPGESVSISCR SSKSLLNSNGNTYLYWFLQR PGQSPQLLIYRMSNLASGVP DRFSGSGSGTAFTLRISRVE AEDVGVYYCMQHLEYPFTFG AGTKLELKRSDPTTTPAPRP PTPAPTIASQPLSLRPEACR PAAGGAVHTRGLDFACDIYI WAPLAGTCGVLLLSLVITLY CKRGRKKLLYIFKQPFMRPV QTTQEEDGCSCRFPEEEEGG CELRVKFSRSADAPAYQQGQ NQLYNELNLGRREEYDVLDK RRGRDPEMGGKPRRKNPQEG LYNELQKDKMAEAYSEIGMK GERRRGKGHDGLYQGLSTAT KDTYDALHMQALPPR | 1 |
| CAR full length amino acid sequence (version 1) | MALPVTALLLPLALLLHAAR PEVQLQQSGPELIKPGASVK MSCKASGYTFTSYVMHWVKQ KPGQGLEWIGYINPYNDGTK YNEKFKGKATLTSDKSSSTA YMELSSLTSEDSAVYYCARG TYYYGSRVFDYWGQGTTLTV SSGGGGSGGGGSGGGGSDIV MTQAAPSIPVTPGESVSISC RSSKSLLNSNGNTYLYWFLQ RPGQSPQLLIYRMSNLASGV PDRESGSGSGTAFTLRISRV EAEDVGVYYCMQHLEYPFTF GAGTKLELKRADTTTPAPRP PTPAPTIASQPLSLRPEACR PAAGGAVHTRGLDFACDIYI WAPLAGTCGVLLLSLVITLY CKRGRKKLLYIFKQPFMRPV | 22 |

TABLE 7-continued

| Description of Sequence/ Origin | Sequence | SEQ ID NO |
|---|---|---|
| | QTTQEEDGCSCRFPEEEEGG CELRVKFSRSADAPAYQQGQ NQLYNELNLGRREEYDVLDK RRGRDPEMGGKPRRKNPQEG LYNELQKDKMAEAYSEIGMK GERRRGKGHDGLYQGLSTAT KDTYDALHMQALPPR | |
| UCART19 CAR full length amino acid sequence with RQR8 safety switch | MLTSLLCWMALCLLGADHAD ACPYSNPSLCSGGGGSELPT QGTFSNVSTNVSPAKPTTTA CPYSNPSLCSGGGGSPAPRP PTPAPTIASQPLSLRPEACR PAAGGAVHTRGLDFACDIYI WAPLAGTCGVLLLSLVITLY CNHRNRRRVCKCPRPVVRAE GRGSLLTCGDVEENPGPMET DTLLLWVLLLWVPGSTGEVQ LQQSGPELIKPGASVKMSCK ASGYTFTSYVMHWVKQKPGQ GLEWIGYINPYNDGTKYNEK FKGKATLTSDKSSSTAYMEL SSLTSEDSAVYYCARGTYYY GSRVFDYWGQGTTLTVSSGG GGSGGGGSGGGGSDIVMTQA APSIPVTPGESVSISCRSSK SLLNSNGNTYLYWFLQRPGQ SPQLLIYRMSNLASGVPDRF SGSGSGTAFTLRISRVEAED VGVYYCMQHLEYPFTFGAGT KLELKRSDPTTTPAPRPPTP APTIASQPLSLRPEACRPAA GGAVHTRGLDFACDIYIWAP LAGTCGVLLLSLVITLYCKR GRKKLLYIFKQPFMRPVQTT QEEDGCSCRFPEEEEGGCEL RVKFSRSADAPAYQQGQNQL YNELNLGRREEYDVLDKRRG RDPEMGGKPRRKNPQEGLYN ELQKDKMAEAYSEIGMKGER RRGKGHDGLYQGLSTATKDT YDALHMQALPPR | 23 |
| Mouse kappa light chain leader sequence | METDTLLLWVLLLWVPGSTG | 24 |
| Mouse anti- human CD19 (4G7) heavy chain (CDRs) | EVQLQQSGPELIKPGASVKM SCKASGYTFTSYVMHWVKQK PGQGLEWIGYINPYNDGTKY NEKFKGKATLTSDKSSSTAY MELSSLTSEDSAVYYCARGT YYYGSRVFDYWGQGTTLTVS S | 25 |
| Glycine-serine linker (synthetic) | GGGGSGGGGSGGGGS | 26 |
| Mouse anti- human CD19 (4G7) kappa light chain (with A to S substitution) (CDRs) | DIVMTQAAPSIPVTPGESVS ISCRSSKSLLNSNGNTYLYW FLQRPGQSPQLLIYRMSNLA SGVPDRESGSGSGTAFTLRI SRVEAEDVGVYYCMQHLEYP FTFGAGTKLELKRSD | 27 |
| Extracellular binding domain (version 2) | EVQLQQSGPELIKPGASVKM SCKASGYTFTSYVMHWVKQK PGQGLEWIGYINPYNDGTKY NEKFKGKATLTSDKSSSTAY MELSSLTSEDSAVYYCARGT YYYGSRVFDYWGQGTTLTVS SGGGGSGGGGSGGGGSDIVM TQAAPSIPVTPGESVSISCR | 28 |

TABLE 7-continued

| Description of Sequence/ Origin | Sequence | SEQ ID NO |
|---|---|---|
| | SSKSLLNSNGNTYLYWFLQR PGQSPQLLIYRMSNLASGVP DRFSGSGSGTAFTLRISRVE AEDVGVYYCMQHLEYPFTFG AGTKLELKRSDP | |
| Extracellular binding domain (version 1) | EVQLQQSGPELIKPGASVKM SCKASGYTFTSYVMHWVKQK PGQGLEWIGYINPYNDGTKY NEKFKGKATLTSDKSSSTAY MELSSLTSEDSAVYYCARGT YYYGSRVFDYWGQGTTLTVS SGGGGSGGGGSGGGGSDIVM TQAAPSIPVTPGESVSISCR SSKSLLNSNGNTYLYWFLQR PGQSPQLLIYRMSNLASGVP DRFSGSGSGTAFTLRISRVE AEDVGVYYCMQHLEYPFTFG AGTKLELKRAD | 29 |
| Human CD8 hinge | PTTTPAPRPPTPAPTIASQP LSLRPEACRPAAGGAVHTRG LDFACD | 30 |
| Human CD8 trans-membrane | IYIWAPLAGTCGVLLLSLVI T | 31 |
| Fragment of T- cell surface glycoprotein CD8 alpha chain isoform 1 precursor (residues 138- 206) | TTTPAPRPPTPAPTIASQPL SLRPEACRPAAGGAVHTRGL DFACDIYIWAPLAGTCGVLL LSLVITLYC | 32 |
| Human CD8 intracellular domain (partial) | LYC | 33 |
| Human 41BB intracellular domain | KRGRKKLLYIFKQPFMRPVQ TTQEEDGCSCRFPEEEEGGC EL | 34 |
| Human CD3 zeta intra-cellular domain | RVKFSRSADAPAYQQGQNQL YNELNLGRREEYDVLDKRRG RDPEMGGKPRRKNPQEGLYN ELQKDKMAEAYSEIGMKGER RRGKGHDGLYQGLSTATKDT YDALHMQALPPR | 35 |

UCART19 has additionally undergone the simultaneous disruption of the TRAC and CD52 genes followed by depletion of remaining TCRαβ+ cells. UCART19 comprises a single-chain variable fragment (scFv) derived from the murine anti-human CD19 4G7 hybridoma, a CD8 hinge and transmembrane domain, a 4-1BB co-stimulatory domain, and a CD3zeta signaling domain. The Drug Substance (DS) of UCART19 is defined as allogeneic genetically modified CD19CAR/RQR8+_TCRαβ-_T-cells: (i) containing an integrated self-inactivating (SIN) recombinant lentiviral delivery vector that expresses an anti-CD19 CAR to redirect T-cells to the CD19+ tumor cells and eliminate them, (ii) expressing an RQR8 safety switch, conferring susceptibility to rituximab, (iii) that are TCRαβ-negative via disruption of the TRAC gene using mRNA-based TALEN® gene-editing followed by depletion of the remaining TCRαβ+ cells during the manufacturing process, and (iv) that are a mix of CD52-knockout and CD52-positive cells via disruption of the CD52 gene using mRNA-based TALEN® gene-editing to allow administration of UCART19 to patients previously treated or being treated with an anti-CD52 antibody (e.g., an antibody comprising the sequence of SEQ ID NO:8 and/or SEQ ID NO:10).

Figure 4A:
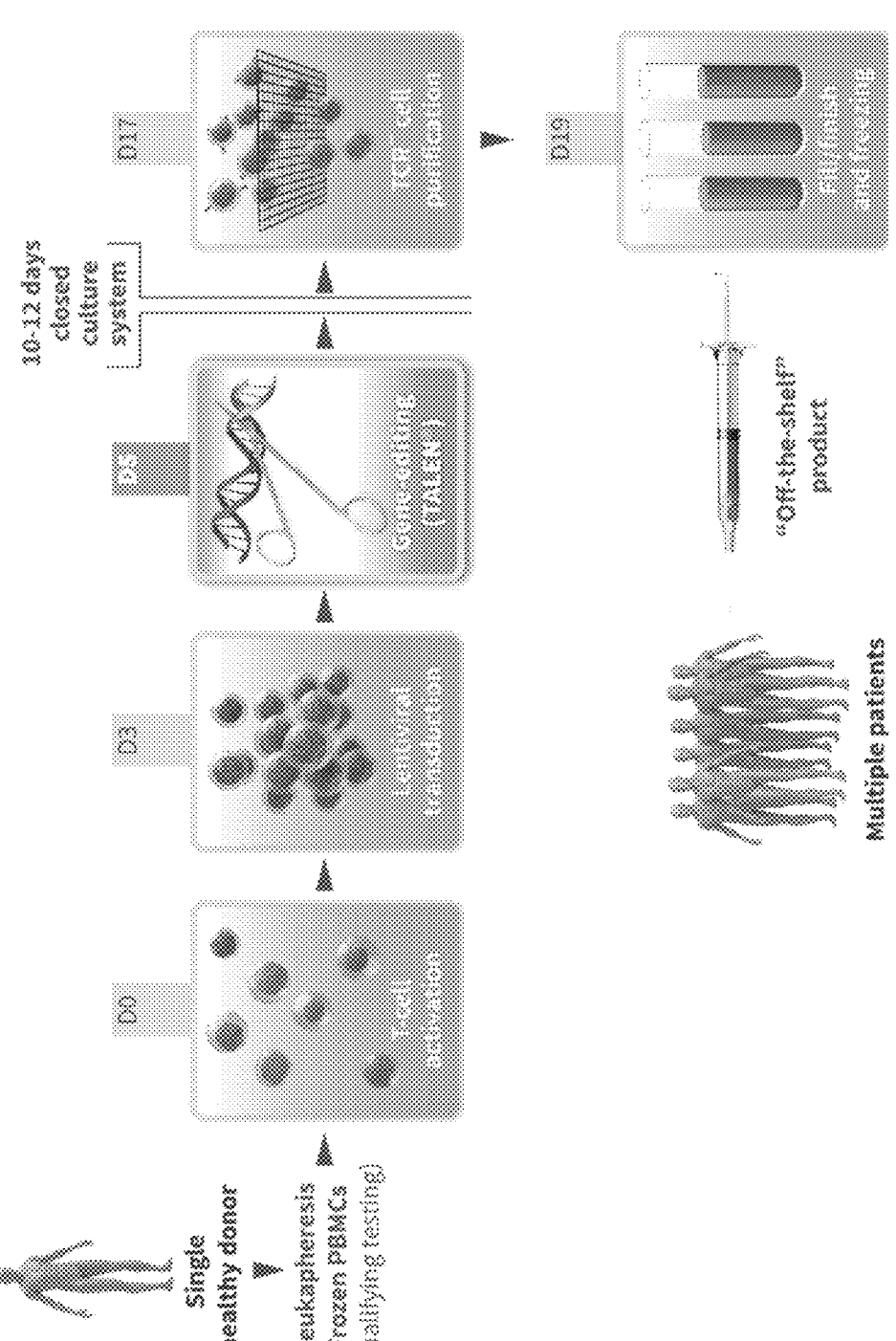
FIG. 4A and FIG. 4B depict exemplary flow diagrams for allogeneic CAR-T cell manufacturing.
Figure 4B:
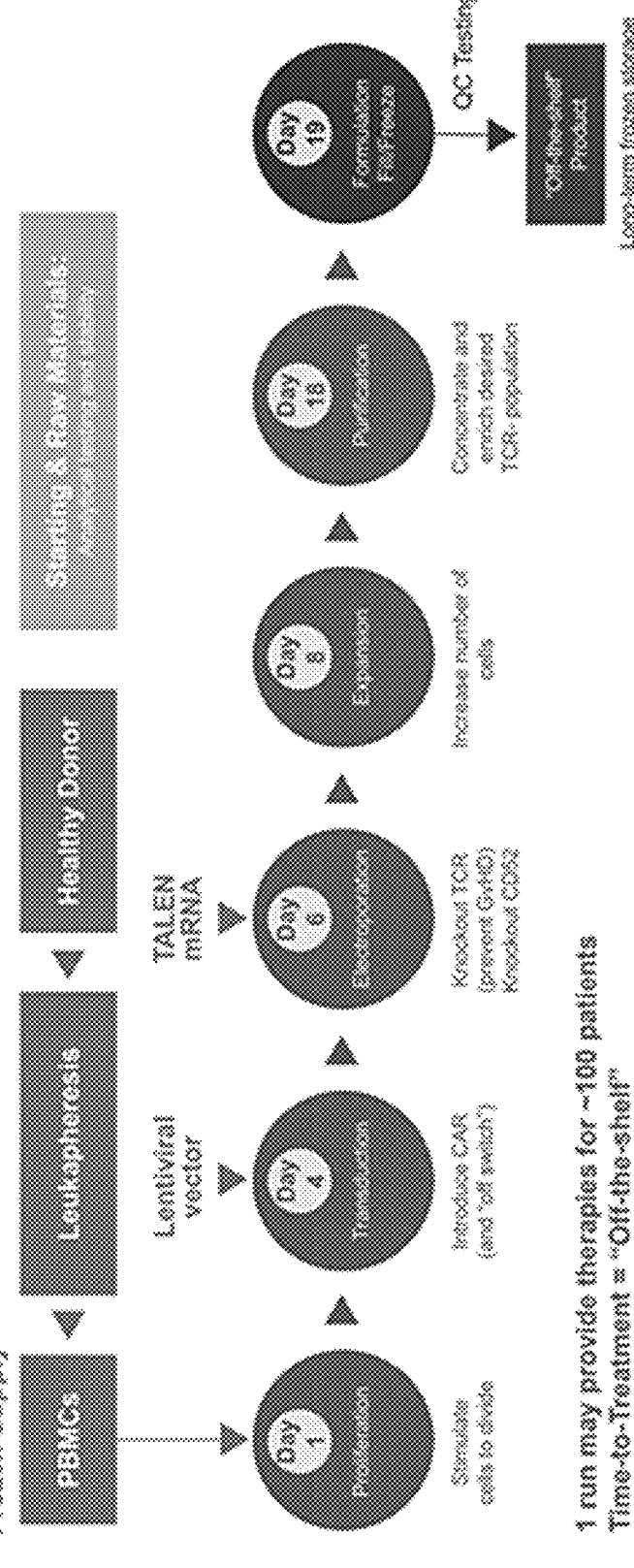

Exemplary flows for UCART19 manufacturing are shown in FIG. 4A and in FIG. 4B.

As used herein, UCART19 (CD19CAR/RQR8+_ TCRαβ-_T-cells) refers to UCART19 cells expressing a CD19 CAR and a RQR8 safety switch. The cells also comprise an inactivated TRAC gene. Optionally, the cells comprise an inactivated CD52 gene.

As used herein, UCART19 (CD19CAR/R2+_TCRαβ-_T-cells) refers to UCART19 cells expressing a CD19 CAR and a R2 safety switch. The cells also comprise an inactivated TRAC gene. Optionally, the cells comprise an inactivated CD52 gene.

As used herein, UCART19 (CD19CAR/TCRαβ-_T-cells) refers to UCART19 cells expressing a CD19 CAR. The cells also comprise an inactivated TRAC gene. Optionally, the cells comprise an inactivated CD52 gene.

In some embodiments, the CAR-T cells are allogeneic CAR-T cell expressing the amino acid sequence shown in SEQ ID NO:1.

With respect to all methods described herein, reference to CAR-T cell compositions also includes compositions comprising one or more additional agents. These compositions may further comprise suitable excipients, such as pharmaceutically acceptable excipients including buffers, which are well known in the art. The compositions and methods disclosed herein can be used alone or in combination with other conventional methods of treatment.

The CAR-T cells can be administered to a subject via any suitable route. It should be apparent to a person skilled in the art that the examples described herein are not intended to be limiting but to be illustrative of the techniques available. Accordingly, in some embodiments, the CAR-T cells are administered to a subject in accord with known methods, such as intravenous administration, e.g., as a bolus or by continuous infusion over a period of time, by intramuscular, intraperitoneal, intracerebrospinal, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution.

Various formulations of CAR-T cells may be used for administration. In some embodiments, CAR-T cells and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

These agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutical Kits and Articles of Manufacture

Also provided are pharmaceutical kids for treating patients suffering from a disease, such as cancer. In some embodiments, the pharmaceutical kit comprises CAR-T cells and a CD52 antibody. In some embodiments, the pharmaceutical kit comprises UCART19 cells and an antibody. In some embodiments, the pharmaceutical kit comprises a first container comprising CAR-T cells (e.g., UCART19 cells) and a second container comprising a CD52 antibody (e.g., an antibody comprising the sequence of SEQ ID NO:8 and/or SEQ ID NO:10). In some embodiments, the CAR-T cells (e.g., UCART19 cells) are CD52 deficient. In some embodiments, the kit comprises multiple containers comprising CAR-T cells, wherein the amount of CAR-T cells in each container is either the same or different. In some embodiments, the first and/or second containers are flexible cell infusion bags. In some embodiments, the first and/or second containers are vials or tubes (e.g., glass or plastic vials or tubes). The pharmaceutical kit may further comprise a label or package insert comprising instructions for administering the CAR-T cells and the CD52 antibody to the subject.

Also provided are articles of manufacture, comprising a plurality of sealable containers, each individually comprising a unit dose of allogeneic chimeric antigen receptor (CAR)-T cells for administration to a subject, said unit dose comprising about $1 \times 10^6$ to about $5 \times 10^8$ cells; packaging material; and a label or package insert comprising instructions for administering a plurality of said unit doses to the subject by carrying out a first administration and a subsequent administration, said first administration comprising delivering one of said unit doses to the subject and said subsequent administration comprising administering one or a plurality of said unit doses to the subject. In some embodiments, the articles of manufacture specify that said subsequent administration is to be carried out at a time between about 30 and 150 days, optionally at about day 30, about day 60, about day 90, or about day 99, following said first administration. In some embodiments, the containers are or comprise flexible cell infusion bags. In some embodiments, the containers are or comprise vials or tubes (e.g., glass or plastic vials or tubes).

Numbered Embodiments of the Disclosure

The disclosure and inventions described herein may be defined by reference to the following numbered, illustrative embodiments.

1. A method of treating a subject who has refractory and/or relapsed Non-Hodgkin's Lymphoma, the method comprising administering to the subject at least one dose of allogeneic chimeric antigen receptor (CAR)-T cells (CAR-T cells) comprising an anti-human CD19 4-1BB/CD3zeta CAR, wherein the at least one dose is about $20 \times 10^6$ cells/dose to about $360 \times 10^6$ cells/dose.

2. The method of embodiment 1, wherein the Non-Hodgkin's Lymphoma is large B-cell lymphoma.

3. The method of embodiment 1, wherein the Non-Hodgkin's Lymphoma is follicular lymphoma.

4. The method of any one of embodiments 1 to 3, wherein the at least one dose is selected from the group consisting of about $20 \times 10^6$ cells/dose, about $40 \times 10^6$ cells/dose, about $80 \times 10^6$ cells/dose, about $120 \times 10^6$ cells/dose, about $240 \times 10^6$ cells/dose, and about $360 \times 10^6$ cells/dose.

5. The method of any one of embodiments 1 to 4, wherein the at least one dose is selected from the group consisting of about $20 \times 10^6$ cells/dose, about $80 \times 10^6$ cells/dose and about $240 \times 10^6$ cells/dose when the subject has a weight of less than or equal to 50 kg.

6. The method of any one of embodiments 1 to 4 wherein the at least one dose is selected from the group consisting of about $20 \times 10^6$ cells/dose, about $40 \times 10^6$ cells/dose, about $120 \times 10^6$ cells/dose, and about $360 \times 10^6$ cells/dose when the subject has a weight of greater than 50 kg.

7. The method of any one of embodiments 1 to 6, wherein the CAR-T cells are CD52 deficient.

8. The method of any one of embodiments 1 to 6, wherein the CAR-T cells comprise a mixture of CD52-deficient and CD-52 positive cells 9. The method of any one of embodiments 1 to 8, wherein the CAR-T cells comprise the CAR of SEQ ID NO:1.

10. The method of any one of embodiments 1 to 9, wherein the CAR-T cells comprise UCART19(CD19) CAR/RQR8+_TCRαβ-_T-cells.

11. The method of any one of embodiments 1 to 9, wherein the CAR-T cells do not express a safety switch.

12. The method of any one of embodiments 1 to 11, wherein CAR expression is detectable in the subject for up to at least 14 days after administration of the CAR-T cells.

13. The method of any one of embodiments 1 to 12, wherein CAR expression is detectable in the subject for up to at least 28 days after administration of the CAR-T cells.

14. The method of any one of embodiments 1 to 13, wherein the subject exhibits a CR or Cri state for at least 1 months after CAR-T administration.

15. The method of any one of embodiments 1 to 14, wherein the subject exhibits a CR or Cri state for at least 2 months after CAR-T administration.

16. The method of any one of embodiments 1 to 15, wherein the subject exhibits a CR or Cri state for at least 6 months after CAR-T administration.

17. The method of any one of embodiments 1 to 16, wherein the subject exhibits a CR or Cri state for at least 12 months after CAR-T administration.

18. The method of any one of embodiments 1 to 17, wherein the subject receives a first lymphodepletion regimen prior to administration of the at least one dose.

19. The method of embodiment 18, wherein the first lymphodepletion regimen comprises administering fludarabine and cyclophosphamide.

20. The method of embodiment 18, wherein the first lymphodepletion regimen comprises administering fludarabine, cyclophosphamide, and an anti-CD52 antibody.

21. The method of embodiment 19 or 20, wherein the first lymphodepletion regimen further comprises administering Mensa (sodium-2-mercaptoethanesolfonate).

22. The method of any one of embodiments 19 to 21, wherein the first lymphodepletion regimen further comprises administering at least one corticosteroid.

23. The method of embodiment 22, wherein the corticosteroid is administered immediately prior to administration of the anti-CD52 antibody.

24. The method of embodiment 22 or 23, wherein the corticosteroid is methylprednisolone.

25. The method of embodiment 24, wherein the methylprednisolone is administered at a dose of 2 mg/kg.

26. The method of any one of embodiments 1 to 25, wherein the patient receives a premedication for infusion-related reaction prior to the lymphodepletion regimen.

27. The method of embodiment 26, wherein the premedication comprises at least one antihistamine.

28. The method of embodiment 26 or 27, wherein the premedication comprises acetaminophen.

29. The method of any one of embodiments 19 to 28, wherein fludarabine is administered at a dosage of about 30 mg/m$^2$/day; cyclophosphamide is administered at a dosage of about 300 mg/m$^2$/day; or CD52 antibody is administered at a dosage of about 10 to about 13 mg/day.

30. The method of any one of embodiments 20 to 28, wherein fludarabine is administered at a dosage of about 30 mg/m$^2$/day; cyclophosphamide is administered at a dosage of about 300 mg/m$^2$/day; and CD52 antibody is administered at a dosage of about 10 to about 13 mg/day.

31. The method of any one of embodiments 18 to 30, wherein the first lymphodepletion regimen is initiated between about 1 to 15 days prior to administration of the at least one dose.

32. The method of any one of embodiments 18 to 31, wherein the first lymphodepletion regimen is administered over the course of 1, 2, 3, 4, or 5 days.

33. The method of any one of embodiments 1 to 32, wherein the subject receives a subsequent dose of the CAR-T cells.

34. The method of embodiment 33, wherein the subject exhibits a suboptimal response at the time of the administration of the subsequent dose.

35. The method of embodiment 34, wherein the suboptimal response comprises:
(a) complete response (CR), complete response with incomplete recovery of blood count (CRi), with detectable minimal residual disease (leukemic patients) and absence of cytogenetic response;
(b) marrow complete response;
(c) partial response; or
(d) stable response.

36. The method of any one of embodiments 33-35 wherein the subsequent dose comprises about the same number of cells as the number of cells in the first dose.

37. The method of any one of embodiments 33-35, wherein the subsequent dose comprises an increased number of cells as compared to the first dose.

38. The method of any one of embodiments 33-35, wherein the subsequent dose comprises a decreased number of cells as compared to the first dose.

39. The method of any one of embodiments 33-38, wherein the subsequent dose is administered at least 14, at least 28, at least 42, or at least 56 days after the first dose.

40. A pharmaceutical kit for treating a patient suffering from cancer, the kit comprising:

(a) anti-CD19 CAR-T cells; and (b) a CD52 antibody.

41. The pharmaceutical kit of embodiment 40, wherein the CAR-T cells are UCART19 cells.

42. The pharmaceutical kit of embodiment 40 or 41, wherein the CAR-T cells express the CAR of SEQ ID NO:1.

43. The pharmaceutical kit of any one of embodiments 40 to 42, wherein the CD52 antibody comprises the sequence of SEQ ID NO:8 and/or SEQ ID NO:10.

44. The pharmaceutical kit of any one of embodiments 40 to 43, wherein the kit comprises a first container comprising the CAR-T cells, and a second container comprising the CD52 antibody.

45. The pharmaceutical kit of embodiment 44, wherein at least one of the first and the second container is a flexible cell infusion bag.

46. The pharmaceutical kit of any one of embodiments 40 to 45, wherein the kit further comprises a label or package insert comprising instructions for administering the CAR-T cells and the CD52 antibody to the subject.

47. A method of treatment, comprising:

(a) administering to a subject having a disease a first dose of chimeric antigen receptor (CAR)-T cells (CAR-T cells), and (b) administering to the subject a subsequent dose of CAR-T cells at a time point that is at least or more than about 28 days after and less than about 200 days after initiation of said administration in (a).

48. The method of embodiment 47, wherein the CAR-T cells are allogeneic.

49. The method of embodiment 47 or 48, wherein the first dose comprises about $1 \times 10^4$ to about $5 \times 10^8$ total cells.

50. The method of embodiment 49, wherein the first dose comprises about $6 \times 10^5$ total cells, about $6 \times 10^6$ total cells, about $6 \times 10^7$ total cells, about $8 \times 10^7$ total cells, about $1.8 \times 10^8$ total cells, about $2.4 \times 10^8$ total cells, or about $5 \times 10^8$ total cells.

51. The method of embodiment 47 or 48, wherein the first dose comprises between $1 \times 10^4$ and $2 \times 10^7$ cells per kilogram body weight of the subject.

52. The method of embodiment 51, wherein the first dose comprises about $1 \times 10^4$, about $1 \times 10^5$, about $1 \times 10^6$, about $3 \times 10^6$, or about $9 \times 10^6$ cells per kilogram body weight of the subject.

53. The method of any one of embodiments 47 to 52, wherein the subsequent dose of CAR-T cells is administered at about 28 days, about 60 days, or about 99 days after initiation of said administration in (a).

54. The method of embodiment 53, wherein the subsequent dose of CAR-T cells is administered at about 99 days after initiation of said administration in (a).

55. The method of any one of embodiments 47 to 54, wherein after step (a) and prior to step (b), the subject is administered an interim lymphodepletion regimen.

56. The method of any one of embodiments 47 to 55, wherein the interim lymphodepletion regimen comprises administering fludarabine, cyclophosphamide, and CD52 antibody to the subject between about 0 to 14 days prior to step (b).

57. The method of embodiment 56, wherein fludarabine is administered at a dosage of about 90 to 150 mg/m²; cyclophosphamide is administered at a dosage of about 1000 to 4000 mg/m²; and CD52 antibody is administered at a dosage of about 0.3 to 1 mg/kg.

58. The method of any one of embodiments 47 to 57, wherein the subject is administered a first lymphodepletion regimen.

59. The method of embodiment 47, wherein the first lymphodepletion regimen comprises administering fludarabine, cyclophosphamide, and CD52 antibody to the subject.

60. The method of embodiment 59, wherein fludarabine is administered at a dosage of about 90 to 150 mg/m²; cyclophosphamide is administered at a dosage of about 1000 to 4000 mg/m²; and CD52 antibody is administered at a dosage of about 0.3 to 1 mg/kg.

61. The method of any one of embodiments 58 to 60, wherein the first lymphodepletion regimen is initiated between about 15 to 5 days prior to step (a).

62. The method of any one of embodiments 58 to 60, wherein the first lymphodepletion regimen is completed between 2 to 10 days prior to step (a).

63. The method of any one of embodiments 47 to 62, wherein response is assessed between step (a) and step (b).

64. The method of embodiment 63, wherein the response is assessed prior to an interim lymphodepletion.

65. The method of any one of embodiments 47 to 64, wherein the subsequent dose comprises about $1 \times 10^5$ to about $5 \times 10^8$ total cells.

66. The method of any one of embodiments 47 to 65, wherein the subsequent dose comprises about $6 \times 10^6$ total cells.

67. The method of any one of embodiments 47 to 66, wherein the administration in (a) leads to amelioration of the disease in the subject, as indicated by a reduction in one or more symptoms of the disease following said administration in (a).

68. The method of embodiment 67, wherein at the time of the administration in (b), the subject has relapsed.

69. The method of any of embodiments 47 to 68, wherein the subsequent dose of cells comprises cells in an amount sufficient for amelioration of the disease in the subject.

70. The method of any of embodiments 47 to 69, wherein the administration in (b) leads to further amelioration of the disease in the subject.

71. The method of any of embodiments 47 to 70, wherein the administration of the subsequent dose leads to amelioration of the disease in the subject as compared with immediately prior to initiation of the administration of the subsequent dose.

72. The method of any of embodiments 47 to 71, wherein the method results in amelioration of the disease to a greater degree and/or for a greater period of time as compared to a method comprising an alternative dosing regimen wherein the subject is administered the cells in (a) and the cells in (b) in a single dose.

73. The method of any of embodiments 47 to 72, wherein the disease persists following the administration of the first dose and/or the administration of the first dose is not sufficient to eradicate the disease in the subject.

74. The method of any of embodiments 47 to 73, wherein the subject exhibits an absence of persistence of CAR-T cells at the time of the administration in (b).

75. The method of any of embodiments 47 to 74, wherein the subject exhibits one or more symptoms of the disease at the time of the administration in (b).

76. The method of any of embodiments 47 to 75, wherein the subject exhibits a suboptimal response at the time of the administration in (b).

77. The method of embodiments 76, wherein the suboptimal response comprises:

(a) complete response (CR), complete response with incomplete recovery of blood count (CRi), with detectable minimal residual disease (leukemic patients) and absence of cytogenetic response;

(b) marrow complete response;

(c) partial response; or (d) stable response.

78. The method of any of embodiments 47 to 77, wherein a cytokine release syndrome (CRS)-related outcome in the subject at day 2, 3, 4, 5, 6, 7, 8, 9, 10, 11, 12, 13, or 14 following the administration in (b) is not detectable or is reduced by about 20% to about 99% as compared to a method comprising an alternative dosing regimen wherein the subject is administered the cells in (b) without having been administered the first dose.

79. The method of any of embodiments 47 to 78, wherein the subsequent dose comprises about the same number of cells as the number of cells in the first dose.

80. The method of any of embodiments 47 to 78, wherein the subsequent dose comprises an increased number of cells as compared to the first dose.

81. The method of embodiment 80, wherein the subsequent dose comprises at least about 5% more cells than the number of cells of the first dose.

82. The method of any of embodiments 47 to 78, wherein the subsequent dose comprises a decreased number of cells as compared to the first dose.

83. The method of embodiment 82, wherein the subsequent dose comprises at least about 5% fewer cells than the number of cells of the first dose.

84. The method of any one of embodiments 47 to 83, wherein the disease is a tumor or a cancer.

85. The method of embodiment 84, wherein the cancer is leukemia or lymphoma.

86. The method of embodiment 84, wherein the tumor or cancer is acute lymphoblastic leukemia (ALL), is chronic lymphocytic leukemia (CLL), HNSCC, non-Hodgkin's lymphoma, acute myeloid leukemia, diffuse large B-cell lymphoma (DLBCL), multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, or mesothelioma.

87. The method of embodiment 86, wherein the ALL is relapsed or refractory ALL.

88. A method of treatment, comprising administering a subsequent dose of allogeneic chimeric antigen receptor (CAR)-T cells to a subject previously administered a first dose of allogeneic CAR-T cells, wherein: the subsequent dose of cells is administered at a time point that is at least or more than about 5 weeks after and less than about 24 weeks after initiation of the first dose.

89. A method of treatment, comprising administering to a subject a subsequent dose of allogeneic chimeric antigen receptor (CAR)-T cells, wherein: prior to said administration, the subject has received a previous dose of the CAR-T cells in an amount sufficient to demonstrate clinical benefit in the subject; and at the time of administration, the subject does not exhibit a detectable adaptive host immune response specific for the CAR-T cells; and/or the time between said previous and subsequent doses is greater than about 5 weeks and less than about 24 weeks.

90. The method of embodiment 88, wherein the number of cells administered in the subsequent dose is the same as the number of cells administered in the first dose.

91. The method of embodiment 88, wherein the number of cells administered in the subsequent dose is greater than the number of cells administered in the first dose.

92. Use of a composition comprising allogeneic chimeric antigen receptor (CAR)-T cells for manufacture of a medicament for treatment of a disease in a subject previously treated with the CAR-T cells, wherein: the composition is for use between about 5 to about 24 weeks after the previous treatment; and/or the composition is formulated for administration of a subsequent dose in an amount sufficient for amelioration of a disease in the subject having been previously treated with the CAR-T cells.

93. A composition comprising allogeneic chimeric antigen receptor (CAR)-T cells for use in treating a disease in a subject previously treated with the CAR-T cells, wherein: the cells are for use between about 5 and 24 weeks after the previous treatment; and the cells are formulated for administration of a subsequent dose in an amount sufficient for amelioration of a disease in the subject having been previously treated with the CAR-T cells.

94. The use of embodiment 92 or composition for use according to embodiment 93, wherein the dose of CAR-T cells in the previous treatment ameliorated one or more symptoms of the disease in the subject prior to use of the subsequent dose.

95. Use of allogeneic chimeric antigen receptor (CAR)-T cells in the manufacture of a medicament for use in a method for treating a disease, said method comprising: administering to a subject having the disease a first dose of the CAR-T cells, said first dose comprising between about $1 \times 10^6$ to about $5 \times 10^8$ total cells and; administering to the subject a subsequent dose of the CAR-T cells at a time point that is at least or more than about 4 weeks after and less than about 24 weeks after initiation of said administration in (a).

96. The use of embodiments 92, 94, or 95, or composition for use according to embodiment 93, wherein the disease is a leukemia or lymphoma.

97. The method of any of embodiments 47 to 83, the use of any one of embodiments 92 or 94 to 95, or the composition for use according to embodiment 93, wherein the CAR-T cells are tumor antigen-specific CAR-T cells.

98. The method of any of embodiments 47 to 83, the use of any one of embodiments 92 or 94 to 95, or the composition for use according to embodiment 93, wherein the CAR-T cells are UCART19 cells.

99. An article of manufacture, comprising:
a plurality of sealable containers, each individually comprising a unit dose of allogeneic chimeric antigen receptor (CAR)-T cells for administration to a subject, said unit dose comprising about $1\times10^6$ to about $5\times10^8$ cells; packaging material; and a label or package insert comprising instructions for administering a plurality of said unit doses to the subject by carrying out a first administration and a subsequent administration, said first administration comprising delivering one of said unit doses to the subject and said subsequent administration comprising administering one or a plurality of said unit doses to the subject.

100. The article of manufacture of embodiment 99, wherein the instructions specify that said subsequent administration is to be carried out at a time between about 30 and 150 days, optionally at about day 30, about day 60, about day 90, or about day 99, following said first administration.

101. The article of manufacture of embodiment 99 or 100, wherein the containers are or comprise flexible cell infusion bags.

102. A method of treating an adult subject who has refractory and/or relapsed CD19+ B-cell acute lymphoblastic leukemia, comprising administering to the subject at least one dose of allogeneic chimeric antigen receptor (CAR)-T cells (CAR-T cells) comprising an anti-human CD19 4-1BB/CD3zeta CAR, wherein the at least one dose is selected from the group consisting of about $6\times10^5$ cell/dose, $6\times10^6$ cells/dose, about 6-8× $10^7$ cells/dose, and about $1.8-2.4\times10^8$ cells/dose.

103. A method of treating an pediatric subject who has refractory and/or relapsed CD19+ B-cell acute lymphoblastic leukemia, comprising administering to the subject at least one dose of allogeneic chimeric antigen receptor (CAR)-T cells (CAR-T cells) comprising an anti-human CD19 4-1BB/CD3zeta CAR, wherein the at least one dose is about $2-8\times10^7$ cells/dose.

104. The method of embodiment 102 or 103, wherein the CAR-T cells are CD52 deficient.

105. The method of embodiment 102 or 103, wherein the CAR-T cells comprise a mixture of CD52-deficient and CD-52 positive cells.

106. The method of any one of embodiments 102 to 105, wherein the CAR-T cells express the CAR of SEQ ID NO:1.

107. The method of any one of embodiments 102 to 106, wherein the CAR-T cells comprise UCART19 (CD19CAR/RQR8+_TCRαβ-_T-cells).

108. The method of any one of embodiments 102 to 107, wherein CAR expression is detectable in the subject for up to at least 42 days after administration of the CAR-T cells.

109. The method of any one of embodiments 102 to 108, wherein CAR expression is detectable in the subject for up to at least 56 days after administration of the CAR-T cells.

110. The method of any one of embodiments 102 to 109, wherein the subject exhibits a CR or Cri state for at least 1.3 months after UCART19 administration.

111. The method of any one of embodiments 102 to 110, wherein the subject exhibits a CR or Cri state for at least 1.8 months after UCART19 administration.

112. The method of any one of embodiments 102 to 111, wherein the subject exhibits a CR or Cri state for at least 3.6 months after UCART19 administration.

113. The method of any one of embodiments 102 to 112, wherein the subject exhibits a CR or Cri state for at least 12.4 months after UCART19 administration.

114. The method of any one of embodiments 102 to 113, wherein the subject receives a first lymphodepletion regimen prior to administration of the at least one dose.

115. The method of embodiment 114, wherein the first lymphodepletion regimen comprises administering fludarabine and cyclophosphamide.

116. The method of embodiment 114, wherein the first lymphodepletion regimen comprises administering fludarabine, cyclophosphamide, and an anti-CD52 antibody.

117. The method of embodiment 115 or 116, wherein fludarabine is administered at a dosage of about 30 to 150 mg/m$^2$; cyclophosphamide is administered at a dosage of about 300 to 4000 mg/m$^2$; and CD52 antibody is administered at a dosage of about 0.3 to 1 mg/kg.

118. The method of any one of embodiments 114 to 117, wherein the first lymphodepletion regimen is initiated between about 1 to 15 days prior to administration of the at least one dose.

119. The method of any one of embodiments 114 to 118, wherein the subject receives a subsequent dose of the CAR-T cells.

120. The method of embodiment 119, wherein the subject exhibits a suboptimal response at the time of the administration of the subsequent dose.

121. The method of embodiment 120, wherein the suboptimal response comprises:
(a) complete response (CR), complete response with incomplete recovery of blood count (CRi), with detectable minimal residual disease (leukemic patients) and absence of cytogenetic response;
(b) marrow complete response;
(c) partial response; or
(d) stable response.

122. The method of embodiment 119, wherein the subsequent dose comprises about the same number of cells as the number of cells in the first dose.

123. The method of embodiment 119, wherein the subsequent dose comprises an increased number of cells as compared to the first dose.

124. The method of embodiment 119, wherein the subsequent dose comprises a decreased number of cells as compared to the first dose.

125. A method of producing a population of allogeneic chimeric antigen receptor (CAR)-T cells (CAR-T cells) directed to a target of interest comprising:
isolating peripheral blood mononuclear cells (PBMCs) from a healthy donor;
activating the T-cells in the PBMCs;
transducing the activated T-cells with a lentiviral vector, wherein the lentiviral vector is a self-inactivating recombinant vector expressing a CAR of interest;
disrupting TCRαβ and CD-52 gene expression in a subset of the T-cells;
expanding the population of T-cells; and
enriching the population of T-cells for TCRαβ-negative cells;
whereby generating a population of allogeneic chimeric antigen receptor (CAR)-T cells (CAR-T cells).

126. The method of embodiment 125, wherein step (c) is carried out about 3-4 days following step (b).

127. The method of embodiment 125 or 126, wherein step (d) is carried out about 2 days following step (c).

128. The method of any one of embodiments 125 to 127, wherein step (f) is carried out about 10-12 days following step (d).

129. The method of any one of embodiments 125 to 128, wherein the CAR-T cells are CD52 deficient.

130. The method of any one of embodiments 125 to 129, wherein the CAR-T cells comprise a mixture of CD52-deficient and CD-52 positive cells.

131. The method of any one of embodiments 125 to 130, wherein the CAR-T cells express the CAR of SEQ ID NO:1.

132. The method of any one of embodiments 125 to 131, wherein the CAR-T cells comprise UCART19 (CD19CAR/RQR8+_TCRαβ-_T-cells).

133. The method of any one of embodiments 125 to 132, wherein the lentiviral vector of step (c) further expresses a safety switch.

134. The method of embodiment 133, wherein the safety switch is RQR8.

EXAMPLES

The following examples are meant to illustrate the methods and materials of the present disclosure. Suitable modifications and adaptations of the described diseases and parameters normally encountered in the art that are obvious to those skilled in the art are within the spirit and scope of the present disclosure.

Example 1: Allogeneic CAR-T Dosing Regimen

This example illustrates multiple dose treatment with allogeneic CAR-T cells.

Prior to administration of the CAR-T cells, subjects with disease are administered a lymphodepletion regimen. Such regimen may comprise, e.g., treatment with fludarabine (range total dose about 30 to 150 mg/m$^2$) and cyclophosphamide (range total dose about 300 to 4000 mg/m$^2$), with an anti-CD52 drug (e.g., a CD52 antibody, such as an antibody comprising the sequence of SEQ ID NO:8 and SEQ ID NO:10) (range total dose about 0.3 to 1 mg/kg).

Subjects are administered a first dose of CAR-T cells of between about $1 \times 10^4$ to about $5 \times 10^8$ cells at D0.

Between about D24 and D62, response to the first dose of CAR-T cells is assessed. The number of CAR-T cells present in peripheral blood of treated subjects is determined by performing flow cytometry of a cell sample for surface expression of CAR-specific marker, CD4, and/or CD8. Positive MRD and/or loss of persistence suggest subsequent dosing with CAR-T cells.

Prior to subsequent dosing with CAR-T cells, subjects with MRD are administered a lymphodepletion regimen. Such regimen may comprise, e.g., treatment with fludarabine (range total dose about 30 to 150 mg/m$^2$) and cyclophosphamide (range total dose about 300 to 4000 mg/m$^2$), with or without an anti-CD52 (range total dose about 0.3 to 1 mg/kg). Between 2 and 14 days post-lymphodepletion, subjects are administered a dose of CAR-T cells of between about $1 \times 10^4$ to about $1 \times 10^8$ cells. Response to the dose of CAR-T cells is assessed, and the number of CAR-T cells present in peripheral blood of treated subjects is determined. Positive MRD and/or loss of persistence suggest subsequent dosing with CAR-T cells. Multiple doses of allogeneic CAR-T may be administered until MRD negativity is achieved.

Example 2: Use of an Allogeneic Anti-CD19 CAR-T Cell Product (UCART19) in Adult Patients with CD19+ Relapsed/Refractory B-Cell Acute Lymphoblastic Leukemia This study was carried out to address treatment of B-ALL. B-ALL is incurable in ~60% of adult patients. At relapse, prognosis is very poor (<10% overall survival). Standard therapy involves combination chemotherapy±allogeneic SCT.

Subjects were administered an allogeneic, universal, adoptive T-cell therapy targeting CD19+ malignancies.

Figure 5:
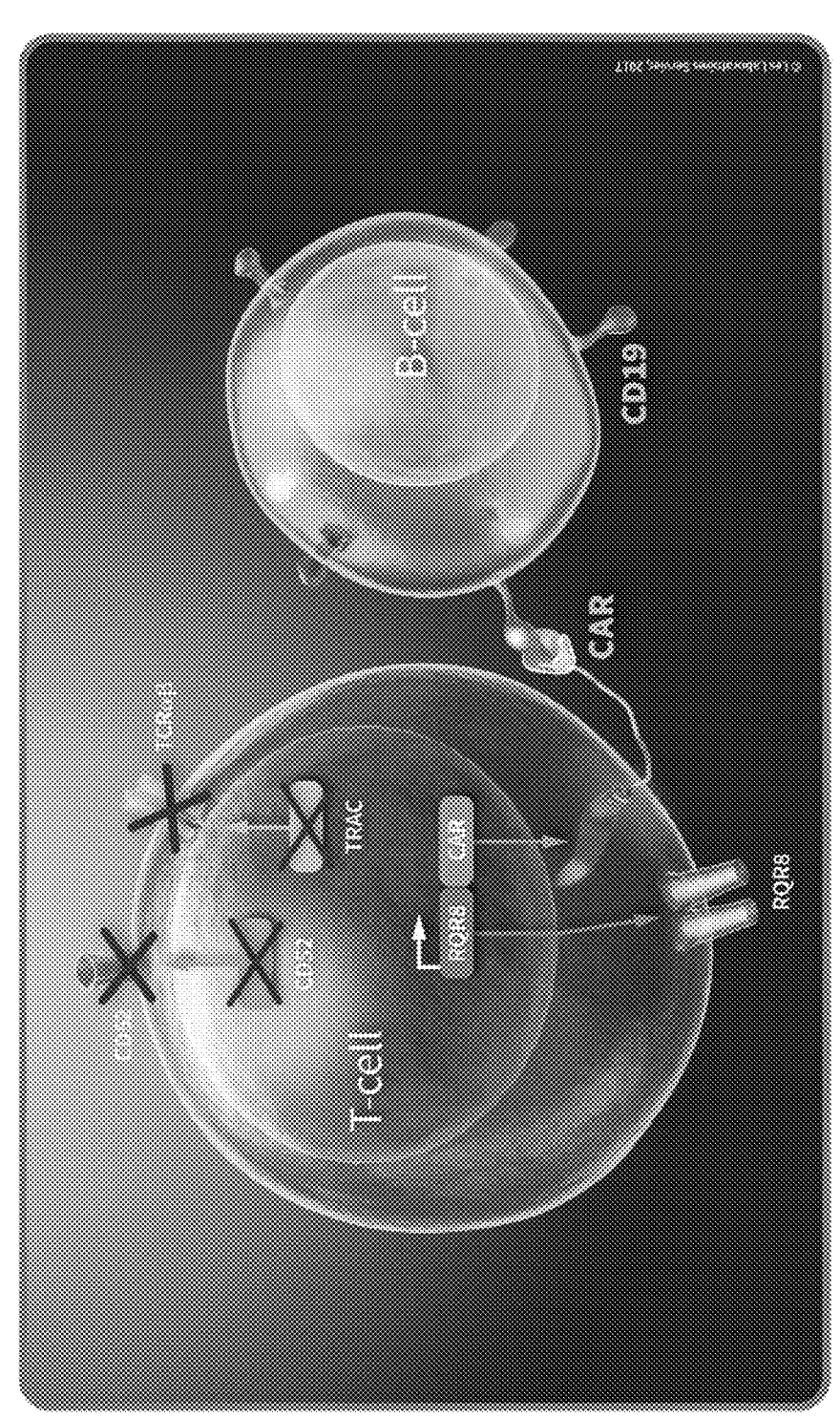
FIG. 5 depicts an exemplary engineered allogeneic anti-CD19 CAR T-cell product (CD19CAR/RQR8+_TCRαβ-_T-cells).

Transgene expression was achieved using lentiviral transduction. UCART19 comprises an anti-CD19 scFv and an intracellular domain comprising CD3ζ+4-1BB. The CAR-T cell further comprises a RQR8 (CD20 mimotope) safety switched expressed in trans. The CAR-T cells were prepared by further knockouts, using TALEN-based technologies. Specifically the TRAC was knocked out, to prevent TCR mediated recognition of patient's HLA antigens. The CD52 was knocked out to permit CD52 antibody use in lymphodepletion. An illustrative UCART19 cell as used here (CD19CAR/RQR8+_TCRαβ-_T-cells) is provided in FIG. 5.

Figure 6B:
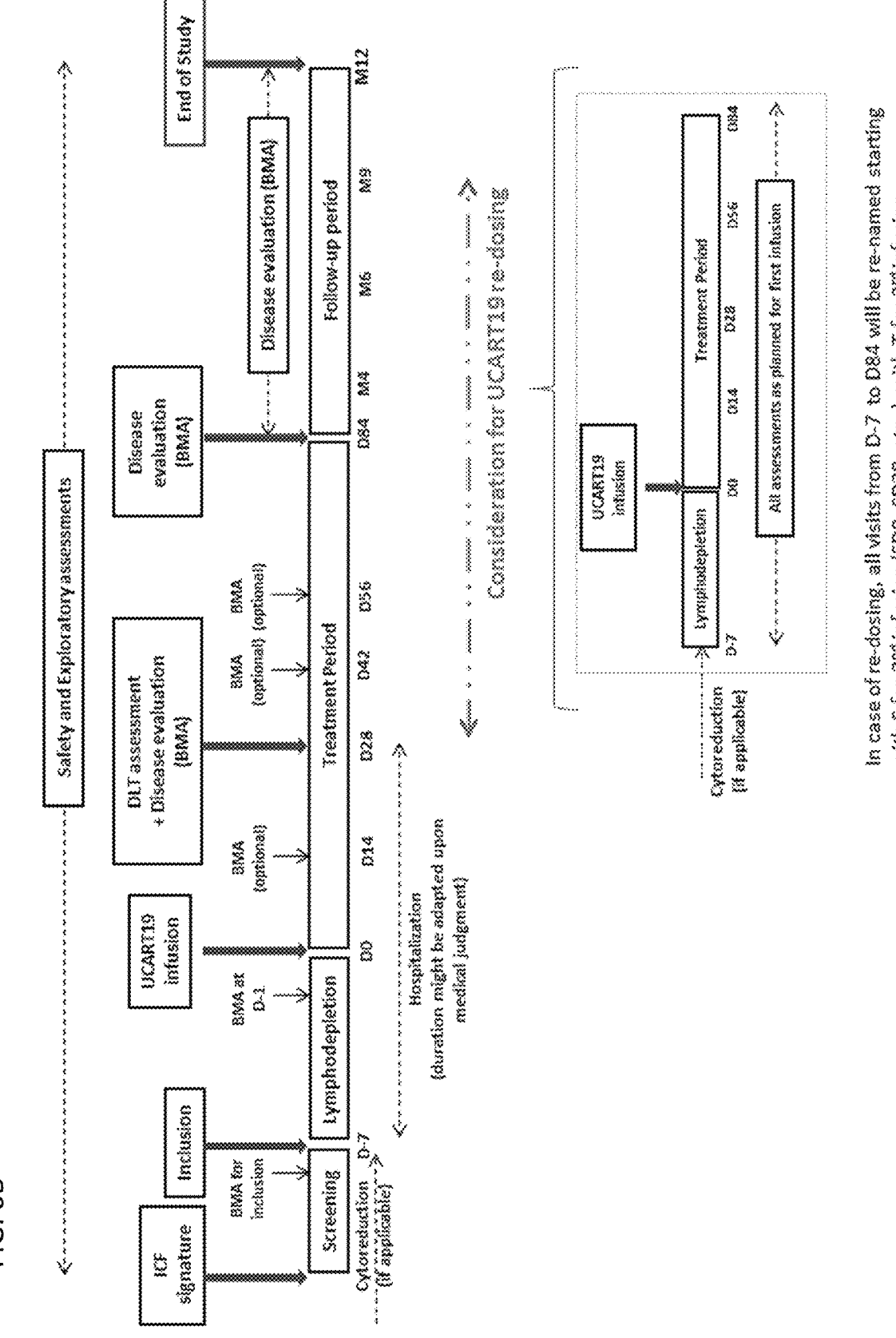

This study had at least 3 objectives, and schematics of the study design schematic are presented in FIG. 6A and FIG. 6B (BMA=bone marrow aspiration).

Objective #1: Evaluation of safety and tolerability of UCART19 at different doses; and determination of the maximum tolerated dose (MTD). (FIG. 3B).

Objective #2: Assessment of anti-leukemic activity.

Objective #3: Evaluate expansion and persistence of UCART19.

Figure 3A:
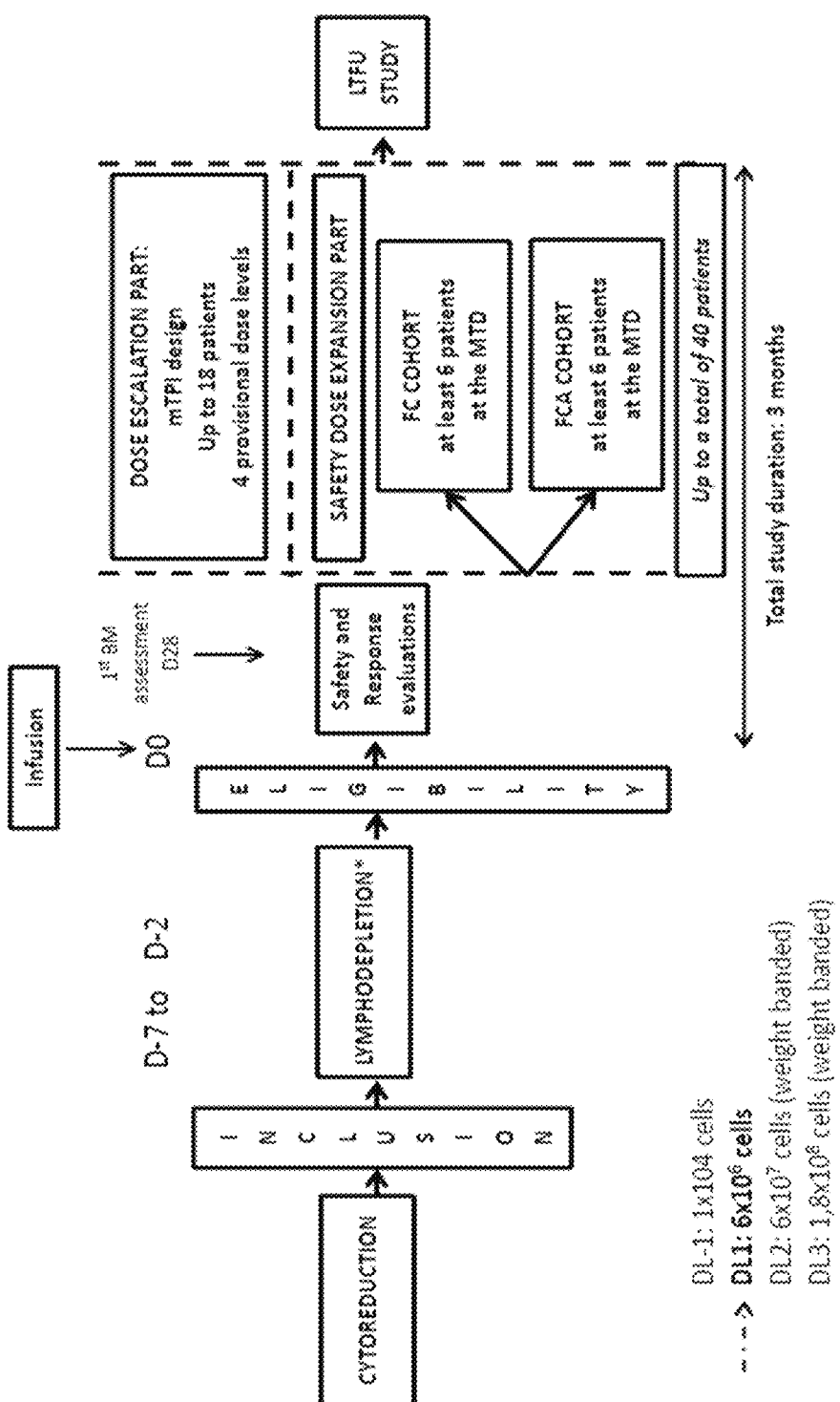
FIG. 3A depicts an exemplary schematic showing the steps of a dosing regimen for allogeneic CAR-T cell treatment.
Figure 3B:
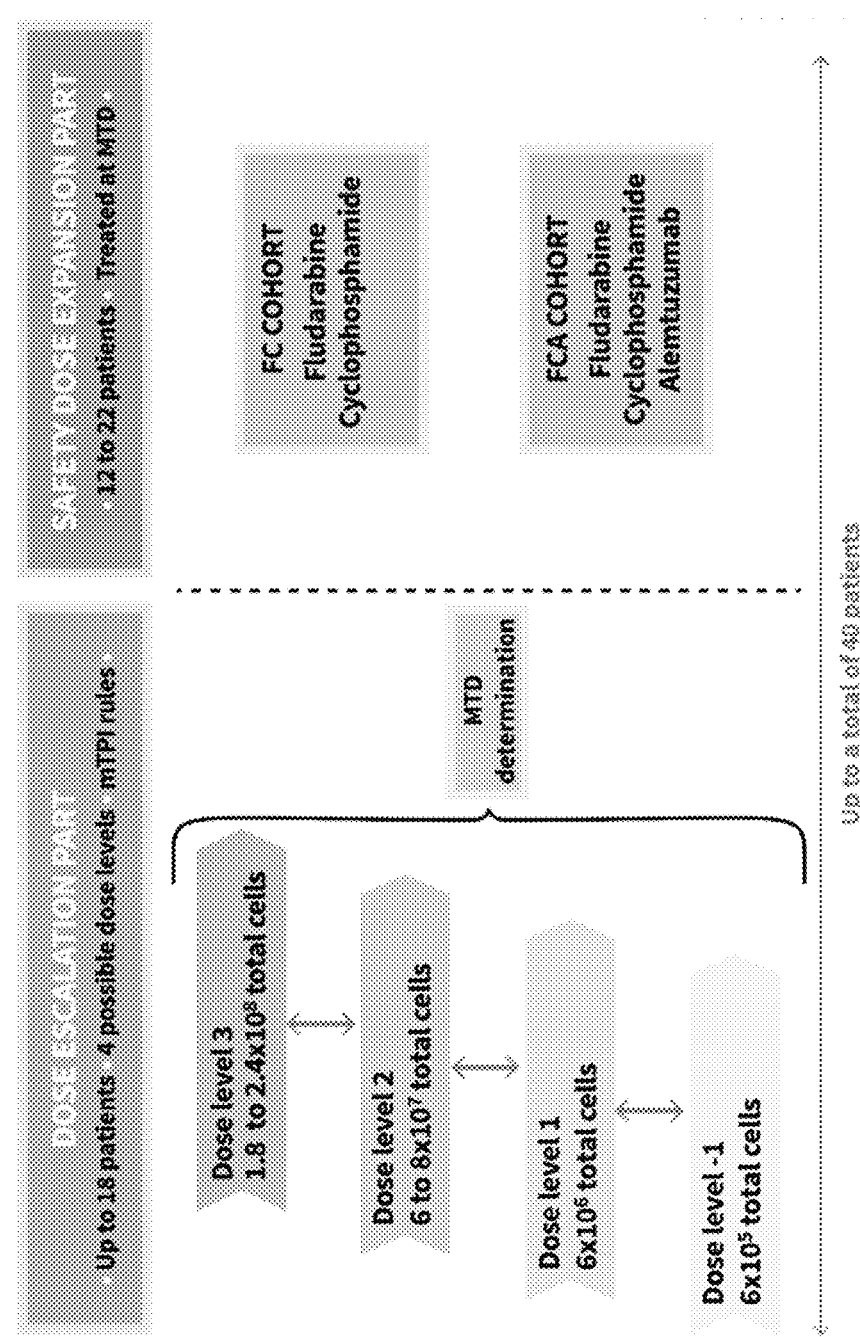
FIG. 3B depicts an exemplary schematic showing the steps of a dosing regimen for allogeneic CAR-T cell treatment.

FIG. 3B shows the study plan, having the following features:

Dose-escalating, open-label, non-comparative study, to evaluate up to 4 dose levels (DL) of UCART19 and to determine the maximum tolerated dose (MTD) in adult patients with R/R (relapsed/refractory) B-ALL.

Dose-escalation is followed by a safety expansion part, patients dosed at MTD or at the recommended dose (RD)

The lymphodepletion (LD) regimen starts from D-7 preceding UCART19 infusion and combines: cyclophosphamide 1500 mg/m$^2$ and fludarabine 90 mg/m$^2$, without CD52 antibody (FC) or with CD52 antibody 1 mg/kg (FCA)

During the expansion part, the role of the CD52 antibody may be investigated in 2 cohorts of patients (LD with FC or FCA)

At D0, UCART19 is administered as a single non-split dose, by slow IV infusion (5 minutes)

Evaluation of dose limiting toxicities is performed 28 days after infusion (D28)

Bone marrow aspiration/biopsy is performed before LD, at D-1, at D28 and D84

Minimal residual disease (MRD) is defined by <10-4 blasts in bone marrow, assessed by flow cytometry (FLC) and/or by qPCR At study completion (D84 after infusion), the patient is rolled-over to the long term follow-up study (LTFU) for a 15-year duration Key eligibility criteria for this study included:

Age ≥16 years old, up to <70 (male or female)

Patient with CD19$^+$ relapsed or refractory (relapsed/refractory; R/R) B-ALL, as per National Comprehensive Cancer Network guidelines (NCCN, 2017)

Morphological or MRD$^+$ (≥1×10$^{-3}$ by flow cytometry and/or qPCR)

Who have exhausted available treatment options

No previous treatment with investigational gene or cell therapy products

No clinically suspected extra-medullary involvement

Adequate renal, hepatic, pulmonary and cardiac function

No active infection

No active CNS leukemia

Data presented here are for 12 patients treated, with six patients at the first dose level of 6×10$^6$ total cells (approximately 1×10$^5$ cells per kilogram) and six patients at the second dose level with 6 to 8×10$^7$ total cells (approximately 1×10$^6$ cells per kilogram). No patients yet were treated at the third and final dose level of 1.8 to 2.4×10$^8$ total cells. The majority of the patients received three or greater lines of prior treatment, with three having received a prior treatment of blinatumomab, and seven having received a prior treatment of allo-SCT (allogeneic stem-cell transplant), reflecting clinical practice in Europe where 10 of the 12 patients were enrolled.

Patient characteristics are presented below in Table 8.

TABLE 8

| Patient Characteristic | All (N = 12) |
|---|---|
| Median age in years (range) | 29.50 [18-62] |
| Nb of prior treatment lines | |
| 1 or 2 | 4 |
| ≥3 | 8 |
| Incl. prior inotuzumab ozogamicin | 6 |
| Incl. prior blinatumomab | 3 |
| Previous allo-SCT | 7 |
| Time of relapse following previous allo-SCT | |
| <6 months | 4 |
| ≥6 months | 3 |
| Median (range) | 5.9 months (4.1-11) |
| Bone marrow blasts prior to lymphodepletion | |
| <5% | 3 |
| 5-25% | 3 |
| >25% | 6 |
| Median (range) | 34% (0-98) |

Safety

All 12 enrolled patients received UCART19 at the target cell dose following lymphodepleting chemotherapy consisting of cyclophosphamide and fludarabine, with 10 patients receiving CD52 antibody, (FCA regimen), and two patients not receiving CD52 antibody, (FC regimen). Table 6 below summarizes the adverse events by grade related to UCART19 infusion as well as those related to the lymphodepletion regimen. Grade 1 represents mild toxicity, grade 2 represents moderate toxicity, grade 3 represents severe toxicity and grade 4 represents life threatening toxicity. Grade 5 toxicity represents toxicity resulting in death.

TABLE 9

| N = 12 | Worst Grade | | | | | |
|---|---|---|---|---|---|---|
| | G1 n (%) | G2 n (%) | G3 n (%) | G4 n (%) | G5 n (%) | All grades n (%) |
| AEs related to UCART19 | | | | | | |
| Cytokine release syndrome | 1 (8.3) | 8 (66.7) | 1 (8.3) | 1 (8.3) | — | 11 (91.7) |
| Neurotoxicity events | 3 (25.0) | — | — | — | — | 3 (25.0) |
| Graft-versus-host disease in skin | 1 (8.3) | — | — | — | — | 1 (8.3) |
| AEs related to lymphodepletion and/or UCART19 | | | | | | |
| Prolonged cytopenia[1] | — | — | — | 3 (25.0) | — | 3 (25.0) |
| Neutropenic sepsis | — | — | — | 1 (8.3) | 1 (8.3) | 2 (16.7) |
| CMV infection | — | 3 (25.0) | — | — | — | 3 (25.0) |
| Adenovirus infection | 1 (8.3) | — | 1 (8.3) | — | — | 2 (16.7) |

[1]Persistent grade 4 neutropenia and/or thrombocytopenia beyond day 42 post UCART19 infusion, except if >5% bone marrow blasts; n: number of patients with at least one event by worst grade.

The most common UCART19 related adverse event was CRS, reported in 11 patients (two patients experiencing severe cases of CRS, one grade 3 and one grade 4). Tocilizumab was administered in 6/11 patients. CRS correlated with serum cytokine increase (IL-6, IL-10 and IFNgamma) and UCART19 expansion in blood in all patients.

Viral reactivations (CMV and/or adenovirus) occurred in 4 patients (G1 to G3).

Three patients developed prolonged cytopenia, defined as persistent cytopenia beyond day 42 after UCART19 infusion.

Three patients experienced mild, or grade 1, neurotoxicity events.

One patient experienced grade 1 GvHD adverse event of the skin, which resolved with topical steroids.

Two dose limiting toxicities were reported. The first case occurred at the first dose level and was a grade 4 CRS related to UCART19, and associated with grade 5 neutropenic sepsis related to lymphodepletion and UCART19. Death occurred on day 15 after UCART19 infusion. The second case, a grade 4 prolonged cytopenia, occurred at the second dose level and was reported as related to both lymphodepletion and UCART19. This patient underwent allo-SCT and had an unrelated grade 5 pulmonary hemorrhage in the setting of infection on day 19 following allo-SCT or day 82 after UCART19 infusion. Grade 5 adverse events have been reported in other autologous anti-CD19 CAR T cell therapy trials in part due to advanced stage of disease and accompanying confounding conditions.

Two additional deaths have also been reported that were not attributed to UCART19. One patient died from progressive disease, and one patient from allo-SCT related complications. Transplant related mortality occurs in approximately 20-30% of patients following allo-SCT.

Efficacy

Figure 7A:
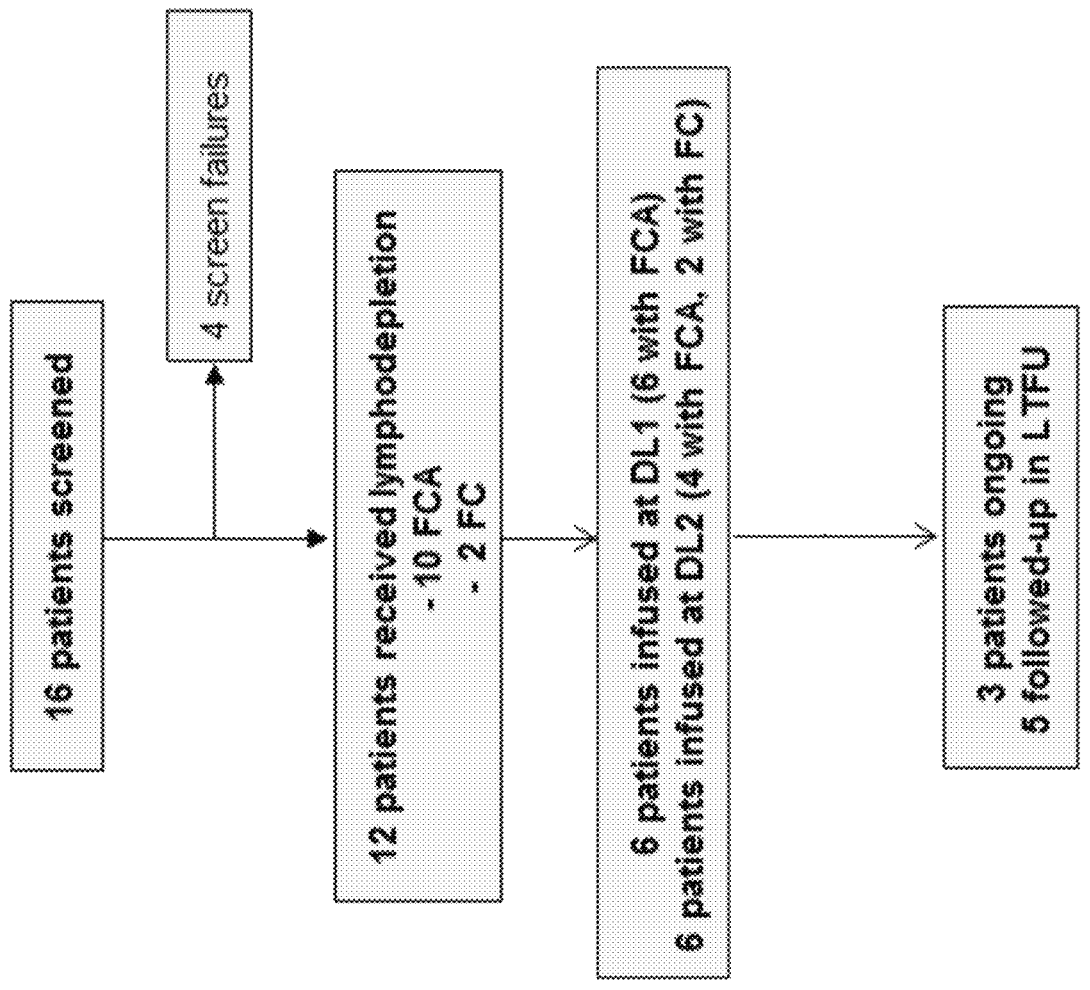
FIG. 7A depicts the study status, following the initiation of the use of an allogeneic anti-CD19 CAR-T cell product (UCART19) in adult patients with CD19+ relapsed/refractory B-cell acute lymphoblastic leukemia.
Figure 7B:
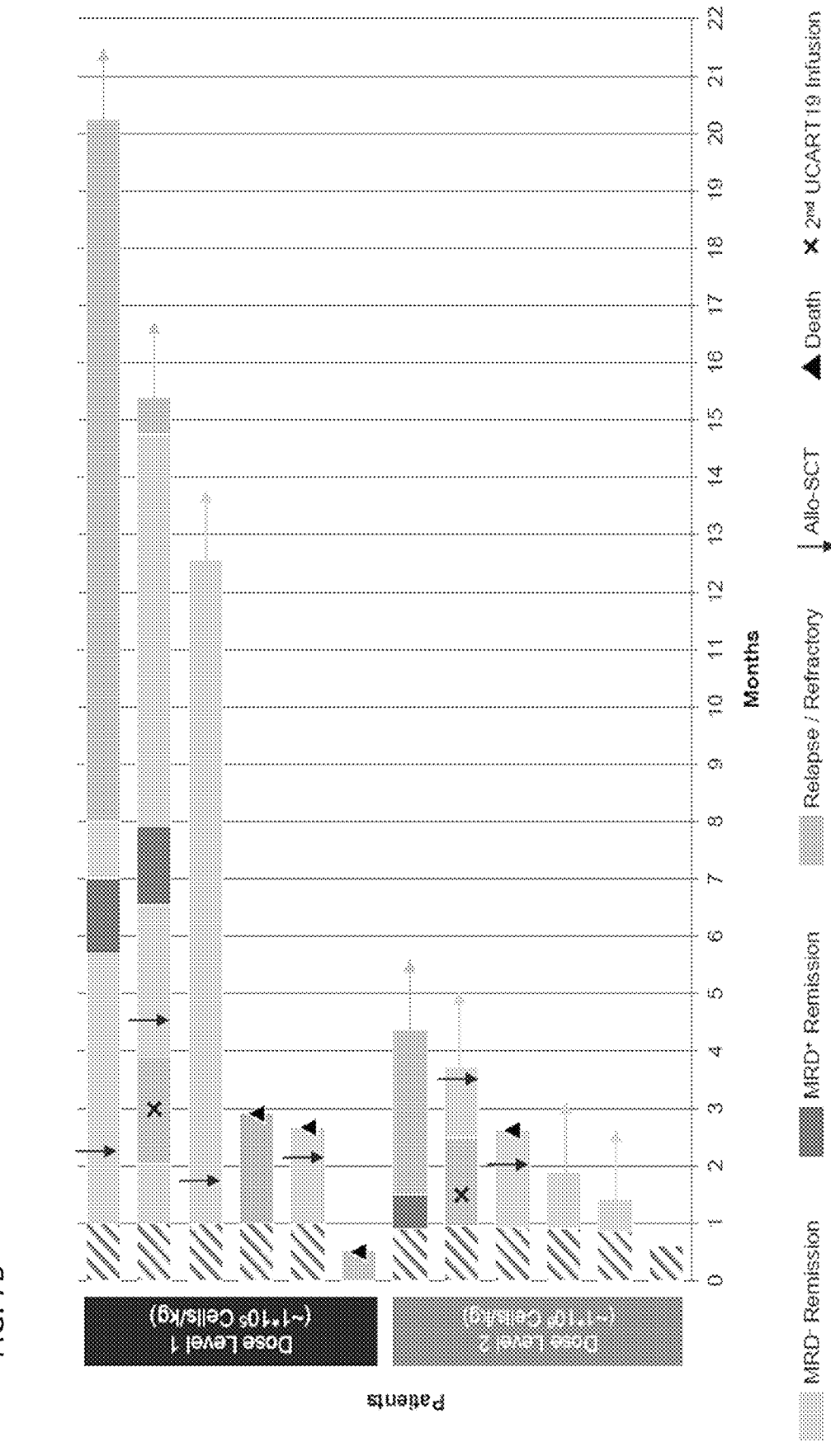
FIG. 7B depicts response, duration of remission and re-dosing of UCART19 in adult patients with CD19+ relapsed/refractory B-cell acute lymphoblastic leukemia.

FIG. 7A shows the study status. FIG. 7B illustrates response, duration of remission and re-dosing of UCART19 in this trial (anti-leukemic activity).

MRD-CR occurs when a patient achieves a CR and there is no evidence of ALL cells in the marrow when using sensitive tests such as polymerase chain reaction or flow cytometry. CR or CRi rates are the typical regulatory standard, but studies in both children and adults with ALL have demonstrated a strong correlation between minimal residual disease (MRD+) and risks for relapse.

Of the 12 patients dosed with UCART19, two were not able to be evaluated (one died at day 15, as noted above, and one had not reached the day 28 evaluation as of the data collection). Eight out of the 10 evaluable patients achieved a CR, defined as the absence of any evidence or symptoms of cancer, or CR with incomplete blood count recovery (CRi). Seven patients achieved MRD-CR.

Those 2 patients with refractory disease had no UCART19 expansion.

Six patients proceeded to an allo-SCT, including four patients after the first dose of UCART19, and two patients after the second dose. As of the data collected here, four patients remained in MRD-CR at 12.4, 3.6, 1.8 and 1.3 months after UCART19 infusion (molecular remission).

CAR T cell expansion was detected in blood from day 7 after UCART19 infusion, reaching the peak expansion between day 10 and day 17. One patient at the second dose level showed the highest peak linked to a long persistence up to day 42 still ongoing at the data cutoff. At dose level two, the longest persistence observed as of the data cutoff occurred on day 56.

The two patients on the FC regimen showed no evidence of CAR-T cell expansion. A similar lack of CAR-T cell expansion was seen in two out of 10 patients on the FCA regimen.

Figure 8A:
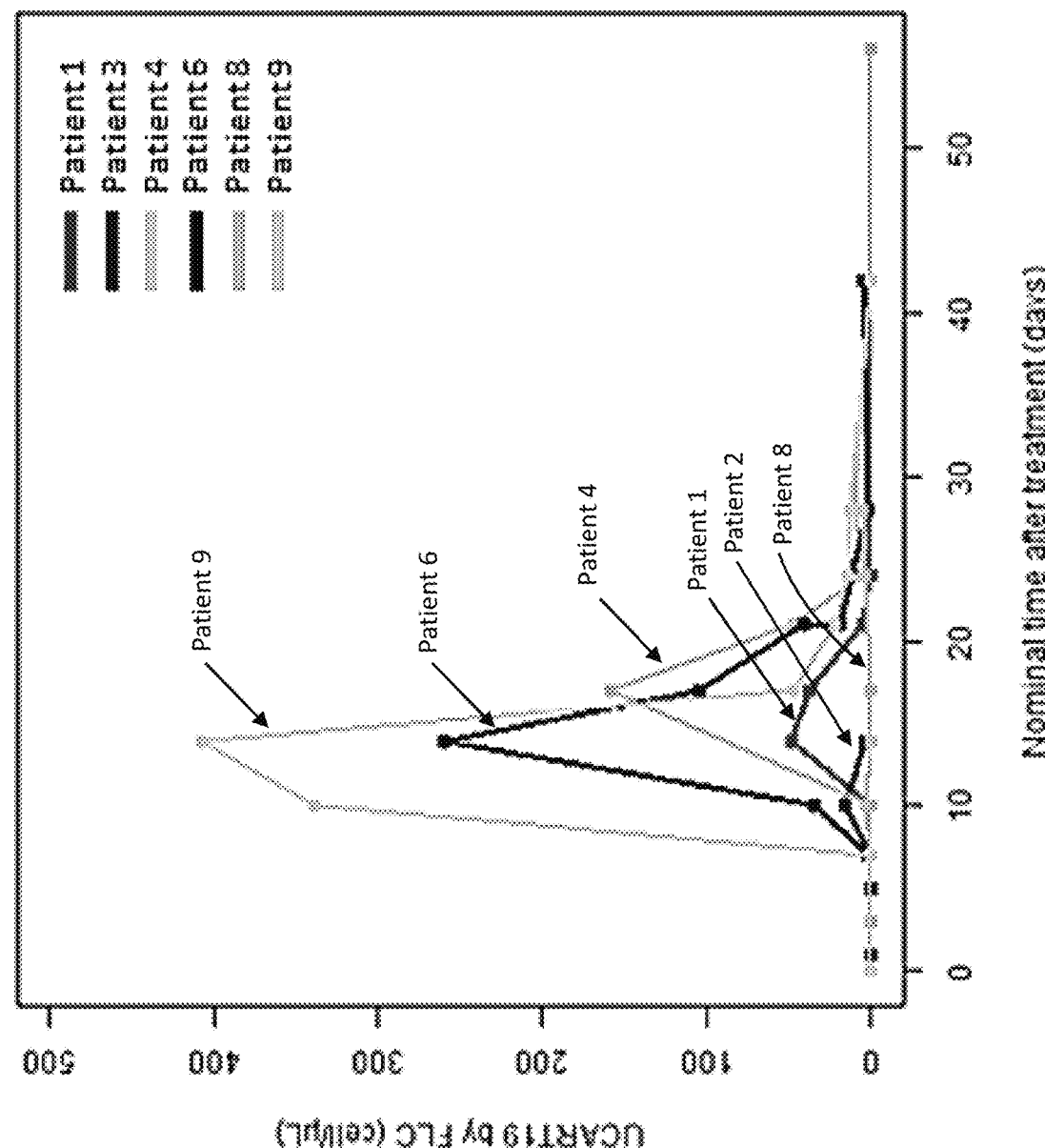
FIG. 8A and FIG. 8B depict the flow cytometry PK profile and UCART19 kinetics in adult patients with CD19+ relapsed/refractory B-cell acute lymphoblastic leukemia.
Figure 8B:
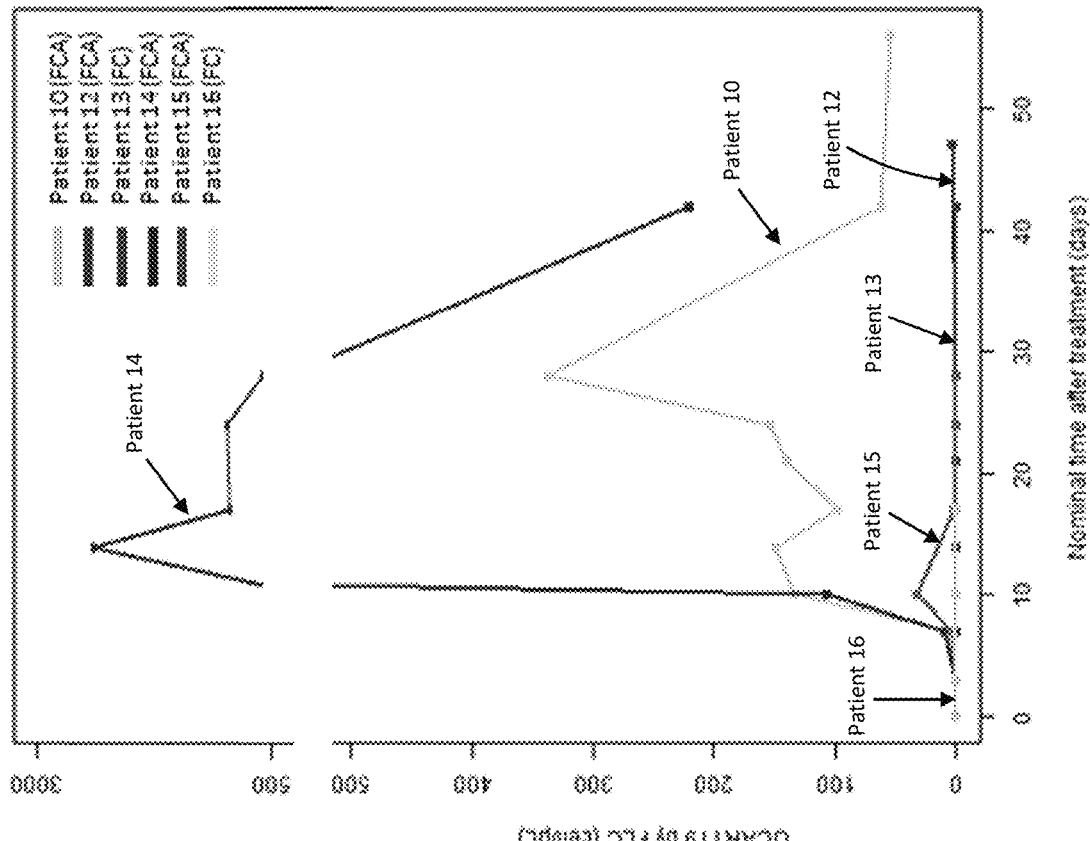

FIG. 8A and FIG. 8B show the flow cytometry PK profile and UCART19 kinetics in adult patients with CD19+ relapsed/refractory B-cell acute lymphoblastic leukemia. Specifically, referring to FIG. 8A and FIG. 8B, preliminary data on flow cytometry at DL1 and DL2 show that UCART19 was detectable in blood from D3 to D14 with a proliferation peak between D10 and D17. One patient at DL2 showed the highest peak linked to longest persistence. Among those patients with cell expansion, at DL1: 1 patient showed UCART19 persistence up to D42; at DL2: 2 patients showed persistence up to D42 and ongoing persistence at D56. Preliminary data indicate that the level of UCART19 expansion does not correlate with response on D28; instead, MRD-CR at D28 was observed even with low levels of UCART19 expansion. After the first dose of UCART19, no expansion was observed in 2 out of 10 patients who received LD with FCA and 2 out of 2 patients who received FC.

The role of CD52 antibody in UCART19 expansion is also being evaluated.

Example 3: Re-Dosing of UCART19 in a Patient with Relapsed/Refractory CD19 Positive B-ALL This example illustrates treatment with UCART19, wherein the treatment comprises a subsequent dose of UCART19 administered after a first dose of UCART19, as administered in Example 2.

Two patients from the above study in Example 2 received a second dose of UCART19 and both achieved MRD-CR.

Patient #4:

A 23 year old male patient with relapsed/refractory CD19 positive B-ALL received a single dose of UCART19 ($6\times10^6$ total cells, Dose DL1) at day 0 (D0) in the study. A lymphodepletion regimen (fludarabine 122 mg/m$^2$; cyclophosphamide 1230 mg/m$^2$; and CD52 antibody 1 mg/kg) was administered over a period of six days prior to UCART19 infusion. No major toxicity was observed. This patient had relapsed with CD19+ disease at D61 following 1st dose (LD with FCA); the 2nd dose (LD with FC) allowed this patient to achieve MRD- at D28. The patient then received a reduced intensity lymphodepletion regimen over a period of six days (fludarabine and cyclophosphamide without CD52 antibody). At 99 days post initial UCART19 infusion, the patient was re-dosed with the same dose ($6\times10^6$ total cells) of UCART19.

Figure 2A:
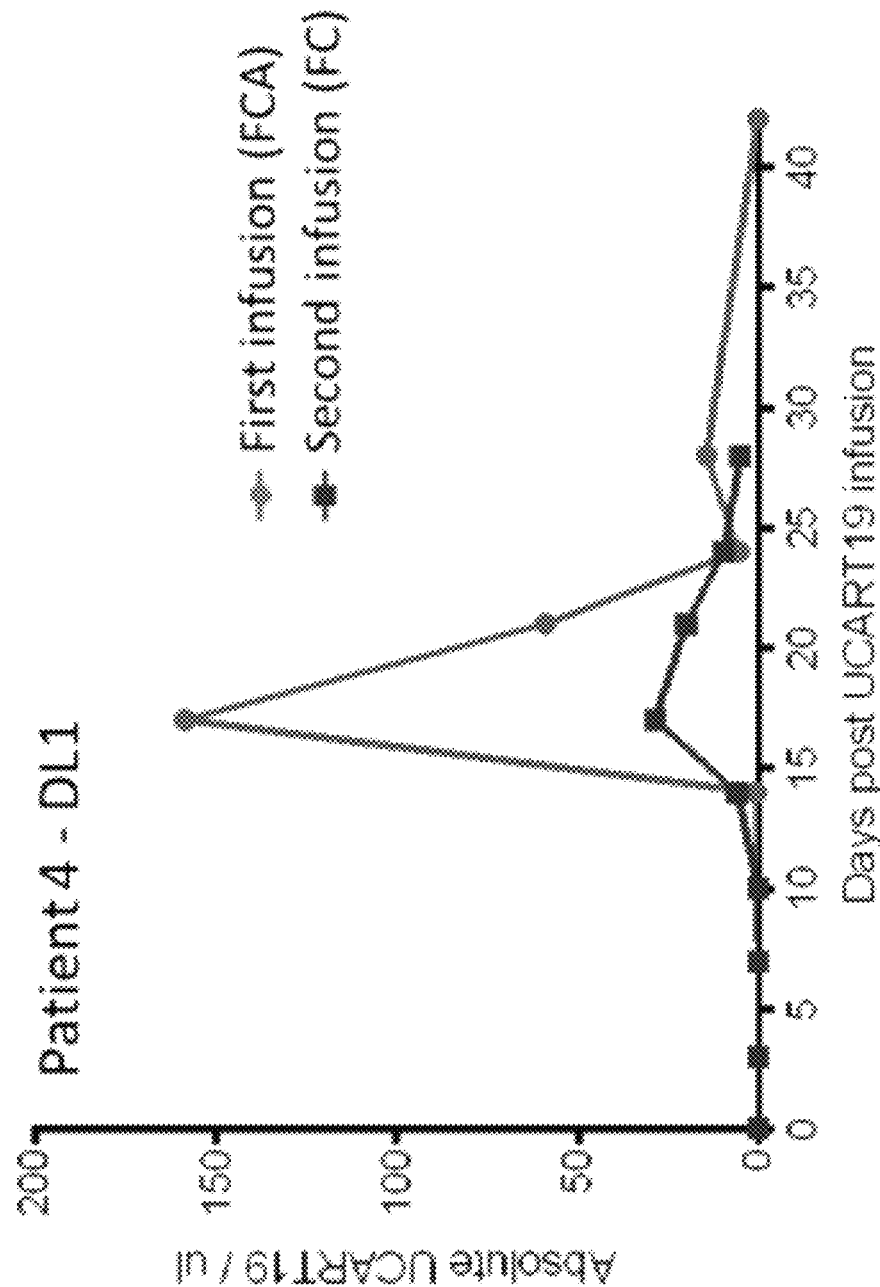
FIG. 2A and FIG. 2B depict kinetic data from two patients receiving a second UCART19 infusion (redosing study).

Data are shown in the graph in FIG. 2A. At the time just prior to administration of the subsequent dose of UCART19, UCART19 was not detectable in the patient (FIG. 2A).

The patient achieved MRD negativity at D28 after infusion of the second dose of UCART19. Thus, dosing of UCART19 after relapse after molecular remission after treatment with a first dose of UCART19 was effective to achieve MRD negativity. Patient proceeded to allogeneic stem cell transplantation 6 weeks after the second dose.

Figure 2B:
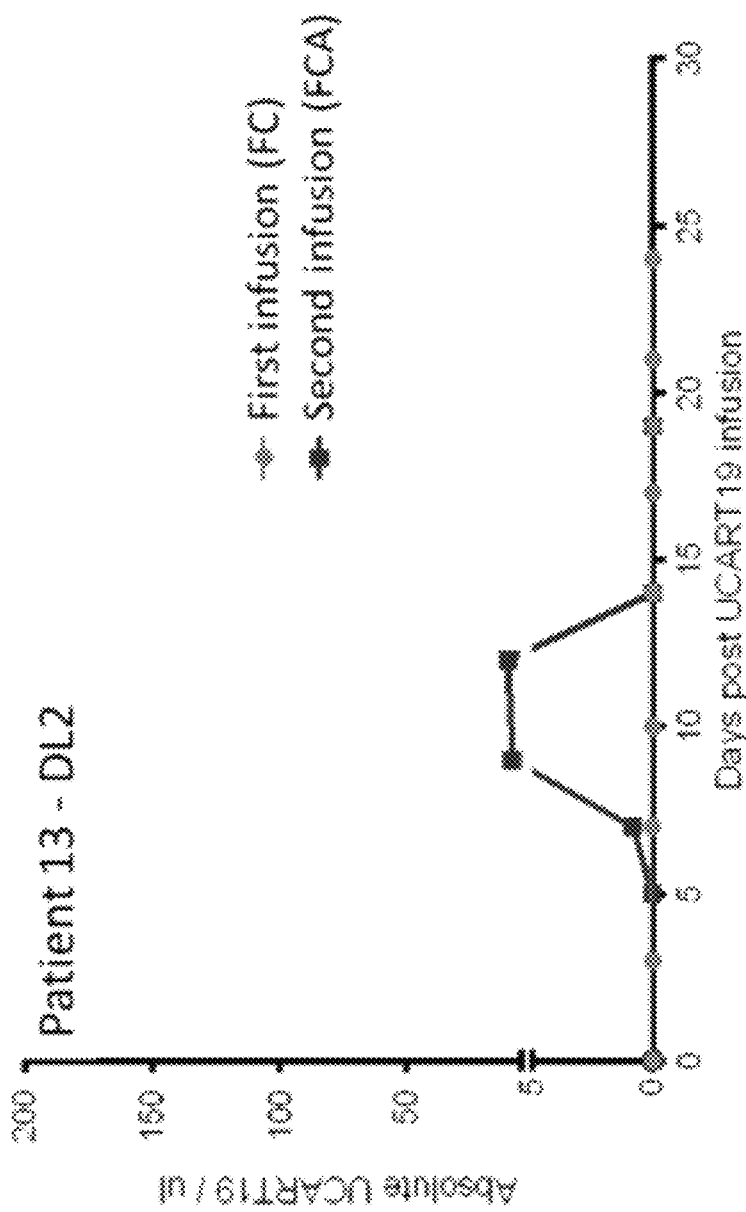
Figure 14:
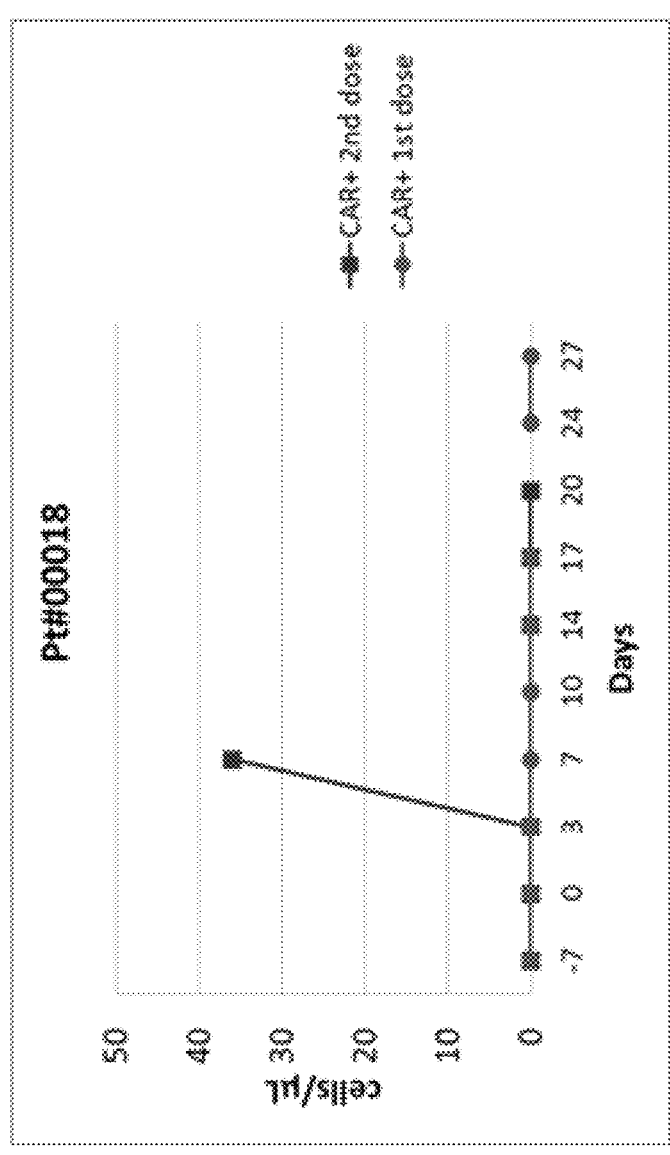
FIG. 14 shows the response of Patient #18 to redosing, as described in Example 3.

Patient #13:

Male patient, 31 years old, refractory B-ALL diagnosis. Patient received the 1st infusion of UCART19; dose received from was $8\times10^7$ total cells (dose level 2), after a lymphodepletion combining fludarabine (90 mg/m$^2$ total dose) and cyclophosphamide (1500 mg/m$^2$ total dose) (FC). After 1st dosing: no UCART19 were detectable (<1 cells/μL by flow cytometry). At Day 28 (28 days post UCART19 infusion), no anti-leukemic activity was observed (89% of blasts in the bone marrow). No mechanism of action related toxicity was reported within 28 days post UCART19 infusion. Patient was withdrawn from the study and received a second UCART19 infusion (total dose $8×10^7$ total cells) (48 days after the first dose), under compassionate use ("Specials" in UK). The lymphodepletion combined fludarabine (90 mg/m² total dose), cyclophosphamide (1500 mg/m² total dose) and CD52 antibody (1 mg/kg total dose) (FCA). Patient presented a low level of UCART19 expansion (10 cells/µL) at Day 10, no UCART19 detectable after D14. A low grade CRS was reported. An antileukemic activity was observed at Day 14 and D28 with negative minimal residual disease (MRD negative) by flow cytometry and by qPCR. Patient underwent an allo transplant (63 days after the second dose). He eventually relapsed on 15 Aug. 2018 (112 days after transplant), with a low level of MRD detected (molecular relapse). Patient is still alive 9.3 months after the first dose of UCART19 and 7.8 months after the second dose of UCART19. Data are shown in FIG. 2B.f Both patients proceeded subsequently to an allo-SCT Patient #18:

Male patient, 22 years old, B-ALL diagnosis. Patient received the 1st infusion of UCART19 of $1.8×10^8$ cells (dose level 3) after a lymphodepletion combining fludarabine (90 mg/m² total dose), cyclophosphamide (1500 mg/m² total dose) and CD52 antibody (40 mg total dose) (FCA). No UCART19 were detectable and no mechanism of action related toxicity was reported. At Day 28 (28 days post UCART19 infusion), no anti-leukemic activity was observed (medullary biopsy presented 15% blasts). Patient was refractory and received a second UCART19 infusion (75 days after the first dose) with an intensified lymphodepleting regimen fludarabine (120 mg/m² total dose), cyclophosphamide (1500 mg/m² total dose) and CD52 antibody (1 mg/kg total dose=65 mg) (FCA). Patient remained in the study as the re-dosing was allowed per amended protocol. A peak of UCART19 expansion was observed at Day 7, with UCART19 detectable at Day 10 (10 cells/µL) and no UCART19 detectable from Day 14. At Day 28 after the second dose, the patient did not respond and progressed. The response of Patient #18 to redosing is shown in FIG. 14.

This result demonstrate re-dosing with allogeneic CAR-T is effective achieve MRD negativity after relapse.

Example 4: Use of an Allogeneic Anti-CD19 CAR-T Cell Product (UCART19) in High-Risk Pediatric Patients with CD19+ Relapsed/Refractory B-Cell Acute Lymphoblastic Leukemia B-cell acute lymphoblastic leukemia is the most common malignant disease in children and accounts for 80% of childhood leukemias. The most common between age is 2-10 years (peaks at 3-4 years), survival is ~90%. Relapse can occur in 10% of children, with about 40%-50% surviving, unless high risk, in which case about 10%-30% survive.

The same UCART19 provided in Example 2, was used in this study.

This study had at least the following objectives:

Evaluation of safety and tolerability of UCART19 at a fixed dose.

Assessment of the ability of UCART19 to induce molecular remission at D28, D56, D84, and/or ahead of allo-SCT condition regimen initiation.

Assessment of the remission rate, duration of remission, time to remission, disease-specific survival, and progression free survival.

Assessment of the proportion of patients who underwent allo-SCT.

Evaluation of the phenotype, trafficking, expansion and persistence of UCART19.

Key eligibility criteria for this study included:

Age between 6 months and <18 years old (male or female)

Patient with CD19+R/R B-ALL Morphological or MRD+ ($\geq 1×10^{-3}$ by flow cytometry and/or qPCR)

Who have exhausted available treatment options

Eligible for allo-SCT with suitable donor available

No previous treatment with investigational gene or cell therapy products

No active infection

No active CNS leukemia

Figure 9:
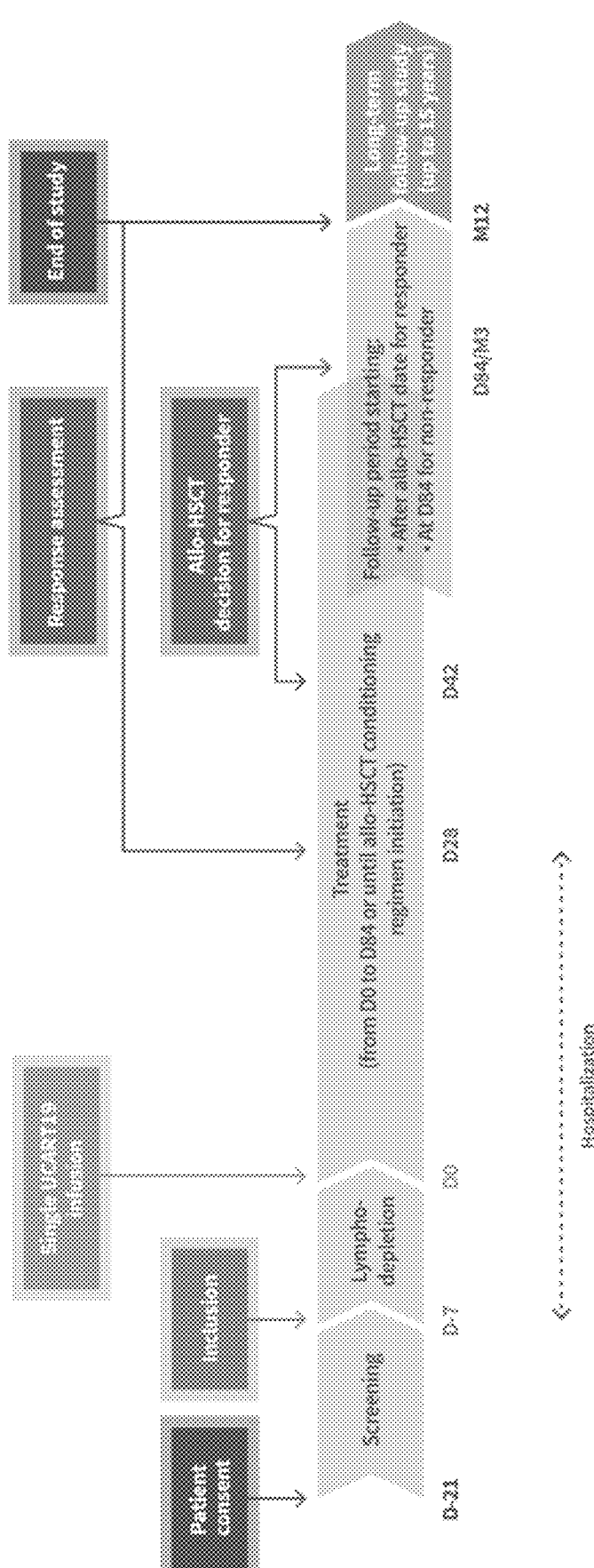
FIG. 9 depicts a study design for the use of an allogeneic anti-CD19 CAR-T cell product (UCART19) in high-risk pediatric patients with CD19+ relapsed/refractory B-cell acute lymphoblastic leukemia.

FIG. 9 shows the study design.

The lymphodepletion regimen started from D-7 (during the week preceding UCART19 infusion) and combined: cyclophosphamide (C) (60 mg/kg/day for 2 days), fludarabine (F) (30 mg/m²/day for 5 days), and w/wo CD52 antibody (A) (0.2 mg/kg/day for 5 days). At D0, a flat dose of UCART19 ($2×10^7$ total cells equivalent to 1.1 to $2.3×10^6$ cells/kg) was administered as a single non-split dose, by slow IV infusion over 5 minutes.

Safety assessment was performed at D28 post UCART19 administration. BMA was performed at baseline, D-1, D14 (optional), D28, D56, D84 or ahead of allo-SCT conditioning regimen initiation or at the withdrawal visit (at the investigator's discretion). During the 12-month follow-up period, a BMA will be performed at M1, M2, M3, M6 and M12 post allograft for the disease assessment. For refractory patients, the BMA will be performed optionally according to investigator's judgment.

Results

Six patients were enrolled. The six patients had been treated at a weight-banded cell dose equivalent to 1.1 to $2.3×10^6$ cells/kg. Five patients had three or greater lines of prior treatment, with three having received four or greater lines of prior treatment. Two patients had received a prior treatment of allo-SCT. Patient characteristics are presented below in Table 10.

TABLE 10

| Patient Characteristic | All (N = 6) |
|---|---|
| Median age in yrs (range) | 3.75 [0.8-16.4] |
| Disease at screening | |
| B-ALL relapsed | 6 |
| Disease at diagnosis | |
| NOS | 4 |
| With t(12;21)(p13;q22) TEL-AML1 (ETV6-RUNX1) | 1 |
| With t(v;11q23);MLL rearranged | 1 |
| Nb of prior treatment lines | |
| 2 prior treatment lines | 1 |
| 3 prior treatment lines | 2 |
| ≥4 prior treatment lines | 3 |
| Previous inotuzumab ozogamicin | 2 |
| Previous allogeneic stem cell transplantation (SCT) | 2 |
| Time of relapse following previous SCT | |
| >6 months | 2 |
| Bone marrow blasts at inclusion | |
| <10% | 5 |
| >50% | 1 |

Safety

All six enrolled patients received UCART19 at the target cell dose following lymphodepleting chemotherapy consisting of cyclophosphamide and fludarabine. Five patients also received CD52 antibody. Table 11 below summarizes the adverse events by grade related to UCART19 cell infusion as well as those related to the lymphodepletion regimen and/or UCART19. [Grade 1 represents mild toxicity, grade 2 represents moderate toxicity, grade 3 represents severe toxicity and grade 4 represents life threatening toxicity. Grade 5 toxicity represents toxicity resulting in death.]

TABLE 11

| N = 6 | Worst Grade | | | | | |
|---|---|---|---|---|---|---|
| | G1 n (%) | G2 n (%) | G3 n (%) | G4 n (%) | G5 n (%) | All Grades n (%) |
| AEs related to UCART19 | | | | | | |
| Cytokine release syndrome | 1 (16.7) | 4 (66.7) | 1 (16.7) | — | — | 6 (100.0) |
| Neurotoxic events | 2 (33.3) | 1 (16.7) | — | — | — | 3 (50.0) |
| Graft-versus-host disease in skin | 1 (16.7) | — | — | — | — | 1 (16.7) |
| AEs related to lymphodepletion and/or UCART19 | | | | | | |
| Prolonged cytopenia[1] | — | — | — | 3 (50.0) | — | 3 (50.0) |
| BK virus hemorrhagic cystitis | — | — | 2 (33.3) | — | — | 2 (33.3) |
| Metapneumovirus infection | — | — | — | 1 (16.7) | — | 1 (16.7) |
| CMV infection | — | — | 1 (16.7) | — | — | 1 (16.7) |
| Febrile neutropenia | — | — | 1 (16.7) | — | — | 1 (16.7) |
| Adenovirus infection | 1 (16.7) | — | — | — | — | 1 (16.7) |

[1]Persistent grade 4 neutropenia and/or thrombocytopenia beyond day 42 post UCART19 infusion The most frequent adverse events related to UCART19 were CRS in all treated patients, with one patient experiencing grade 3 CRS. Mild-to-moderate neurotoxic events occurred in three of the six treated patients. Three patients experienced prolonged cytopenia, reported as related to lymphodepletion and in some cases possibly related to UCART19. Viral reactivation with cytomegalovirus (CMV), adenovirus, BK virus and metapneumovirus was attributed to lymphodepletion. One patient experienced transient grade 1 skin GvHD. Two patients died from disease recurrence following allo-SCT and one patient died from complications of allo-SCT. There were no treatment-related deaths. This is presented in Table 12.

TABLE 12

| | N = 6 |
|---|---|
| Time to onset (median and range in days) | 7 (5-9) |
| Duration (median and range in days) | 7.5 (4-13) |
| Cytokine elevation (IL-6, IFN-γ, IL-10, CRP) | 2 |
| Specific treatment | 2/6 |
| Tocilizumab | 2 |
| Outcome - Number of complete resolution | 6 |

Efficacy

Figure 10:
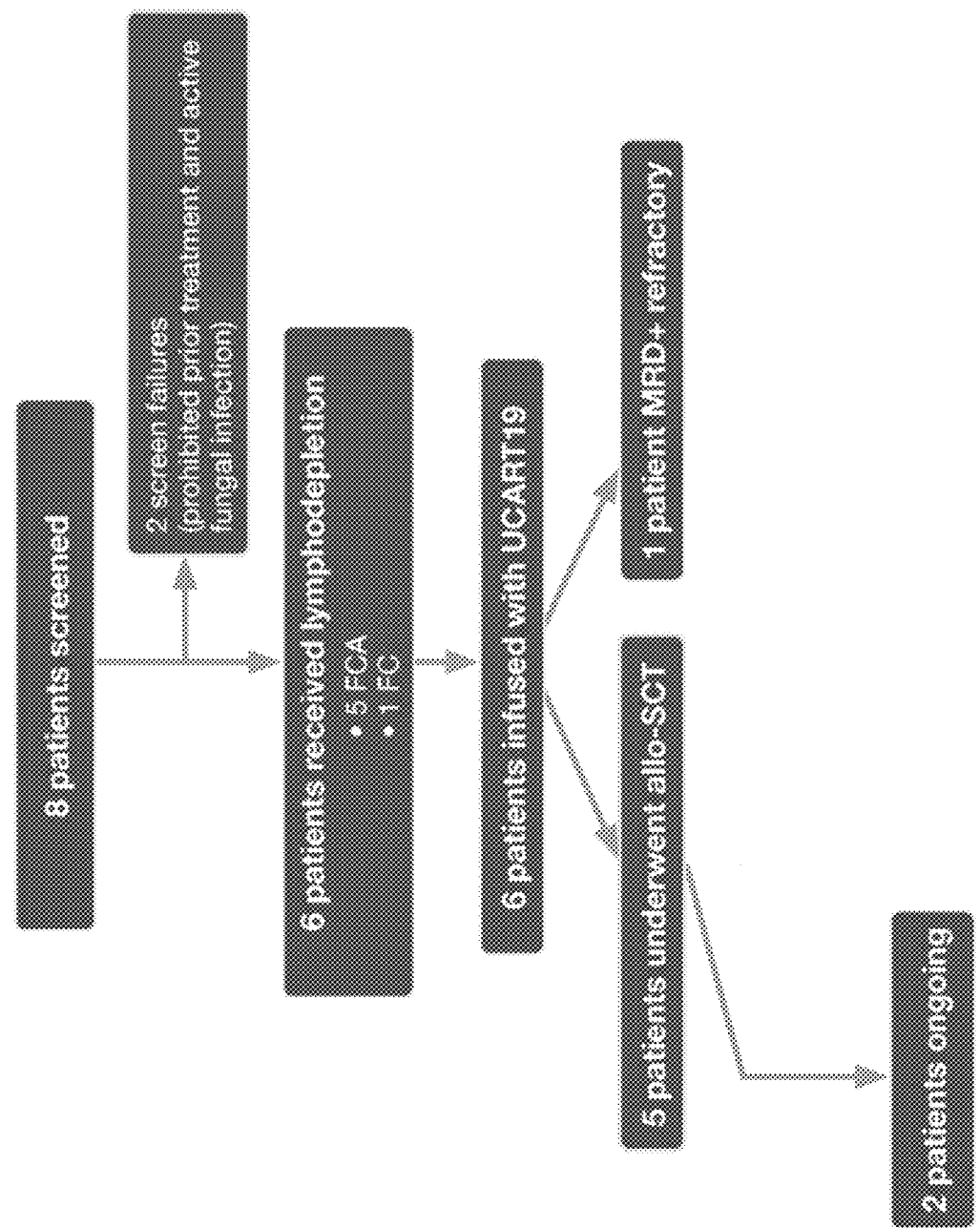
FIG. 10 depicts the study status, following the initiation of the use of an allogeneic anti-CD19 CAR-T cell product (UCART19) in high-risk pediatric patients with CD19+ relapsed/refractory B-cell acute lymphoblastic leukemia.
Figure 11:
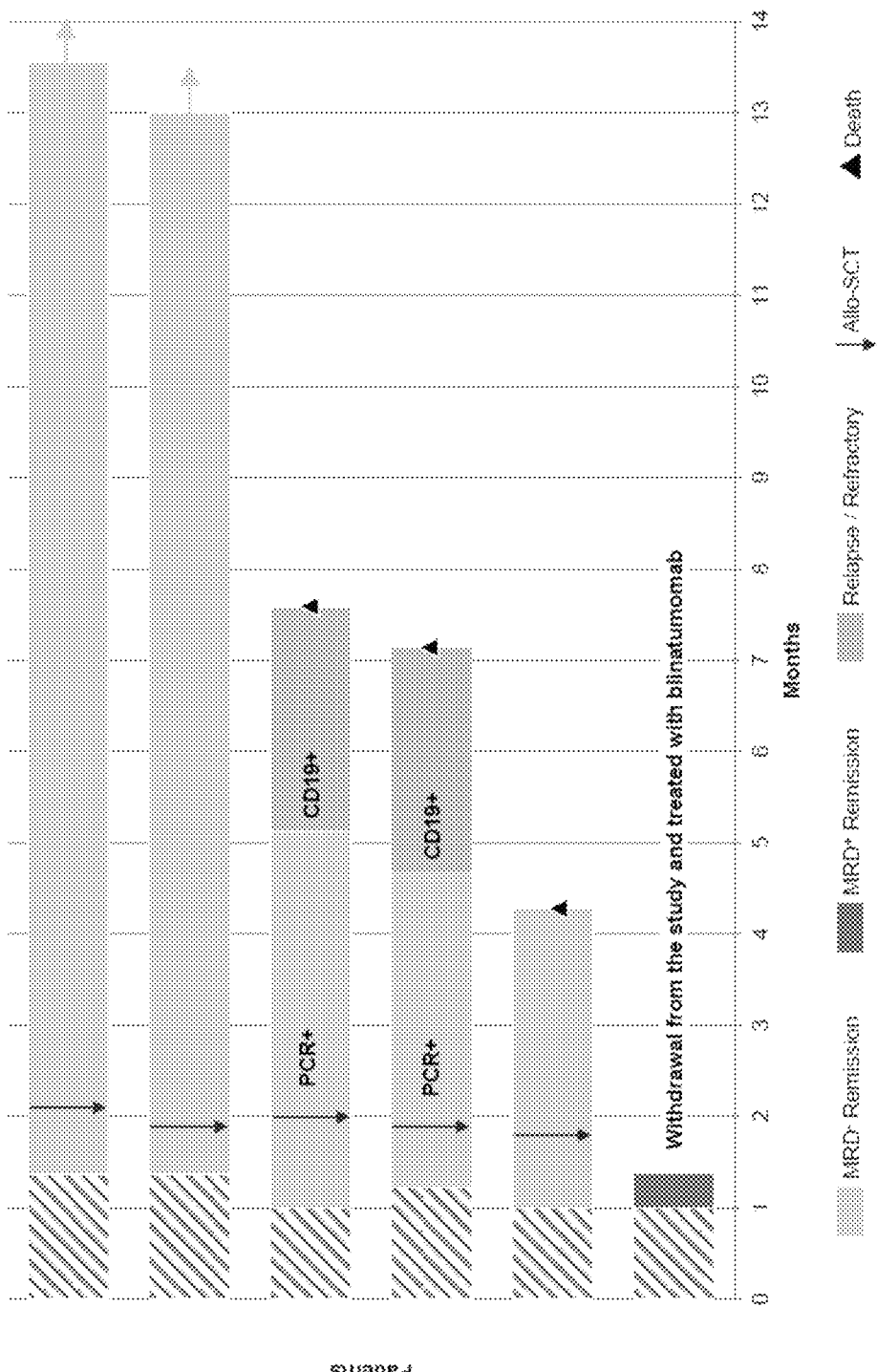
FIG. 11 depicts response and duration of remission (anti-leukemic activity) of UCART19 in high-risk pediatric patients with CD19+ relapsed/refractory B-cell acute lymphoblastic leukemia.

FIG. 10 shows the study status. FIG. 11 illustrates response and duration of remission (anti-leukemic activity).

All patients completed the 28-day evaluation period and were evaluable for anti-leukemic activity. Five of the six patients achieved MRD-CRs and all five underwent allo-SCT. Two patients were in remission greater than 13 months after UCART19 infusion, as of the data cutoff, and three patients died following allo-SCT, two due to disease recurrence, and one due to transplant-related complications. One patient withdrew from the study due to lack of response and received subsequent treatment with blinatumomab off-study. This is the only patient that received the FC regimen.

Figure 12:
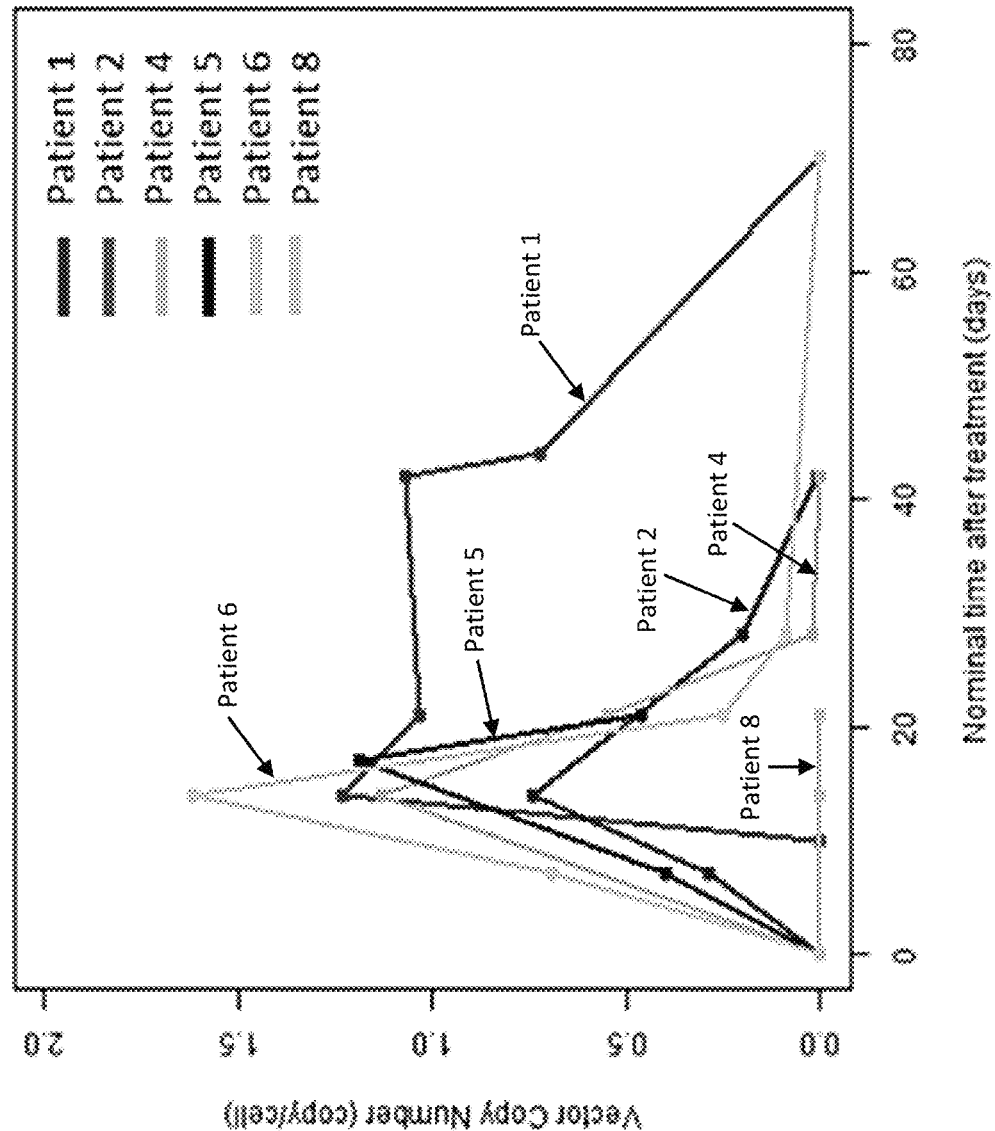
FIG. 12 depicts cellular kinetics following use of UCART19 in high-risk pediatric patients with CD19+ relapsed/refractory B-cell acute lymphoblastic leukemia.

Cellular kinetics were assessed, and shown in FIG. 12. UCART19 vector copy number (VCN) was measured in blood and bone marrow by qPCR. Preliminary data showed that for 5 out of 6 patients, UCART19 was detectable in blood by D7, with a proliferation peak observed around D14. No UCART19 was detected for one patient who subsequently relapsed. For 3 out of 5 patients, UCART19 persisted in blood until D28. For 2 out of 5 patients, UCART19 remained detectable in blood on D42. Persistence beyond D42 was not measured since UCART19 was eliminated by conditioning regimen for allo-SCT.

Cytokine kinetics were assessed. 2 out of 6 patients had IL-6 and IFNγ elevation. No cytokine elevation was observed in 4 out of 6 patients. All 6 patients experienced CRS. CRS G3 was observed in patient 1 and CRS G2 in patient 8. Time to onset of first CRS symptoms ranged between D5 and D9.

Figure 13A:
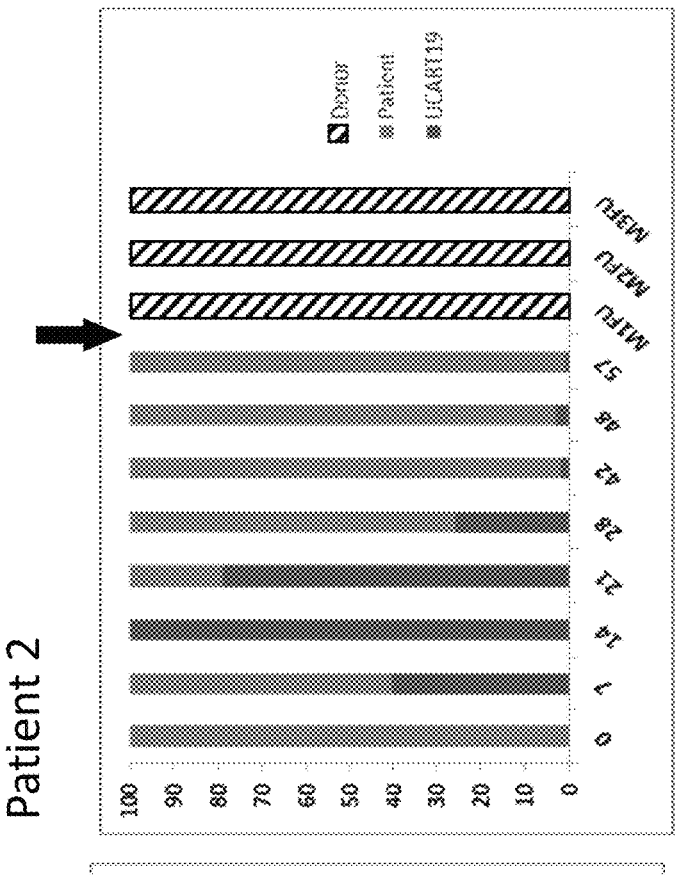
FIG. 13A, FIG. 13B, and FIG. 13C depict chimerism data in blood following use of UCART19 in high-risk pediatric patients with CD19+ relapsed/refractory B-cell acute lymphoblastic leukemia.
Figure 13A:
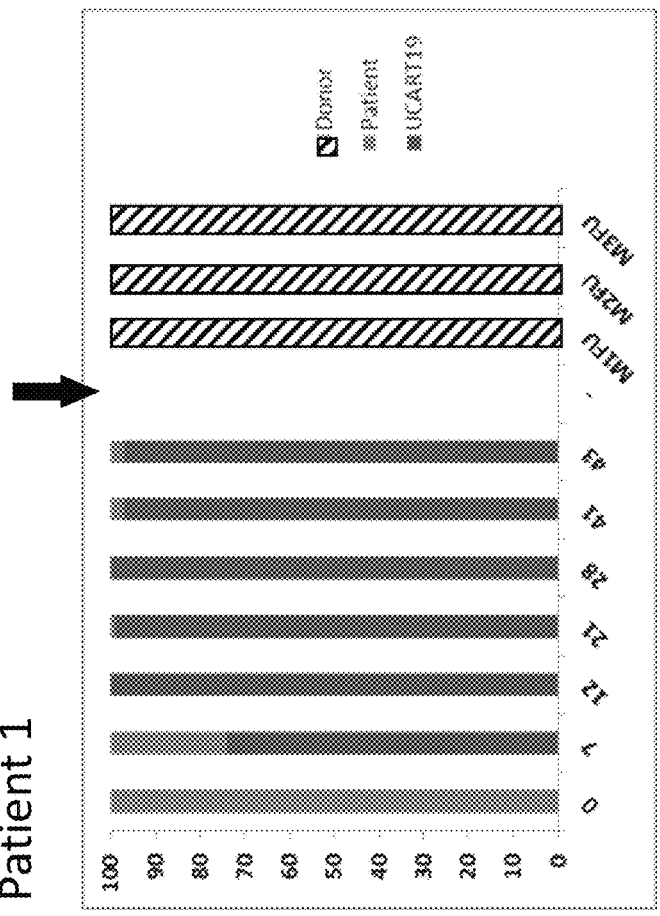
Figure 13B:
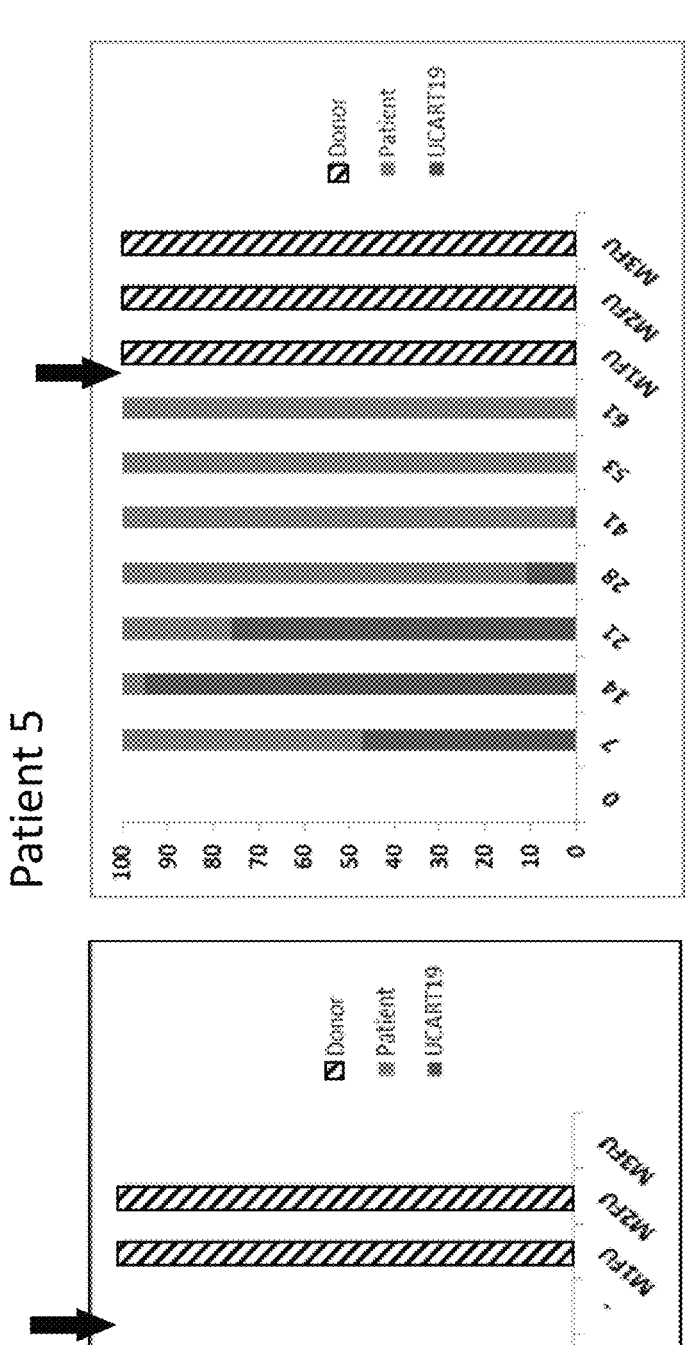
Figure 13C:
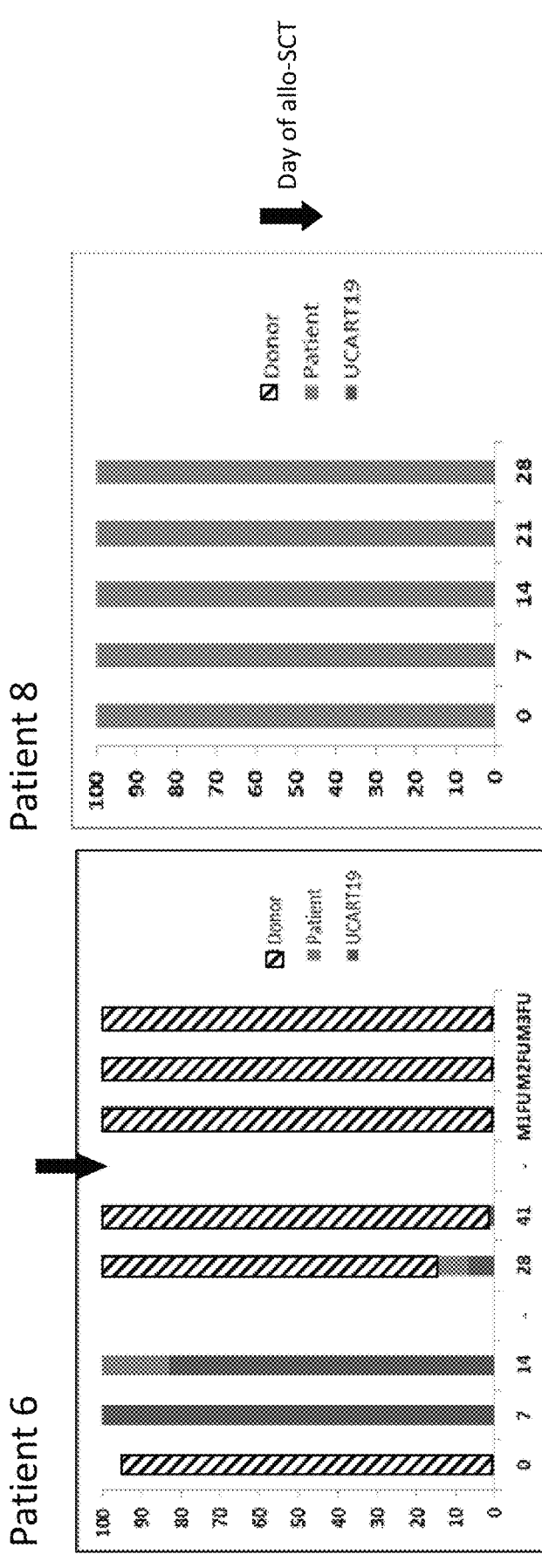

T-cell donor chimerism was assessed (FIG. 13A, FIG. 13B, FIG. 13C). UCART19 was detectable in blood from D7 to at least D42 in all patients but one by molecular signatures of T-cell donor chimerism.

Example 5: Use of an Allogeneic Anti-CD19 CAR-T Cell Product (UCART19) in Patients with Relapsed/Refractory Large B-Cell and/or Follicular Lymphoma Diffuse large B-cell lymphoma (DLBCL), which comprises 20% to 30% of B-cell Non-Hodgkin lymphoma (B-NHL), is fatal if not cured. Primary mediastinal large B-cell lymphoma (PMBCL) and transformed follicular lymphoma (FL) are typically treated along a DLBCL paradigm. DLBCL includes a group of molecularly diverse aggressive lymphomas that not only differ in their chromosomal alterations, but also signaling pathway activation and clinical outcome. The disease itself may be de novo or may result from transformation of indolent B-lymphomas such as from transformed follicular lymphoma. In the US, the annual incidence rate of DLBCL is 6.9 per 100,000 and it is the most common form of B-NHL.

Approximately half of all patients with aggressive B-NHL have relapsed or refractory disease, with an estimated 10% to 15% of patients with DLBCL having primary refractory disease and an additional 20-30% relapsing after an initial objective response (Chaganti et al, 2016). High-grade B-cell lymphomas with aberrations in MYC, BCL2 and/or BCL6, including "double hit" and "triple hit" lymphomas, are associated with an inferior prognosis, even in the newly diagnosed setting (Rosenthal and Younes, 2017).

This study will be a single-arm, open-label, multicenter Phase 1/2 study evaluating safety, efficacy, cellular kinetics, and pharmacodynamics of UCART19 in adult patients with relapsed/refractory large B-cell lymphoma or follicular lymphoma. The study is divided into a dose-escalation (Phase 1) and a dose-expansion phase (Phase 2). In Phase 1 of the study, CAR-T cells comprising an RQR8 safety switch will be used (CD19CAR/RQR8+_TCRαβ-_T-cells). In Phase 2 of the study, it one or more patients may receive CAR-T cells that do not comprise an RQR8 safety switch (CD19CAR/TCRαβ-_T-cells or CD19CAR/R2+_ TCRαβ-_T-cells).

Criteria for inclusion in the study may include one or more of the following:

1. Histological or cytological diagnosis of large B-cell lymphoma as defined per 2018 WHO revision of lymphoma classification: diffuse large B-cell lymphoma (DLBCL)-not-otherwise specified (NOS) (germinal center B-cell [GCB], and non-GCB), DLBCL coexistent with follicular lymphoma of any grade, intravascular large B-cell lymphoma, DLBCL associated with chronic inflammation, anaplastic lymphoma kinase positive (ALK+) DLBCL, Epstein-Barr virus positive (EBV+) DLBCL-NOS, T cell/histiocyte-rich large B cell lymphoma, DLBCL with IRF4/MUM1 rearrangement, high-grade B cell lymphomas with translocation of MYC and BCL2 and/or BCL6 (double/triple hit), primary cutaneous DLBCL-leg type, transformation of follicular lymphoma to DLBCL, primary mediastinal B-cell lymphoma (PMBCL), and follicular lymphoma.

2. Relapsed or refractory aggressive large B-cell lymphoma or follicular lymphoma as defined by:
Primary refractory, defined as best response of progressive disease or stable disease after at least 4 cycles of first-line therapy (eg, 4 cycles of RCHOP) with stable disease duration no longer than 6 months from last dose of therapy
Refractory (defined as best response of stable disease or progressive disease) to second or greater line of therapy
Relapse ≤1 year following autologous stem cell transplant (SCT)

3. Patients must have received at least 2 lines of prior therapies including an anthracycline and an anti-CD20 monoclonal antibody.

4. Male or female patients ≥18 years

5. Eastern Cooperative Oncology Group (ECOG) performance status of 0 or 1

6. Estimated life expectancy of ≥12 weeks after ALLO-501 infusion (according to investigator's judgment)

7. Absence of donor-specific anti-HLA antibodies.

8. Adequate hematological function, including:
Absolute neutrophil count (ANC) ≥1,500/mm³ or ≥1.5×10⁹/L
Absolute lymphocyte count (ALC) ≥200/mm³ or ≥0.2× 10⁹/L
Platelet count ≥50,000/mm³ or ≥50×10⁹/L
Hemoglobin ≥9 g/dL 9. Adequate renal function, including:
Estimated creatinine clearance ≥60 mL/min as calculated using the method standard for the institution and not dialysis-dependent. In equivocal cases, a 24-hour urine collection test can be used to estimate the creatinine clearance more accurately.

10. Adequate liver function, including:
Total bilirubin ≤2.0 mg/dL, except in patients with Gilbert's Syndrome who must have a total bilirubin less than 3.0 mg/dL.
Aspartate and alanine aminotransferase (AST and ALT) ≤3×ULN, ≤5.0×ULN if there is liver involvement by the tumor;
Alkaline phosphatase ≤2.5×ULN (≤5×ULN in case of bone metastasis).

11. Normal blood oxygen saturation levels (SpO2) ≥91% on room air.

12. Left ventricular ejection fraction (LVEF) ≥45% and no hemodynamically significant pericardial effusion at screening.

13. Resolved acute effects of any prior therapy to baseline severity or CTCAE Grade ≤1 except for adverse events (AEs) not constituting a safety risk by investigator judgment.

14. Seronegative for hepatitis B antigen; positive hepatitis B tests can be further evaluated by confirmatory tests, and if confirmatory tests are negative, the patient can be enrolled.

15. Seronegative for hepatitis C antibody unless antigen negative. If hepatitis C antibody test is positive, then patients must be tested for the presence of antigen by RT-PCR and be HCV RNA negative.

16. Serum pregnancy test (for females of childbearing potential) negative at screening.

17. Female patients of non-childbearing potential must meet at least 1 of the following criteria:
Achieved postmenopausal status, defined as follows: cessation of regular menses for at least 12 consecutive months with no alternative pathological or physiological cause; status may be confirmed with a serum follicle-stimulating hormone (FSH) level confirming the postmenopausal state.
Have undergone a documented hysterectomy and/or bilateral oophorectomy.
Have medically confirmed ovarian failure.
All other female patients (including female patients with tubal ligations) are considered to be of childbearing potential.

18. Evidence of a personally signed and dated informed consent document indicating that the patient has been informed of all pertinent aspects of this study.

19. Willing and able to comply with scheduled visits, treatment plan, laboratory tests, and other procedures.

The phase 1 and phase 2 studies study will be divided into different periods including screening, lymphodepletion, treatment, and follow-up. A single cycle is defined as the combination of one lymphodepletion and one treatment period.

Screening will start after the informed consent form is signed. Patient's eligibility criteria will be checked. The Screening period will last up to 28 days. Patients who meet all eligibility criteria at the end of the Screening period will then enter the lymphodepletion period.

Lymphodepletion will start on Day −5 and end on UCART19 infusion at Day 0. Prior to treatment with UCART19, all patients will receive intravenous lymphodepletion with fludarabine (30 mg/m²/day), cyclophosphamide (300 mg/m²/day), and CD52 antibody (13 mg/day) on an outpatient setting on Day −5, Day −4 and Day −3. The CD52 antibody will be administered over approximately 4 hours and patients must be closely monitored up to 2 hours after the completion of infusion. Premedication comprising high-dose corticosteroids is required prior to CD52 antibody administration. If CD52 antibody-related dose-limiting toxicities (DLTs) are observed at the starting dose level, a lower dose of 30 mg total (10 mg/day given over 3 days) will be evaluated. At the end of the lymphodepletion period, eligibility criteria allowing UCART19 administration should be assessed to ensure patients' safety.

Treatment period, starting from Day 0, will end at Day 56 post-UCART19 infusion. Patients will receive UCART19 as an intravenous infusion on Day 0 over approximately 5 minutes. To closely manage toxicities associated with UCART19, patients will either be hospitalized for a minimum of 5 days from Day 0, or until UCART19 related non-hematological toxicities return to Grade ≤1, or receive UCART19 in an outpatient setting in those investigational sites allowing direct patient admission.

A dosing strategy for UCART19 using two different weight bands will be implemented, as shown below in Table 13:

TABLE 13

| Dose Level | Dose (×10⁶ CAR + viable cells) Patient weight > 50 kg | Dose (×10⁶ CAR + viable cells) Patient weight ≤ 50 kg |
|---|---|---|
| 1 (starting) | 40 | 20 |
| 2 | 120 | 80 |
| 3 | 360 | 240 |
| −1 | 20 | No treatment |

Follow-up will last from Day 56 to Month 9. Patients will be monitored during the follow-up period until the EOS visit at Month 9 after the first UCART19 infusion or upon their early withdrawal from the study. Patients will then be immediately rolled-over to a 15-year long-term follow-up under a separate long-term follow-up (LTFU) protocol.

Following cell kinetic and/or disease assessment, one optional retreatment with UCART19 may be administered to patients. Retreatment with UCART19 may be administered at the highest dose level deemed safe in Phase 1, or at the RP2D in Phase 2. Retreatment may use a batch and/or donor different from the initial dose. Each retreatment with UCART19 must be at least 4 weeks apart from the initial dose after planned tumor assessments on Day 56, Month 4, and Month 6 and must be following a lymphodepletion with Flu/Cy or Flu/Cy and CD52 antibody. Patients with undetectable UCART19 in whole blood at D14 may be retreated with subsequent lymphodepletion starting after the completion of the DLT observation window in Phase 1, or Day 28 in Phase 2. Patients who are eligible for re-treatment, will start a new cycle starting from the lymphodepletion (Day −5) until 2 months after re-dosing (Day 56) and will follow the same schedule of visits and assessments as described for the initial UCART19 infusion. At the end of the treatment period (Day 56) after the last UCART19 infusion, the patient will continue to the follow-up period as scheduled in the study plan. Re-treatment cannot occur after Month 6 (6 months following initial Day 0).

Although the disclosed teachings have been described with reference to various applications, methods, and compositions, it will be appreciated that various changes and modifications can be made without departing from the teachings herein and the claims below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method of treating a subject who has non-Hodgkin's lymphoma comprising administering to the subject allogeneic chimeric antigen receptor (CAR)-T cells (CAR-T cells) comprising an anti-human CD19 4-1BB/CD3zeta CAR, wherein the method comprises administering to the subject:
    a first lymphodepletion regimen, followed by
    at least one unit dose of $120\times10^6$ cells/dose to $360\times10^6$ cells/dose,
    wherein the anti-human CD19 4-1BB/CD3zeta CAR comprises an amino acid sequence of SEQ ID NO: 1.

2. The method of claim 1, wherein the non-Hodgkin's lymphoma is large B-cell lymphoma, follicular lymphoma or chronic lymphocytic leukemia.

3. The method of claim 2, wherein the at least one unit dose is a unit dose of $120\times10^6$ cells/dose, $240\times10^6$ cells/dose or $360\times10^6$ cells/dose.

4. The method of claim 3, wherein the first lymphodepletion regimen comprises administering fludarabine and cyclophosphamide.

5. The method of claim 4, wherein:
    (a) fludarabine is administered at a dosage of about 30 $mg/m^2/day$ and cyclophosphamide is administered at a dosage of about 300 $mg/m^2/day$ over the course of two to three days.

6. The method of claim 5, wherein the at least one unit dose is a unit dose of $120\times10^6$ cells/dose, $240\times10^6$ cells/dose or $360\times10^6$ cells/dose.

7. The method of claim 3, wherein the first lymphodepletion regimen comprises administering fludarabine and cyclophosphamide and an anti-CD52 antibody.

8. The method of claim 7, wherein the anti-CD52 antibody comprises the amino acid sequences of SEQ ID NO: 8 and SEQ ID NO: 10.

9. The method of claim 7, wherein:
    (a) fludarabine is administered at a dosage of about 30 $mg/m^2/day$, cyclophosphamide is administered at a dosage of about 300 $mg/m^2/day$, and anti-CD52 antibody is administered at a dosage of: about 10 to about 13 mg/day; or a total dose from about 0.3 to about 1 mg/kg, or a flat dose from about 30 to about 40 mg, from about 25 to about 60 mg or from about 100 to about 120 mg, over the course of three days.

10. The method of claim 9, wherein the anti-CD52 antibody comprises the amino acid sequences of SEQ ID NO: 8 and SEQ ID NO: 10.

11. The method of claim 10, wherein the at least one unit dose is a unit dose of $120\times10^6$ cells/dose, $240\times10^6$ cells/dose or $360\times10^6$ cells/dose.

12. The method of claim 2, wherein the first lymphodepletion regimen is initiated between about 1 to 15 days prior to administration of the at least one unit dose.

13. The method of claim 12, wherein the first lymphodepletion regimen is administered over the course of 1, 2, 3, 4, or 5 days.

14. The method of claim 13, wherein the at least one unit dose is a unit dose of $120\times10^6$ cells/dose.

15. The method of claim 7, wherein the CAR-T cells are CD52 deficient, or wherein the CAR-T cells comprise a mixture of CD52-deficient and CD52-positive cells.

16. The method of claim 2, wherein the CAR-T cells comprise UCART19 (CD19) CAR/RQR8+_TCRαβ-_T-cells.

17. The method of claim 1, wherein the CAR-T cells do not express a safety switch.

18. The method of claim 1, wherein the subject exhibits minimal residual disease.

19. The method of claim 12, wherein the subject exhibits minimal residual disease.

20. A method of treating a subject who has non-Hodgkin's lymphoma comprising administering to the subject allogeneic chimeric antigen receptor (CAR)-T cells (CAR-T cells) comprising an anti-human CD19 4-1BB/CD3zeta CAR, wherein the method comprises administering to the subject:
    (a) a first lymphodepletion regimen, wherein
        (i) the first lymphodepletion regimen comprises administering fludarabine and cyclophosphamide, wherein fludarabine is administered at a dosage of about 30 $mg/m^2/day$ and cyclophosphamide is administered at a dosage of about 300 $mg/m^2/day$ over the course of two to three days or
        (ii) the first lymphodepletion regimen comprises administering fludarabine and cyclophosphamide and an anti-CD52 antibody, wherein fludarabine is administered at a dosage of about 30 $mg/m^2/day$, cyclophosphamide is administered at a dosage of about 300 $mg/m^2/day$, and anti-CD52 antibody is administered at a dosage of: about 10 to about 13 mg/day; or a total dose from about 0.3 to about 1 mg/kg, or a flat dose from about 30 to about 40 mg, from about 25 to about 60 mg or from about 100 to about 120 mg, over the course of three days, the anti-CD52 antibody comprises the amino acid sequences of SEQ ID NO: 8 and SEQ ID NO: 10, and the CAR-T cells are CD52 deficient or the CAR-T cells comprise a mixture of CD52-deficient and CD52-positive cells, followed by
    (b) at least one unit dose of $120\times10^6$ CAR-T cells/dose or $360\times10^6$ CAR-T cells/dose,
    wherein:
    the first lymphodepletion regimen is initiated between about 1 to 15 days prior to administration of the at least one unit dose, and
    the anti-human CD19 4-1BB/CD3zeta CAR comprises an amino acid sequence of SEQ ID NO: 1.

21. A method of treating a subject who has large B-cell lymphoma, follicular lymphoma or chronic lymphocytic leukemia comprising administering to the subject allogeneic chimeric antigen receptor (CAR)-T cells (CAR-T cells) comprising an anti-human CD19 4-1BB/CD3zeta CAR, wherein the method comprises administering to the subject:
    (a) a first lymphodepletion regimen, wherein
        (i) the first lymphodepletion regimen comprises administering fludarabine and cyclophosphamide, wherein fludarabine is administered at a dosage of about 30 $mg/m^2/day$ and cyclophosphamide is administered at a dosage of about 300 $mg/m^2/day$ over the course of two to three days or
        (ii) the first lymphodepletion regimen comprises administering fludarabine and cyclophosphamide and an anti-CD52 antibody, wherein fludarabine is administered at a dosage of about 30 $mg/m^2/day$, cyclophosphamide is administered at a dosage of about 300 $mg/m^2/day$, and anti-CD52 antibody is administered at a dosage of: about 10 to about 13 mg/day; or a total dose from about 0.3 to about 1 mg/kg, or a flat dose from about 30 to about 40 mg, from about 25 to about 60 mg or from about 100 to about 120 mg, over the course of three days, the anti-CD52 antibody comprises the amino acid sequences of SEQ ID NO: 8 and SEQ ID NO: 10, and the CAR-T cells are CD52 deficient or the CAR-T cells comprise a mixture of CD52-deficient and CD52-positive cells, followed by (b) at least one unit dose of $120 \times 10^6$ CAR-T cells/dose or $360 \times 10^6$ CAR-T cells/dose, wherein:

the first lymphodepletion regimen is initiated between about 1 to 15 days prior to administration of the at least one unit dose, and the anti-human CD19 4-1BB/CD3zeta CAR comprises an amino acid sequence of SEQ ID NO: 1.

22. The method of claim 21, wherein the subject has large B-cell lymphoma.

23. The method of claim 21, wherein the subject has follicular lymphoma.

24. The method of claim 21, wherein the subject has chronic lymphocytic leukemia.

25. The method of claim 21, wherein the subject exhibits minimal residual disease.

\* \* \* \* \*

SEQUENCE LISTING

```
Sequence total quantity: 35
SEQ ID NO: 1              moltype = AA  length = 495
FEATURE                  Location/Qualifiers
REGION                   1..495
                         note = CAR full length amino acid sequence (version 2)
source                   1..495
                         mol_type = protein
                         organism = synthetic construct
SEQUENCE: 1
METDTLLLWV LLLWVPGSTG EVQLQQSGPE LIKPGASVKM SCKASGYTFT SYVMHWVKQK  60
PGQGLEWIGY INPYNDGTKY NEKFKGKATL TSDKSSSTAY MELSSLTSED SAVYYCARGT  120
YYYGSRVFDY WGQGTTLTVS SGGGGSGGGG SGGGGSDIVM TQAAPSIPVT PGESVSISCR  180
SSKSLLNSNG NTYLYWFLQR PGQSPQLLIY RMSNLASGVP DRFSGSGSGT AFTLRISRVE  240
AEDVGVYYCM QHLEYPFTFG AGTKLELKRS DPTTTPAPRP PTPAPTIASQ PLSLRPEACR  300
PAAGGAVHTR GLDFACDIYI WAPLAGTCGV LLLSLVITLY CKRGRKKLLY IFKQPFMRPV  360
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 2              moltype = AA  length = 5
FEATURE                  Location/Qualifiers
REGION                   1..5
                         note = CD52 antibody HCDR1
source                   1..5
                         mol_type = protein
                         organism = synthetic construct
SEQUENCE: 2
DFYMN                                                              5

SEQ ID NO: 3              moltype = AA  length = 19
```

```
FEATURE              Location/Qualifiers
REGION               1..19
                     note = CD52 antibody HCDR2
source               1..19
                     mol_type = protein
                     organism = synthetic construct
SEQUENCE: 3
FIRDKAKGYT TEYNPSVKG                                                    19

SEQ ID NO: 4         moltype = AA  length = 10
FEATURE              Location/Qualifiers
REGION               1..10
                     note = CD52 antibody HCDR3
source               1..10
                     mol_type = protein
                     organism = synthetic construct
SEQUENCE: 4
EGHTAAPFDY                                                              10

SEQ ID NO: 5         moltype = AA  length = 11
FEATURE              Location/Qualifiers
REGION               1..11
                     note = CD52 antibody LCDR1
source               1..11
                     mol_type = protein
                     organism = synthetic construct
SEQUENCE: 5
KASQNIDKYL N                                                            11

SEQ ID NO: 6         moltype = AA  length = 7
FEATURE              Location/Qualifiers
REGION               1..7
                     note = CD52 antibody LCDR2
source               1..7
                     mol_type = protein
                     organism = synthetic construct
SEQUENCE: 6
NTNNLQT                                                                 7

SEQ ID NO: 7         moltype = AA  length = 9
FEATURE              Location/Qualifiers
REGION               1..9
                     note = CD52 antibody LCDR3
source               1..9
                     mol_type = protein
                     organism = synthetic construct
SEQUENCE: 7
LQHISRPRT                                                               9

SEQ ID NO: 8         moltype = AA  length = 451
FEATURE              Location/Qualifiers
REGION               1..451
                     note = CD52 antibody VH
source               1..451
                     mol_type = protein
                     organism = synthetic construct
SEQUENCE: 8
QVQLQESGPG LVRPSQTLSL TCTVSGFTFT DFYMNWVRQP PGRGLEWIGF IRDKAKGYTT   60
EYNPSVKGRV TMLVDTSKNQ FSLRLSSVTA ADTAVYYCAR EGHTAAPFDY WGQGSLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                  451

SEQ ID NO: 9         moltype = DNA  length = 1353
FEATURE              Location/Qualifiers
misc_feature         1..1353
                     note = CD52 antibody VH
source               1..1353
                     mol_type = other DNA
                     organism = synthetic construct
SEQUENCE: 9
caagtgcagc ttcaagaatc cggccctggt ctggtccgcc cctcccaaac cctctccctg   60
acatgcaccg tgtcgggatt caccttttacc gatttctaca tgaactgggt ccggcagccg  120
cccggaagag gtctggagtg gatcggcttc attcgggaca aagccaaggg gtacaccacc  180
gagtacaacc cgtccgtgaa gggacgcgtg actatgctcg tggacacgtc caagaaccag  240
ttcagcttga ggctgagcag cgtgactgcc gcggataccg cagtgtacta ctgtgcccgg  300
```

```
gaagggcaca ctgccgctcc attcgactat tggggccagg gatcactggt cactgtgtcg   360
tccgcctcca ccaagggccc atcggtcttc cccctggcac cctcctccaa gagcacctct   420
gggggcacag cggccctggg ctgcctggtc aaggactact tccccgaacc ggtgacggtg   480
tcgtggaact caggcgccct gaccagcggc gtgcacacct tcccggctgt cctacagtcc   540
tcaggactct actccctcag cagcgtagtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc ccaccgtgcc cagcacctga actcctgggg   720
ggaccgtcag tcttcctctt ccccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag cccccatcga gaaaaccatc   1020
tccaaagcca aagggcagcc ccgagaacca caggtgtaca ccctgccccc atcccgggac   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tatagcaagc tcaccgtgga caagagcagg   1260
tggcagcagg ggaacgtctt ctcatgctcc gtgatgcatg aggctctgca caaccactac   1320
acgcagaaga gcctctccct gtctccggga aaa                                 1353
```

```
SEQ ID NO: 10               moltype = AA   length = 214
FEATURE                     Location/Qualifiers
REGION                      1..214
                            note = CD52 antibody VL
source                      1..214
                            mol_type = protein
                            organism = synthetic construct
SEQUENCE: 10
DIQMTQSPSS LSASVGDRVT ITCKASQNID KYLNWYQQKP GKAPKLLIYN TNNLQTGVPS   60
RFSGSGSGTD FTFTISSLQP EDIATYYCLQ HISRPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                 214
```

```
SEQ ID NO: 11               moltype = DNA   length = 699
FEATURE                     Location/Qualifiers
misc_feature                1..699
                            note = CD52 antibody VL
source                      1..699
                            mol_type = other DNA
                            organism = synthetic construct
SEQUENCE: 11
atgggatgga gctgtatcat cctcttcttg gtagcaacag ctacaggcgt gcactccgac   60
atccaaatga cccaatcccc atcctcactt tccgcctccg tgggcgaccg cgtgactatt   120
acctgtaaag cgtcacagaa tatcgacaag tacctgaact ggtaccagca gaagcctggc   180
aaggccccca agctcctgat ctacaacacc aacaacttgc agactggagt gccgagcaga   240
ttttccggct ccggctcggg gactgatttc accttcacca tctcgagcct gcagccggag   300
gatattgcta cctattactg cctgcaacac attagccggc caggacgtt cggacagggt   360
accaaggtcg aaatcaagcg tacggtggct gcaccatctg tcttcatctt cccgccatct   420
gatgagcagt tgaaatctgg aactgcctct gttgtgtgcc tgctgaataa cttctatccc   480
agagaggcca agtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgt                          699
```

```
SEQ ID NO: 12               moltype = AA   length = 177
FEATURE                     Location/Qualifiers
REGION                      1..177
                            note = Full length RQR8 safety switch
source                      1..177
                            mol_type = protein
                            organism = synthetic construct
SEQUENCE: 12
MLTSLLCWMA LCLLGADHAD ACPYSNPSLC SGGGGSELPT QGTFSNVSTN VSPAKPTTTA   60
CPYSNPSLCS GGGGSPAPRP PTPAPTIASQ PLSLRPEACR PAAGGAVHTR GLDFACDIYI   120
WAPLAGTCGV LLLSLVITLY CNHRNRRRVC KCPRPVVRAE GRGSLLTCGD VEENPGP      177
```

```
SEQ ID NO: 13               moltype = AA   length = 21
FEATURE                     Location/Qualifiers
REGION                      1..21
                            note = Human TCR beta leader sequence (with G to L
                            substitution)
source                      1..21
                            mol_type = protein
                            organism = synthetic construct
SEQUENCE: 13
MLTSLLCWMA LCLLGADHAD A                                              21
```

```
SEQ ID NO: 14               moltype = AA   length = 9
FEATURE                     Location/Qualifiers
REGION                      1..9
```

```
                        note = Rituximab epitope
source                  1..9
                        mol_type = protein
                        organism = synthetic construct
SEQUENCE: 14
CPYSNPSLC                                                                    9

SEQ ID NO: 15           moltype = AA  length = 6
FEATURE                 Location/Qualifiers
REGION                  1..6
                        note = glycine-serine linker
source                  1..6
                        mol_type = protein
                        organism = synthetic construct
SEQUENCE: 15
SGGGGS                                                                       6

SEQ ID NO: 16           moltype = AA  length = 16
FEATURE                 Location/Qualifiers
source                  1..16
                        mol_type = protein
                        organism = Homo sapiens
SEQUENCE: 16
ELPTQGTFSN VSTNVS                                                            16

SEQ ID NO: 17           moltype = AA  length = 7
FEATURE                 Location/Qualifiers
source                  1..7
                        mol_type = protein
                        organism = Homo sapiens
SEQUENCE: 17
PAKPTTT                                                                      7

SEQ ID NO: 18           moltype = AA  length = 42
FEATURE                 Location/Qualifiers
source                  1..42
                        mol_type = protein
                        organism = Homo sapiens
SEQUENCE: 18
PAPRPPTPAP TIASQPLSLR PEACRPAAGG AVHTRGLDFA CD                               42

SEQ ID NO: 19           moltype = AA  length = 21
FEATURE                 Location/Qualifiers
source                  1..21
                        mol_type = protein
                        organism = Homo sapiens
SEQUENCE: 19
IYIWAPLAGT CGVLLLSLVI T                                                      21

SEQ ID NO: 20           moltype = AA  length = 19
FEATURE                 Location/Qualifiers
source                  1..19
                        mol_type = protein
                        organism = Homo sapiens
SEQUENCE: 20
LYCNHRNRRR VCKCPRPVV                                                         19

SEQ ID NO: 21           moltype = AA  length = 19
FEATURE                 Location/Qualifiers
source                  1..19
                        mol_type = protein
                        organism = Thosea asigna virus
SEQUENCE: 21
RAEGRGSLLT CGDVEENPG                                                         19

SEQ ID NO: 22           moltype = AA  length = 495
FEATURE                 Location/Qualifiers
REGION                  1..495
                        note = CAR full length amino acid sequence (version 1)
source                  1..495
                        mol_type = protein
                        organism = synthetic construct
SEQUENCE: 22
MALPVTALLL PLALLLHAAR PEVQLQQSGP ELIKPGASVK MSCKASGYTF TSYVMHWVKQ           60
KPGQGLEWIG YINPYNDGTK YNEKFKGKAT LTSDKSSSTA YMELSSLTSE DSAVYYCARG           120
TYYYGSRVFD YWGQGTTLTV SSGGGGSGGG GSGGGGSDIV MTQAAPSIPV TPGESVSISC           180
RSSKSLLNSN GNTYLYWFLQ RPGQSPQLLI YRMSNLASGV PDRFSGSGSG TAFTLRISRV           240
EAEDVGVYYC MQHLEYPFTF GAGTKLELKR ADTTTPAPRP PTPAPTIASQ PLSLRPEACR           300
PAAGGAVHTR GLDFACDIYI WAPLAGTCGV LLLSLVITLY CKRGRKKLLY IFKQPFMRPV           360
```

-continued

```
QTTQEEDGCS CRFPEEEEGG CELRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                    495

SEQ ID NO: 23           moltype = AA   length = 672
FEATURE                 Location/Qualifiers
REGION                  1..672
                        note = UCART19 CAR full length amino acid sequence with
                         RQR8 safetyswitch
source                  1..672
                        mol_type = protein
                        organism = synthetic construct
SEQUENCE: 23
MLTSLLCWMA LCLLGADHAD ACPYSNPSLC SGGGGSELPT QGTFSNVSTN VSPAKPTTTA  60
CPYSNPSLCS GGGGSPAPRP PTPAPTIASQ PLSLRPEACR PAAGGAVHTR GLDFACDIYI  120
WAPLAGTCGV LLLSLVITLY CNHRNRRRVC KCPRPVVRAE GRGSLLTCGD VEENPGPMET  180
DTLLLWVLLL WVPGSTGEVQ LQQSGPELIK PGASVKMSCK ASGYTFTSYV MHWVKQKPGQ  240
GLEWIGYINP YNDGTKYNEK FKGKATLTSD KSSSTAYMEL SSLTSEDSAV YYCARGTYYY  300
GSRVFDYWGQ GTTLTVSSGG GGSGGGGSGG GGSDIVMTQA APSIPVTPGE SVSISCRSSK  360
SLLNSNGNTY LYWFLQRPGQ SPQLLIYRMS NLASGVPDRF SGSGSGTAFT LRISRVEAED  420
VGVYYCMQHL EYPFTFGAGT KLELKRSDPT TTPAPRPPTP APTIASQPLS LRPEACRPAA  480
GGAVHTRGLD FACDIYIWAP LAGTCGVLLL SLVITLYCKR GRKKLLYIFK QPFMRPVQTT  540
QEEDGCSCRF PEEEEGGCEL RVKFSRSADA PAYQQGQNQL YNELNLGRRE EYDVLDKRRG  600
RDPEMGGKPR RKNPQEGLYN ELQKDKMAEA YSEIGMKGER RRGKGHDGLY QGLSTATKDT  660
YDALHMQALP PR                                                       672

SEQ ID NO: 24           moltype = AA   length = 20
FEATURE                 Location/Qualifiers
source                  1..20
                        mol_type = protein
                        organism = Mus musculus
SEQUENCE: 24
METDTLLLWV LLLWVPGSTG                                               20

SEQ ID NO: 25           moltype = AA   length = 121
FEATURE                 Location/Qualifiers
source                  1..121
                        mol_type = protein
                        organism = Mus musculus
SEQUENCE: 25
EVQLQQSGPE LIKPGASVKM SCKASGYTFT SYVMHWVKQK PGQGLEWIGY INPYNDGTKY  60
NEKFKGKATL TSDKSSSTAY MELSSLTSED SAVYYCARGT YYYGSRVFDY WGQGTTLTVS  120
S                                                                   121

SEQ ID NO: 26           moltype = AA   length = 15
FEATURE                 Location/Qualifiers
REGION                  1..15
                        note = Glycine-serine linker
source                  1..15
                        mol_type = protein
                        organism = synthetic construct
SEQUENCE: 26
GGGGSGGGGS GGGGS                                                    15

SEQ ID NO: 27           moltype = AA   length = 115
FEATURE                 Location/Qualifiers
REGION                  1..115
                        note = Mouse anti-human CD19 (4G7) kappa light chain (with
                         A to Ssubstitution) (CDRs)
source                  1..115
                        mol_type = protein
                        organism = synthetic construct
SEQUENCE: 27
DIVMTQAAPS IPVTPGESVS ISCRSSKSLL NSNGNTYLYW FLQRPGQSPQ LLIYRMSNLA  60
SGVPDRFSGS GSGTAFTLRI SRVEAEDVGV YYCMQHLEYP FTFGAGTKLE LKRSD        115

SEQ ID NO: 28           moltype = AA   length = 252
FEATURE                 Location/Qualifiers
REGION                  1..252
                        note = Extracellular binding domain (version 2)
source                  1..252
                        mol_type = protein
                        organism = synthetic construct
SEQUENCE: 28
EVQLQQSGPE LIKPGASVKM SCKASGYTFT SYVMHWVKQK PGQGLEWIGY INPYNDGTKY  60
NEKFKGKATL TSDKSSSTAY MELSSLTSED SAVYYCARGT YYYGSRVFDY WGQGTTLTVS  120
SGGGGSGGGG SGGGGSDIVM TQAAPSIPVT PGESVSISCR SSKSLLNSNG NTYLYWFLQR  180
PGQSPQLLIY RMSNLASGVP DRFSGSGSGT AFTLRISRVE AEDVGVYYCM QHLEYPFTFG  240
AGTKLELKRS DP                                                       252
```

-continued

```
SEQ ID NO: 29          moltype = AA  length = 251
FEATURE                Location/Qualifiers
REGION                 1..251
                       note = Extracellular binding domain (version 1)
source                 1..251
                       mol_type = protein
                       organism = synthetic construct
SEQUENCE: 29
EVQLQQSGPE LIKPGASVKM SCKASGYTFT SYVMHWVKQK PGQGLEWIGY INPYNDGTKY  60
NEKFKGKATL TSDKSSSTAY MELSSLTSED SAVYYCARGT YYYGSRVFDY WGQGTTLTVS  120
SGGGGSGGGG SGGGGSDIVM TQAAPSIPVT PGESVSISCR SSKSLLNSNG NTYLYWFLQR  180
PGQSPQLLIY RMSNLASGVP DRFSGSGSGT AFTLRISRVE AEDVGVYYCM QHLEYPFTFG  240
AGTKLELKRA D                                                       251

SEQ ID NO: 30          moltype = AA  length = 46
FEATURE                Location/Qualifiers
source                 1..46
                       mol_type = protein
                       organism = Homo sapiens
SEQUENCE: 30
PTTTPAPRPP TPAPTIASQP LSLRPEACRP AAGGAVHTRG LDFACD                 46

SEQ ID NO: 31          moltype = AA  length = 21
FEATURE                Location/Qualifiers
source                 1..21
                       mol_type = protein
                       organism = Homo sapiens
SEQUENCE: 31
IYIWAPLAGT CGVLLLSLVI T                                            21

SEQ ID NO: 32          moltype = AA  length = 69
FEATURE                Location/Qualifiers
REGION                 1..69
                       note = Fragment of T-cell surface glycoprotein CD8 alpha
                        chain isoform 1precursor (residues 138-206)
source                 1..69
                       mol_type = protein
                       organism = synthetic construct
SEQUENCE: 32
TTTPAPRPPT PAPTIASQPL SLRPEACRPA AGGAVHTRGL DFACDIYIWA PLAGTCGVLL  60
LSLVITLYC                                                          69

SEQ ID NO: 33          moltype =   length =
SEQUENCE: 33
000

SEQ ID NO: 34          moltype = AA  length = 42
FEATURE                Location/Qualifiers
source                 1..42
                       mol_type = protein
                       organism = Homo sapiens
SEQUENCE: 34
KRGRKKLLYI FKQPFMRPVQ TTQEEDGCSC RFPEEEEGGC EL                     42

SEQ ID NO: 35          moltype = AA  length = 112
FEATURE                Location/Qualifiers
source                 1..112
                       mol_type = protein
                       organism = Homo sapiens
SEQUENCE: 35
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112
```